(12) United States Patent
Shachar

(10) Patent No.: US 7,873,401 B2
(45) Date of Patent: Jan. 18, 2011

(54) SYSTEM AND METHOD FOR A MAGNETIC CATHETER TIP

(75) Inventor: Yehoshua Shachar, Santa Monica, CA (US)

(73) Assignee: Magnetecs, Inc., Inglewood, CA (US)

( * ) Notice: Subject to any disclaimer, the term of this patent is extended or adjusted under 35 U.S.C. 154(b) by 591 days.

(21) Appl. No.: 11/331,485

(22) Filed: Jan. 13, 2006

(65) Prior Publication Data

US 2006/0116633 A1 Jun. 1, 2006

Related U.S. Application Data

(62) Division of application No. 10/621,196, filed on Jul. 15, 2003, now Pat. No. 7,769,427.

(60) Provisional application No. 60/396,302, filed on Jul. 16, 2002.

(51) Int. Cl.
*A61B 5/05* (2006.01)
(52) U.S. Cl. ...................................................... 600/424
(58) Field of Classification Search ................ 600/435, 600/424, 461, 437, 447; 604/95.01; 128/916
See application file for complete search history.

(56) References Cited

U.S. PATENT DOCUMENTS

| 3,043,309 A | 7/1962 | McCarthy |
| 3,358,676 A | 12/1967 | Frei et al. |
| 3,622,869 A | 11/1971 | Golay |
| 3,628,527 A | 12/1971 | West |
| 3,746,937 A | 7/1973 | Koike |
| 3,961,632 A | 6/1976 | Moossun |
| 4,063,561 A | 12/1977 | McKenna |
| 4,096,862 A | 6/1978 | DeLuca |
| 4,162,679 A | 7/1979 | Reenstierna |
| 4,173,228 A | 11/1979 | Van Steenwyk et al. |
| 4,244,362 A | 1/1981 | Anderson |
| 4,249,536 A | 2/1981 | Vega |
| 4,270,252 A | 6/1981 | Harrison et al. |

(Continued)

FOREIGN PATENT DOCUMENTS

DE 102005045073 3/2007

(Continued)

OTHER PUBLICATIONS

Office Action dated Feb. 5, 2008 from Related U.S. Appl. No. 10/621,196.

(Continued)

*Primary Examiner*—Max Hindenburg
*Assistant Examiner*—Brian Szmal
(74) *Attorney, Agent, or Firm*—Knobbe, Martens, Olson & Bear, LLP

(57) ABSTRACT

A system whereby a magnetic tip attached to a surgical tool is detected, displayed and influenced positionally so as to allow diagnostic and therapeutic procedures to be performed rapidly, accurately, simply, and intuitively is described. The tools that can be so equipped include catheters, guidewires, and secondary tools such as lasers and balloons, in addition biopsy needles, endoscopy probes, and similar devices. The tip position and orientation information and the dynamic body part position information are also utilized to provide a display that allows three dimensional viewing of the magnetic tip position and orientation relative to the body part.

11 Claims, 29 Drawing Sheets

U.S. PATENT DOCUMENTS

| | | |
|---|---|---|
| 4,292,961 A | 10/1981 | Kawashima |
| 4,354,501 A | 10/1982 | Colley et al. |
| 4,392,634 A | 7/1983 | Kita |
| 4,671,287 A | 6/1987 | Fiddian-Green |
| 4,727,344 A | 2/1988 | Koga et al. |
| 4,735,211 A | 4/1988 | Takasugi |
| 4,809,713 A | 3/1989 | Grayzel |
| 4,869,247 A | 9/1989 | Howard, III et al. |
| 4,943,770 A | 7/1990 | Ashley-Rollman et al. |
| 4,984,581 A | 1/1991 | Stice |
| 4,985,015 A * | 1/1991 | Obermann et al. ............ 604/67 |
| 5,063,935 A | 11/1991 | Gambale |
| 5,083,562 A | 1/1992 | de Coriolis et al. |
| 5,090,956 A | 2/1992 | McCoy |
| 5,125,888 A | 6/1992 | Howard et al. |
| 5,167,626 A | 12/1992 | Casper et al. |
| 5,209,234 A | 5/1993 | LaRocca |
| 5,226,847 A | 7/1993 | Thomas et al. |
| 5,249,163 A | 9/1993 | Erickson |
| 5,255,680 A | 10/1993 | Darrow et al. |
| 5,257,636 A | 11/1993 | White |
| 5,269,759 A | 12/1993 | Hernandez et al. |
| 5,353,807 A | 10/1994 | DeMarco |
| 5,377,678 A | 1/1995 | Dumoulin et al. |
| 5,396,902 A | 3/1995 | Brennen et al. |
| 5,492,131 A | 2/1996 | Galel |
| 5,546,948 A | 8/1996 | Hamm et al. |
| 5,550,469 A | 8/1996 | Tanabe et al. |
| 5,558,091 A | 9/1996 | Acker et al. |
| 5,573,012 A | 11/1996 | McEwan |
| 5,588,442 A | 12/1996 | Scovil et al. |
| 5,624,430 A | 4/1997 | Eton et al. |
| 5,645,065 A | 7/1997 | Shapiro et al. |
| 5,650,725 A | 7/1997 | Powell et al. |
| 5,654,864 A | 8/1997 | Ritter et al. |
| 5,656,030 A | 8/1997 | Hunjan et al. |
| 5,681,260 A | 10/1997 | Ueda et al. |
| 5,683,384 A | 11/1997 | Gough et al. |
| 5,702,433 A | 12/1997 | Taylor et al. |
| 5,704,897 A | 1/1998 | Truppe |
| 5,709,661 A | 1/1998 | Van Egmond et al. |
| 5,711,299 A | 1/1998 | Manwaring et al. |
| 5,775,322 A | 7/1998 | Silverstein et al. |
| 5,779,694 A | 7/1998 | Howard et al. |
| 5,808,665 A | 9/1998 | Green |
| 5,821,920 A | 10/1998 | Rosenberg et al. |
| 5,843,153 A | 12/1998 | Seale |
| 5,844,140 A | 12/1998 | Seale |
| 5,904,691 A | 5/1999 | Barnett et al. |
| 5,931,818 A | 8/1999 | Werp et al. |
| 5,971,976 A | 10/1999 | Wang et al. |
| 6,014,580 A | 1/2000 | Blume et al. |
| 6,015,414 A | 1/2000 | Werp et al. |
| 6,038,488 A | 3/2000 | Barnes et al. |
| 6,104,944 A | 8/2000 | Martinelli |
| 6,122,538 A | 9/2000 | Sliwa et al. |
| 6,128,174 A | 10/2000 | Ritter et al. |
| 6,129,668 A | 10/2000 | Haynor et al. |
| 6,148,823 A | 11/2000 | Hastings |
| 6,152,933 A | 11/2000 | Werp et al. |
| 6,157,853 A | 12/2000 | Blume et al. |
| 6,200,312 B1 | 3/2001 | Zikorus et al. |
| 6,241,671 B1 | 6/2001 | Ritter et al. |
| 6,292,678 B1 | 9/2001 | Hall et al. |
| 6,295,466 B1 | 9/2001 | Ishikawa et al. |
| 6,296,604 B1 | 10/2001 | Garibaldi et al. |
| 6,298,257 B1 | 10/2001 | Garibaldi et al. |
| 6,304,768 B1 | 10/2001 | Blume et al. |
| 6,311,082 B1 | 10/2001 | Creighton, IV et al. |
| 6,314,312 B1 | 11/2001 | Wessels et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,454,776 B1 | 9/2002 | Tajima et al. |
| 6,459,924 B1 | 10/2002 | Creighton, IV et al. |
| 6,459,926 B1 | 10/2002 | Nowlin et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,529,761 B2 | 3/2003 | Creighton, IV et al. |
| 6,537,196 B1 | 3/2003 | Creighton, IV et al. |
| 6,562,019 B1 | 5/2003 | Sell |
| 6,575,977 B1 | 6/2003 | Michelson |
| 6,587,709 B2 | 7/2003 | Solf et al. |
| 6,594,517 B1 | 7/2003 | Nevo |
| 6,630,879 B1 | 10/2003 | Creighton, IV et al. |
| 6,662,034 B2 | 12/2003 | Segner et al. |
| 6,667,660 B2 | 12/2003 | Schrodinger et al. |
| 6,669,693 B2 | 12/2003 | Friedman |
| 6,677,752 B1 | 1/2004 | Creighton, IV et al. |
| 6,702,804 B1 | 3/2004 | Ritter et al. |
| 6,704,694 B1 | 3/2004 | Basdogan et al. |
| 6,726,675 B1 | 4/2004 | Beyar |
| 6,733,511 B2 | 5/2004 | Hall et al. |
| 6,740,103 B2 | 5/2004 | Hall et al. |
| 6,755,816 B2 | 6/2004 | Ritter et al. |
| 6,776,165 B2 | 8/2004 | Jin |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,853,965 B2 | 2/2005 | Massie et al. |
| 6,902,528 B1 | 6/2005 | Garibaldi et al. |
| 6,914,552 B1 | 7/2005 | McEwan |
| 6,960,847 B2 | 11/2005 | Suzuki et al. |
| 7,280,863 B2 | 10/2007 | Shachar |
| 7,316,700 B2 | 1/2008 | Alden et al. |
| 7,341,063 B2 | 3/2008 | Garbibaldi et al. |
| 7,346,379 B2 | 3/2008 | Eng et al. |
| 7,495,537 B2 | 2/2009 | Tunay |
| 7,543,239 B2 | 6/2009 | Viswanathan et al. |
| 2001/0004215 A1 | 6/2001 | Kubota et al. |
| 2002/0022777 A1 | 2/2002 | Crieghton, IV et al. |
| 2002/0055674 A1 | 5/2002 | Ben-Haim et al. |
| 2002/0103430 A1 | 8/2002 | Hastings et al. |
| 2003/0205941 A1 | 11/2003 | Suzuki et al. |
| 2003/0233112 A1 | 12/2003 | Alden et al. |
| 2004/0019447 A1 | 1/2004 | Shachar |
| 2005/0004449 A1 | 1/2005 | Mitschke et al. |
| 2005/0096589 A1 | 5/2005 | Shachar |
| 2005/0256521 A1 | 11/2005 | Kozel |
| 2006/0114088 A1 | 6/2006 | Shachar |
| 2006/0116633 A1 | 6/2006 | Shachar |
| 2006/0116634 A1 | 6/2006 | Shachar |
| 2006/0217697 A1 | 9/2006 | Lau et al. |
| 2007/0016006 A1 | 1/2007 | Shachar |
| 2007/0062547 A1 | 3/2007 | Pappone |
| 2007/0197891 A1 | 8/2007 | Shachar |
| 2008/0027313 A1 | 1/2008 | Shachar |
| 2008/0249395 A1 | 10/2008 | Shachar et al. |
| 2008/0297287 A1 | 12/2008 | Shachar et al. |
| 2009/0248014 A1 | 10/2009 | Shachar et al. |
| 2009/0253985 A1 | 10/2009 | Shachar et al. |

| | | |
|---|---|---|
| 2009/0275828 A1 | 11/2009 | Shachar et al. |

FOREIGN PATENT DOCUMENTS

| | | |
|---|---|---|
| EP | 0147082 A2 | 7/1985 |
| EP | 1059067 A1 | 12/2000 |
| EP | 1 115 327 | 7/2001 |
| GB | 2367803 A | 4/2002 |
| JP | 2000-509316 | 7/2000 |
| JP | 2001-448 | 1/2001 |
| JP | 2001-509038 | 7/2001 |
| JP | 2001-514040 | 9/2001 |
| WO | WO 95-01757 A1 | 1/1995 |
| WO | WO 97-29803 A1 | 8/1997 |
| WO | WO 98-35720 A2 | 8/1998 |
| WO | WO 99-11189 A1 | 3/1999 |
| WO | WO 99-23934 A2 | 5/1999 |
| WO | WO 02-34131 A1 | 5/2002 |
| WO | WO 02-094115 A2 | 11/2002 |
| WO | WO 02-094115 A3 | 11/2002 |
| WO | WO 2004-006795 A1 | 1/2004 |
| WO | WO 2005-042053 A2 | 5/2005 |
| WO | WO 2005-042053 A3 | 5/2005 |
| WO | WO 2005-112813 A1 | 12/2005 |
| WO | WO 2007-100559 A2 | 9/2007 |

OTHER PUBLICATIONS

Office Action dated Feb. 22, 2006 from Related U.S. Appl. No. 10/621,196.
Office Action dated Nov. 14, 2006 from Related U.S. Appl. No. 10/621,196.
Office Action dated Apr. 18, 2007 from Related U.S. Appl. No. 10/621,196.
Office Action dated May 18, 2006 from Related U.S. Appl. No. 10/690,472.
Office Action dated Jan. 30, 2007 from Related U.S. Appl. No. 10/690,472.
Notice of Allowance dated Aug. 6, 2007 from Related U.S. Appl. No. 10/690,472.
Office Action dated Sep. 10, 2007 from Related U.S. Appl. No. 10/621,196.
Advisory Action dated Nov. 6, 2007 from Related U.S. Appl. No. 10/621,196.
International Search Report from PCT/US2007/004416, Aug. 24, 2007, 5 pages.
Bergveld, Piet, "Development, Operation, and Application of the Ion-Sensitive Field Effect Transistor as a Tool for Electrophysiology", IEEE Transactions on Biomedical Engineering, vol. BME-19, No. 5, Sep. 1972, 10 pages.
Office Action dated Jul. 10, 2008 from Related U.S. Appl. No. 10/621,196.
Office Action dated Aug. 8, 2008 from Related U.S. Appl. No. 11/140,475.
International Search Report from PCT/US2008/060525, Oct. 31, 2008, 6 pages.
Fink et al.,"An Optically Switched PS-Radar for Pictorial Representation of Object Structures in Human Tissue," Experimentelle Technik Der Physik, vol. 38, No. 3, 1990, pp. 197-206, 10 pages.
International Search Report from PCT/US2008/056277, Nov. 18, 2008, 5 pages.
Supplementary Partial Search Report from 04795885.5, Nov. 18, 2008, 5 pages.
Extended European Search Report from 09005296.0, Aug. 19, 2009, 3 pages.
Faddis et al., "Novel, Magnetically Guided Catheter for Endocardial Mapping and Radiofrequency Catheter Ablation," Journal of the American Heart Association, Nov. 11, 2002.
International Search Report from PCT Application No. PCT/US03/22122; 9 pages.
International Search Report from PCT/US2009/039659, Sep. 3, 2009, 4 pages.
Office Action dated Dec. 25, 2005 from Related U.S. Appl. No. 10/621,196.
Advisory Action dated Mar. 6, 2007 from Related U.S. Appl. No. 10/621,196.
Office Action dated Dec. 2, 2008 from Related U.S. Appl. No. 10/621,196.
Office Action dated Aug. 25, 2009 from Related U.S. Appl. No. 10/621,196.
Office Action dated Jan. 29, 2009 from Related U.S. Appl. No. 11/331,781.
Office Action dated Sep. 22, 2009 from Related U.S. Appl. No. 11/331,781.
Office Action dated Feb. 25, 2009 from Related U.S. Appl. No. 11/331,944.
Office Action dated Nov. 30, 2009 from Related U.S. Appl. No. 11/331,944.
Supplemental Notice of Allowance dated Aug. 6, 2007 from Related U.S. Appl. No. 10/690,472.
Office Action dated Sep. 2, 2009 from Related U.S. Appl. No. 11/140,475.
Advisory Action dated Nov. 27, 2009 from Related U.S. Appl. No. 11/140,475.
Office Action dated May 6, 2009 from Related U.S. Appl. No. 11/362,542.
Office Action dated Jul. 13, 2009 from Related U.S. Appl. No. 11/362,542.
International Search Report from PCT/US2009/039659, Jul. 6, 2009, 4 pages.
Fink et al., "An Optically Switched PS-Radar for Pictorial Representation of Object Structures in Human Tissue," Experimentelle Technik De Physik, vol. 38, No. 3, 1990, pp. 197-206, 10 pages.
International Search Report from PCT/US2008/056277, Nov. 18, 2008, 7 pages.
International Search Report from PCT/US2008/060525, October 31, 2008, 6 pages.
Ishiyama, K.; Sendoh, M.; Arai, K.I.; Magnetic micromachines for medical applications. Journal of Magnetism and Magnetic Materials. 2002; vol. 242; pp. 41-46.
Ritter, J.A.; Ebner, A.D.;Daniel, K.D.; Stewart, K.L.; Application of high gradient magnetic separation principles to magnetic drug targeting. Journal of Magnetism and Magnetic Materials. 2004; vol. 280; pp. 184-201.
Supplementary Partial European Search Report from 04795885.5, Nov. 18, 2008, 5 pages.
Totsu, K.; Haga, Y.; Esashi, M.; Three-axis magneto-impedance effect sensor system for detecting position and orientation of catheter tip. Sensors and Actuators. 2004; Issue A 111; pp. 304-309.

* cited by examiner $$\begin{bmatrix} B_x \\ B_y \\ B_z \end{bmatrix} = \begin{bmatrix} 1 & 0 & 0 \\ 0 & 1 & 0 \\ 0 & 0 & 1 \end{bmatrix} \begin{bmatrix} V_{lx} \\ V_{ly} \\ V_{lz} \end{bmatrix}$$

Fig. 13D $$\begin{bmatrix} B_x \\ B_y \\ B_z \end{bmatrix} = \begin{bmatrix} C_{11} & C_{12} & C_{13} \\ C_{21} & C_{22} & C_{23} \\ C_{31} & C_{32} & C_{33} \end{bmatrix} \begin{bmatrix} I_1 \\ I_2 \\ I_3 \end{bmatrix}$$

Fig. 13E $$\begin{bmatrix} B_x \\ B_y \\ B_z \end{bmatrix} = \begin{bmatrix} R_{11} & R_{12} & R_{13} \\ R_{21} & R_{22} & R_{23} \\ R_{31} & R_{32} & R_{33} \end{bmatrix} \begin{bmatrix} I_1 \\ I_2 \\ I_3 \end{bmatrix}$$

Fig. 13F $$\begin{bmatrix} B_x \\ B_y \\ B_z \end{bmatrix} = \begin{bmatrix} R_{11} & R_{12} & R_{13} \\ R_{21} & R_{22} & R_{23} \\ R_{31} & R_{32} & R_{33} \end{bmatrix} \begin{bmatrix} C_{11} & C_{12} & C_{13} \\ C_{21} & C_{22} & C_{23} \\ C_{31} & C_{32} & C_{33} \end{bmatrix} \begin{bmatrix} V_{lx} \\ V_{ly} \\ V_{lz} \end{bmatrix}$$

Fig. 13G

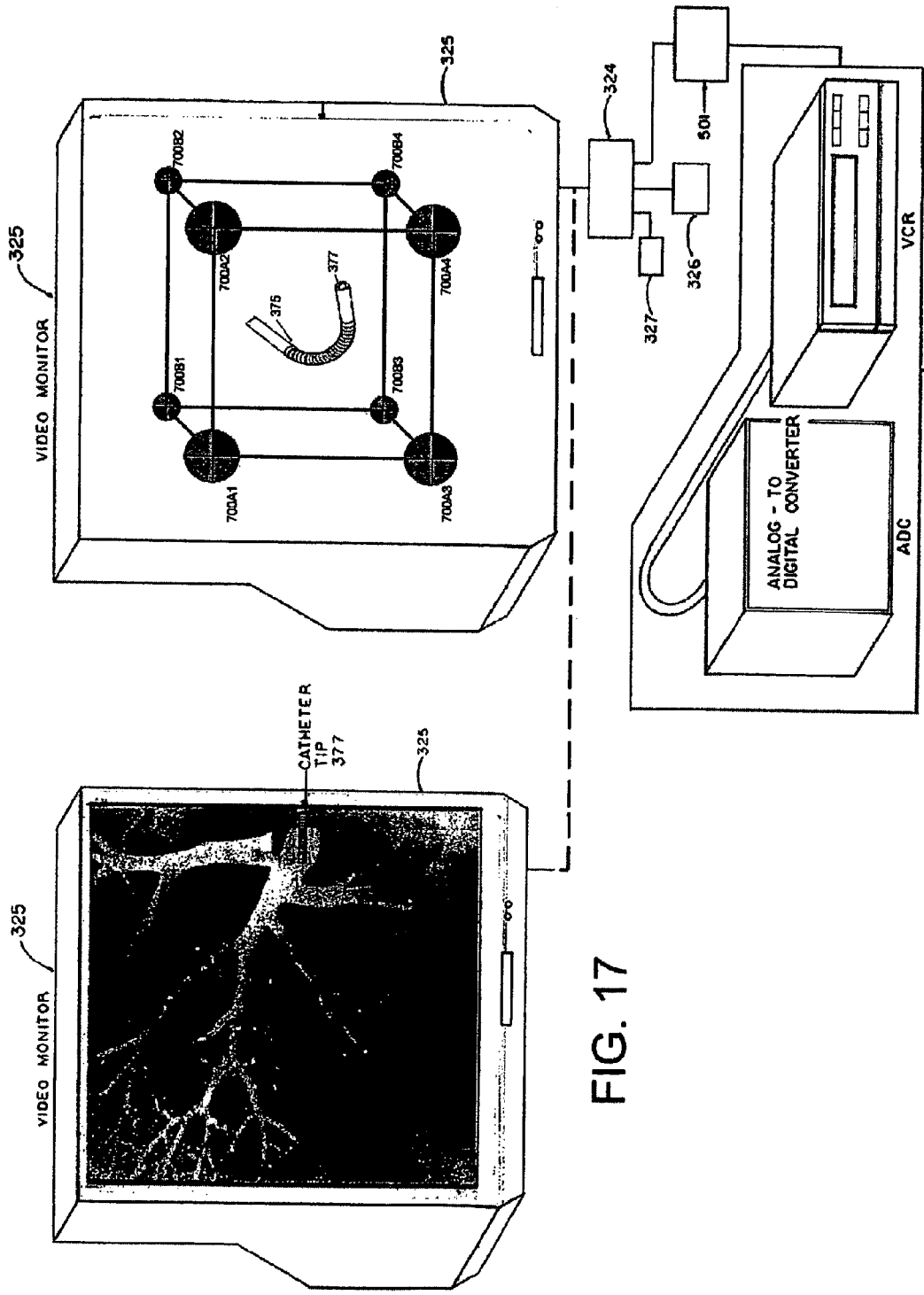

SYSTEM AND METHOD FOR A MAGNETIC CATHETER TIP

REFERENCE TO RELATED APPLICATIONS

The present application is a divisional of U.S. application Ser. No. 10/621,196 titled APPARATUS AND METHOD FOR A CATHETER GUIDANCE CONTROL AND IMAGING, which was filed Jul. 15, 2003 now U.S. Pat. No. 7,769,427 which claims priority from U.S. Provisional Patent Application No. 60/396,302, filed Jul. 16, 2002, titled "CATHETER GUIDANCE CONTROL AND IMAGING APPARATUS AND METHOD," the entire contents of which is hereby incorporated by reference.

BACKGROUND

1. Field of the Invention

The present invention relates to systems and techniques for guiding, steering, and advancing invasive medical devices such as catheters and catheter-type devices.

2. Description of the Related Art

In general, catheterization is performed by inserting an invasive device into an incision or a body orifice. Secondary tools such as guidewires and balloons are often advanced along the primary catheter to the area where the medical procedure is to be performed. These procedures rely on manually advancing the distal end of the invasive device by pushing, rotating, or otherwise manipulating the proximal end that remains outside of the body. Real-time x-ray imaging is a common method for determining the position of the distal end of the invasive device during the procedure. The manipulation continues until the distal end reaches the destination area where the diagnostic or therapeutic procedure is to be performed. This technique requires great skills on the part of the operator that can only be achieved after a protracted training period and extended practice. A high degree of manual dexterity is also required.

For example, angioplasty involves advancing a balloon catheter over a previously placed guidewire into a narrowed arterial section. Once properly positioned in the narrowed arterial section, the balloon is inflated and dilates this section. The time consuming technical difficulties encountered during angioplasty procedure are similar to those associated with angiography. If the artery to be treated is torturous with sharp bends, it may be difficult to advance the guidewire to the stenosis. If the stenosis is severe or the artery is totally blocked, it may be difficult or even impossible to properly position the guidewire. Alternatively, if the guidewire is successfully positioned in tight, hard plaque, the balloon catheter, being of a necessarily larger diameter than the guidewire, may encounter sufficient resistance to cause the guiding catheter to disengage from the ostium. This eliminates the support required to facilitate balloon advancement. These technical difficulties can render the procedure unfeasible.

Because of the difficulty involved in advancing a catheter into a desired location in the body, many diagnostic and therapeutic procedures employ a guidewire. The guidewire is first advanced into the heart or the artery and serves as a track and guide for a specific catheter. This technique is used to advance a catheter into the left ventricle and is especially important when studying aortic stenosis. Crossing the narrowed valve orifice is a challenge to the operator. Similarly, a guidewire is often manipulated into a blocked coronary artery and across the obstructive plaque. A therapeutic catheter, for example carrying a balloon, a laser, a stent, etc., is advanced over the guidewire, and placed at the site of the plaque. The narrowed site is then opened by inflating a balloon, operating a laser beam, or placing a stent. On occasions, the artery is torturous and severely narrowed and the plaque is irregular, calcified, or even totally occluding the artery. In these situations the placement of a guidewire beyond the narrowed site is very difficult and many times unsuccessful.

In some procedures, a catheter is used to cut through the intra-atrial septum in order to create a shunt (in transposition of the great vessels), to treat the mitral valve (mitral valvuloplasty), or to monitor directly the pressure in the left atrium.

The implantation of cardiac pacemakers is often essential for the survival of patients with heart rhythm or electrical conduction disturbances. This procedure is performed by the implantation of a small electrode in the heart cavity wall (ventricle or atrium). The other end of the electrode is attached to an electronic device which is implanted under the chest skin and that generates stimulation pulses to simulate the heart rhythm. Similar devices apply electrical shock when life-threatening heart electrical disturbances are detected by the electrodes (e.g., an Automatic Implantable Cardiac Defibrillator (AICD)). These electrodes are placed through a vein by pushing and manipulating under x-ray. Many times, the manipulation to place the electrodes in a proper position is difficult and the results are sub-optimal due to anatomical variations.

During electrophysiological study, electrical signals occurring in the myocardium (heart muscle) are measured and recorded. This is accomplished by advancing an electrode-carrying catheter into the heart. The catheter is manipulated until the electrode touches the endocardial region of interest. This can be a cumbersome and time-consuming procedure because multiple measurements are often required to perform a complete study. In addition, accurately positioning the electrode using manual manipulation is a difficult process.

Ablation of electrical pathways to eliminate heart rhythm disturbances eliminates potentially life threatening abnormal heart rhythms by ablating erroneous electrical pathways in the myocardium, that have been previously identified during an electrophysiological study. Ablation of these pathways using thermal or microwave energy delivered to a predetermined specific region by an energy-carrying catheter is the mainstay of the procedure. This catheter is placed in good contact with the selected endiocardial region, otherwise no ablation will occur. Additionally, the catheter must be precisely positioned in order to avoid damaging the normal electrical pathways. Given these exacting requirements, the imprecise nature of manual manipulation can cause this procedure to be especially difficult and time consuming.

Mitral valvuloplasty is used to treat mitral valve stenosis by dilating the narrowed valve with a balloon. The current method involves advancing a catheter through the vena cava into the right atrium. An incision is made in the intra-atrial septum and the catheter is forced through the cut into the left atrium. A balloon is then advanced through the catheter into the mitral valve apparatus, and inflated to break the stenotic tissue. Notwithstanding a high success rate and a low risk of recurrent restenosis associated with this procedure, a known complication is an atrial septal defect induced by the puncture of the intra-atrial septum. Although much less aggressive than surgery, this procedure is lengthy, difficult, and requires special skills in addition to those normally requisite for catheterization.

Mitral valvuloplasty (aorta to left atrium method) is considered by some to be a preferred alternative to the vena cava approach because the intra-artrial septum puncture is eliminated, thereby eliminating the potential complication of atrial septal defect. This procedure differs from the current method of mitral valvuloplasty in that the catheter is advanced through the aorta, the left atrium, and the aortic valve, for positioning into the left ventricle. A balloon is then advanced through the catheter into the mitral valve apparatus and inflated to break the stenotic tissue. Because a relatively rigid balloon is required to break the tissue narrowing the mitral valve, it is almost impossible to bring the balloon into proper alignment via the aorta and left ventricle due to the sharp acute angle between the aortic route and the required approach to the mitral valve.

Myocardial revascularization is a therapeutic procedure that increases the blood supply to the heart muscle by inducing the formation of new small blood vessels in the myocardium. The surgery involves opening the chest wall and laser "drilling" multiple small channels from the heart external aspect (epicardium).

Percutaneous myocardial revascularization is a catheter-based procedure for promoting angioneogensis. It involves advancing a laser catheter into the heart and performing the channelling from the heart inner aspect (endocardium). This approach is particularly applicable to patients who constitute a high surgical risk and who are beyond conventional catheter based therapy. Due to the accuracy required when positioning and fixating the laser catheter, this procedure does not appear to be implementable with currently available catheter technology.

The foregoing procedures suffer from numerous disadvantages and limitations. A very high skill level is often required to properly manipulate the catheter into position. Extensive training is required to attain this skill level. Many of the procedures are tedious and time-consuming. This results in repeated and prolonged exposure of the patient and staff to the adverse effects of x-rays. The lengthy procedures also require the use of additional contrast material with associated risk to the patient. Procedures that require highly-accurate positioning of the catheter distal end (also referred to as the catheter tip) are difficult to perform and are not always feasible. The insertion, removal, and manipulation of secondary tools often causes the tip of the guiding catheter to be dislodged from the desired position. Time-consuming manipulation is required to correctly reposition the tip. The coronary arteries are sometimes torturous with sharp bends or blockages that make advancement of a guidewire or balloon difficult or even impossible. A principal source of catheter tip location information is the x-ray imaging system with its associated adverse side effects.

Therefore, there is a great and still unsatisfied need for an apparatus and method for guiding, steering, and advancing invasive devices and for accurately controlling their position; for providing three dimensional imaging; and for minimizing the use of x-rays or other ionizing-type radiation

SUMMARY

The present invention solves these and other problems by providing a magnetic catheter guidance and control apparatus that requires less training and less skill that prior art systems. The magnetic catheter guidance system can rapidly advance and position the catheter, thus minimizing x-ray and contrast material exposure. Moreover, the magnetic system used in the magnetic catheter guidance system can be used to locate the catheter tip to provide location feedback to the operator and the control system.

One embodiment includes a catheter and a guidance and control apparatus that can accurately, and with relative ease, allow the surgeon/operator to position the catheter tip inside a patient's body. The catheter guidance and control apparatus can maintain the catheter tip in the correct position. One embodiment, includes a catheter with guidance and control apparatus that can steer a guidewire or balloon through arteries and forcefully advance it through plaque or other obstructions. One embodiment includes a catheter guidance and control apparatus that displays the catheter tip location with significantly reduced x-ray exposure to the patient and staff. One embodiment includes a catheter guidance and control apparatus that is more intuitive and simpler to use, that displays the catheter tip location in three dimensions, that applies force at the catheter tip to pull, push, turn, or hold the tip as desired, and that is capable of producing a vibratory or pulsating motion of the tip with adjustable frequency and amplitude to aid in advancing the tip through plaque or other obstructions. One embodiment provides tactile feedback at the operator control to indicate an obstruction encountered by the tip.

In one embodiment, a catheter Guidance Control and Imaging (GCI) apparatus allows a surgeon to advance, accurately position and fixate a catheter, and to view the catheters' position in three dimensions with the x-ray imagery overlaying the display. In one embodiment, the apparatus includes an operator control called a "Virtual Tip" which, in addition to being a model representation of the actual or physical catheter tip advancing within the patient's body, possesses a positional relationship to the catheter tip.

The Virtual Tip includes a physical assembly, somewhat akin to a joystick, that can be manipulated by the surgeon and is also designed to deliver tactile feedback to the surgeon in the appropriate axis or axes if the actual tip encounters an obstacle. In other words, the Virtual Tip includes a joystick-type device that allows the surgeon to guide the actual catheter tip though the patient's body. Then the actual catheter tip encounters an obstacle, the Virtual Tip provides tactile force feedback to the surgeon to indicate the presence of the obstacle.

In one embodiment, the physical catheter tip (the distal end of the catheter) includes a permanent magnet that responds to a magnetic field generated externally to the patient's body. The external magnetic field pulls, pushes, turns, and holds the tip in the desired position. One of ordinary skill in the art will recognize that the permanent magnet can be replaced or augmented by an electromagnet.

The operator control provides the position and orientation command inputs to a servo system that controls the catheter tip position by regulating the magnetic force applied outside the patient's body. A measurement of the actual tip position and orientation is made via sensory apparatus that includes magnetic field sensors and temperature sensors. This measurement serves as a feedback to the servo system and the operator interface. In one embodiment, the servo system has a correction input that compensates for the dynamic position of a body part or organ, such as the heart, thereby offsetting the response such that the actual tip moves in unison with the beating heart.

The operation of the catheter guidance system is as follows: i) the operator adjusts the physical position of the virtual catheter tip, ii) a change in the virtual tip position is encoded producing input data received at a control system, iii) the control system generates commands sent to servo system control apparatus, iv) the servo system control apparatus operates the servo mechanisms to adjust the electromagnetic field of external magnets, which v) causes the position of the actual magnetic catheter tip within the patient's body to change, vi) the new position of the actual catheter tip is then sensed by magnetic field sensors and temperature sensor arrays, which vii) provide feedback to the servo system control apparatus and the monitoring system of the operator interface thereby updating the displayed image of the actual catheter tip position in relation to the overlaid patient x-ray image.

The operator can then make further adjustments to the virtual catheter tip position and the sequence of steps ii through vii are repeated in a way that is smooth and continuous to the user. In addition, throughout this procedure, feedback from the servo system control apparatus creates command logic when the actual catheter tip encounters an obstacle or resistance in its path. The command logic is used to control stepper motors physically coupled to the virtual catheter tip. The stepper motors are engaged to create resistance in the appropriate direction(s) that can be felt by the operator, and tactile feedback is thus provided to the surgeon.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items.

FIG. 13D is a matrix representation of a vector FIG. 13E is a representation of the characteristic matrix FIG. 13F is a representation of the Inverse characteristic matrix FIG. 13G is a representation of the product of the characteristic matrix with its Inverse matrix

FIG. 17 illustrates the use of the apparatus of FIG. 1B with cineangiographic equipment.

FIG. 17A illustrates the use of fiduciary markers synchronizing the fluoroscopy image.

DETAILED DESCRIPTION

Figure 1A:
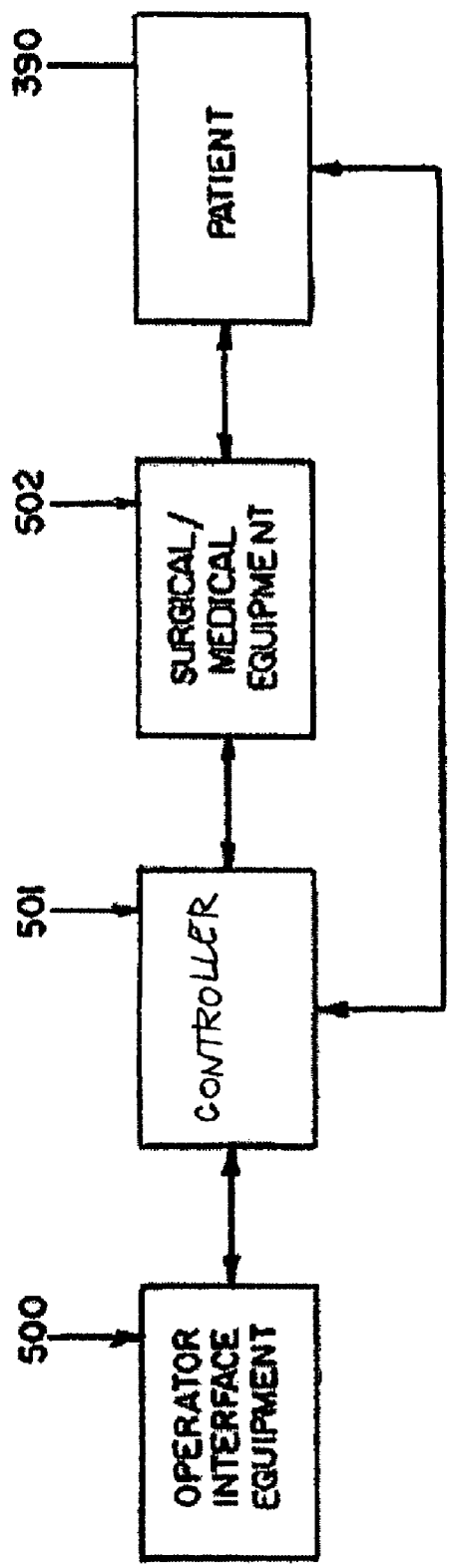
FIG. 1A is a high-level system block diagram for a surgery system that includes an operator interface, a catheter guidance system, surgical equipment (e.g., a catheter to be guided), and a patient.
Figure 1B:
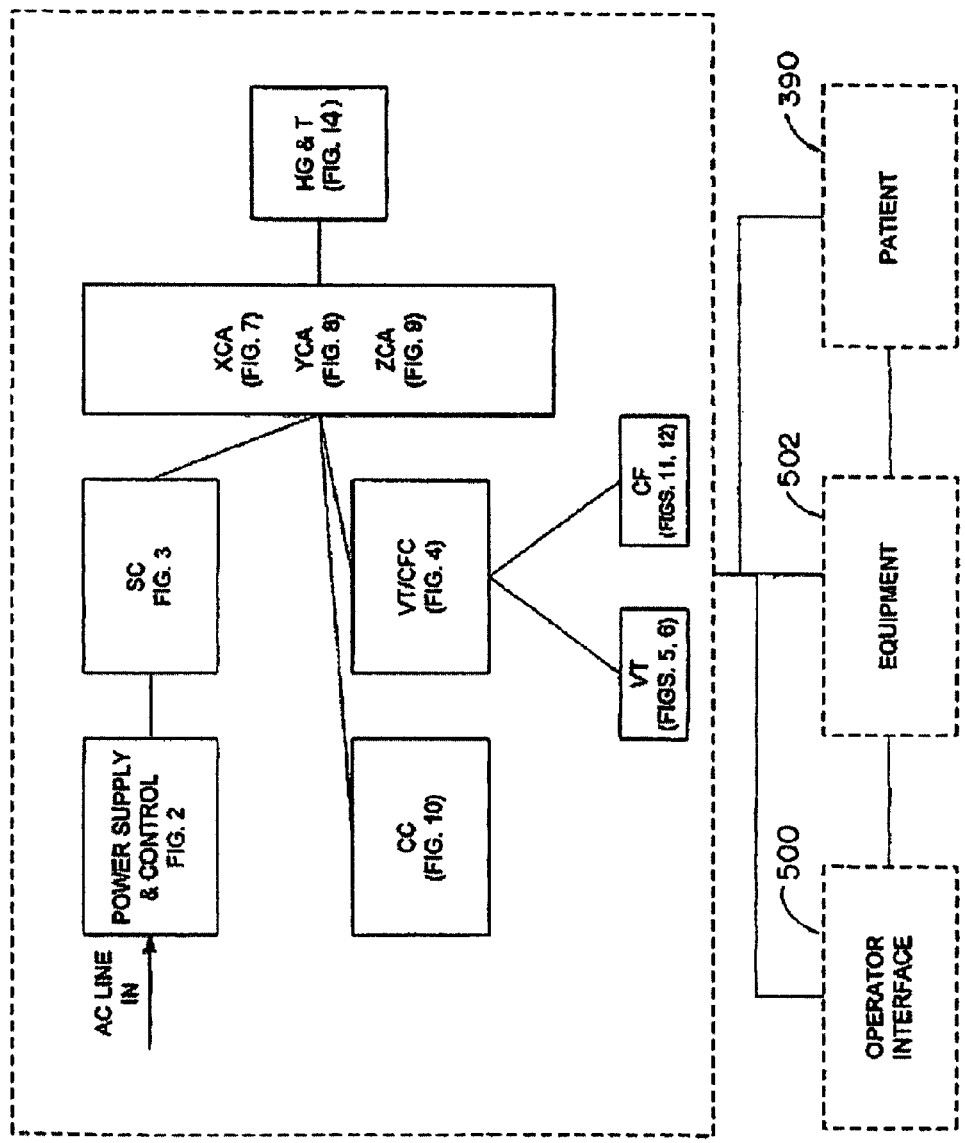
FIG. 1B is a block diagram of one embodiment of the catheter guidance system from FIG. 1A.

FIGS. 1A, 1B and 1C show a system 700 that includes a guidance, control, and imaging (GCI) apparatus 501. The system 700 further includes an operator interface equipment 500 and a surgical medical equipment 502. FIG. 1A illustrates an embodiment of the GCI apparatus 501 that includes various functional units. FIG. 1A further illustrates the overall relationship between these functional units and the operator interface 500, the auxiliary equipment 502 residing in the operating room, and the patient 390. FIG. 1B provides further details of the inter-relationships of these functional units and some of their components.

FIG. 1C shows the inter-relation between the GCI apparatus 501, surgical medical equipment 502, operator interface equipment 500, and a reference patient 390. A more detailed description of the GCI apparatus 501 and other auxiliary equipment, such as the surgical medical equipment 502, in the operating room will be described later in greater detail in connection with FIGS. 16, 16A, 16B and 16C. The system 700 is configured to guide a catheter or similar device having a distal end (also referred to herein as a tip) that enters the body.

Figure 2:
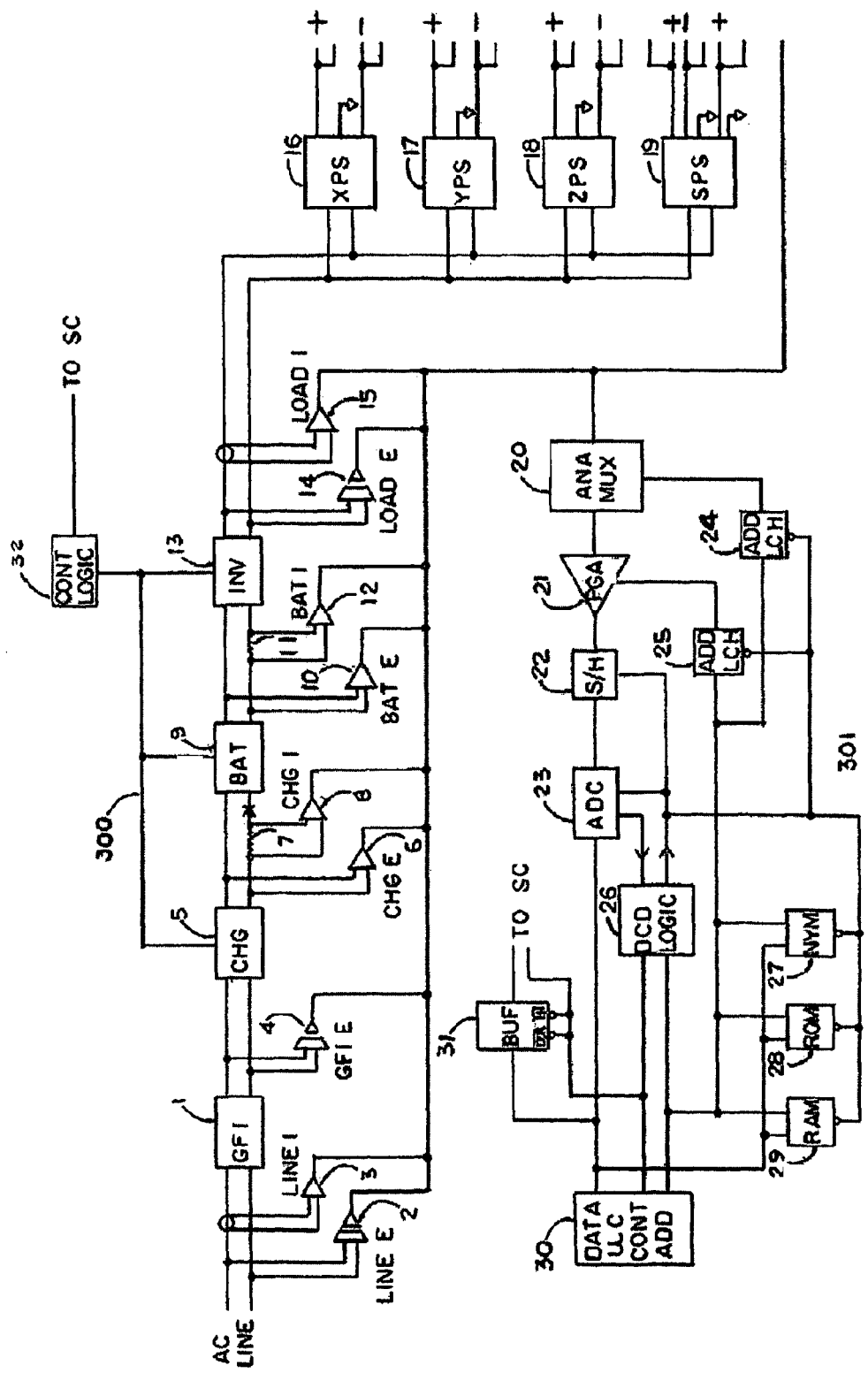
FIG. 2 is a schematic diagram of a ground fault interrupter, an uninterruptable power supply, DC supplies, and a supervisory unit for use in the apparatus of FIG. 1B.

FIG. 2 is a block diagram that illustrates a first functional unit of GCI apparatus 501, namely a power supply and control unit that includes a ground fault interrupter 1, an uninterruptable power supply 300, DC supplies 16, 17, 18, and 19, and a supervisory unit 301 for use in the system 700 of FIG. 1B.

Figure 3:
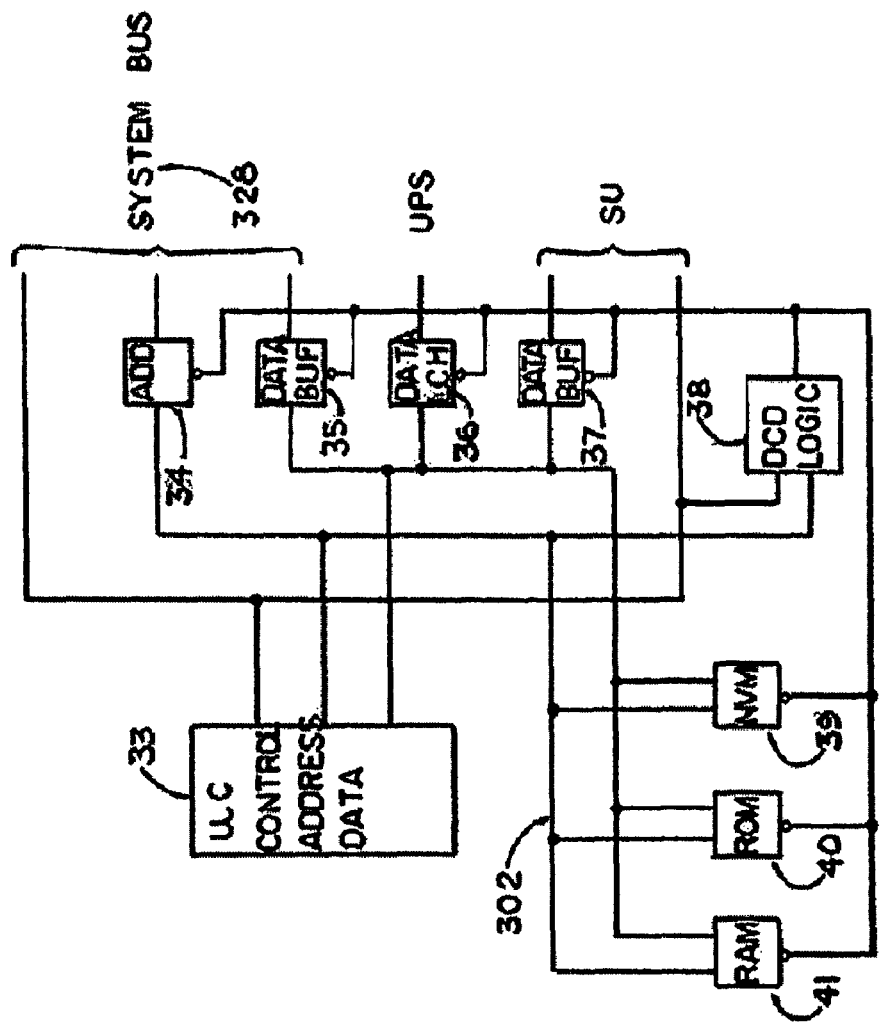
FIG. 3 is a schematic diagram of a system controller for use in the apparatus of FIG. 1B.
Figure 4:
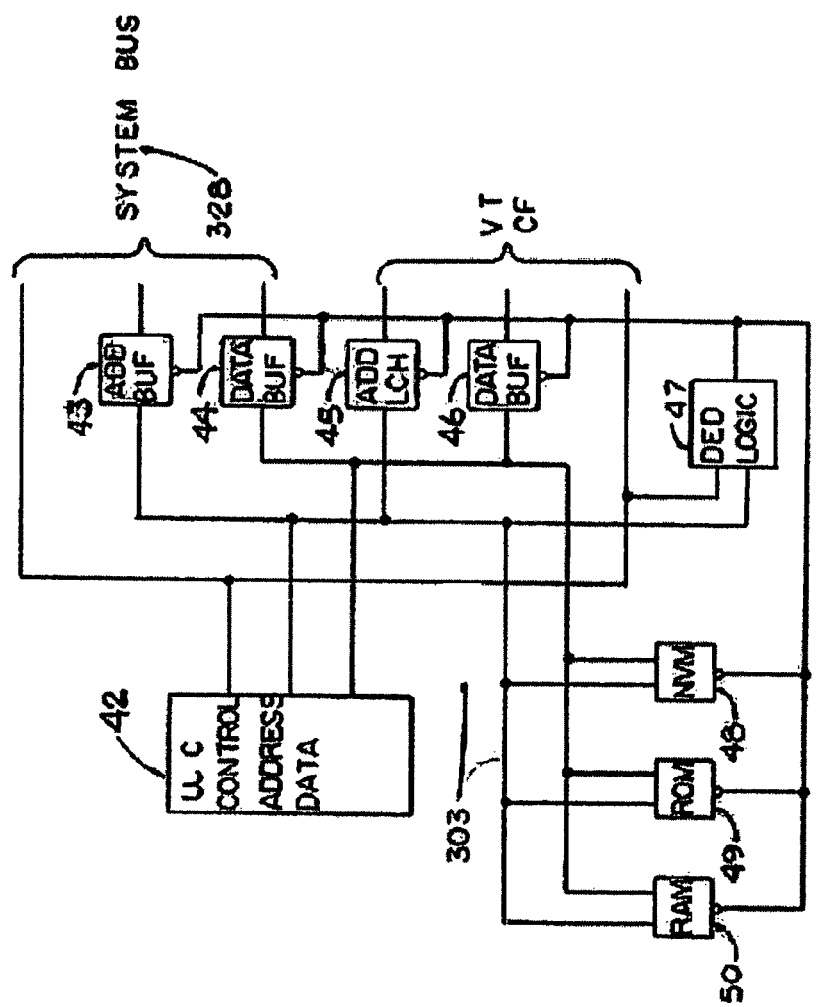
FIG. 4 is a schematic diagram of a virtual tip and calibration fixture controller for use in the apparatus of FIG. 1B.
Figure 5:
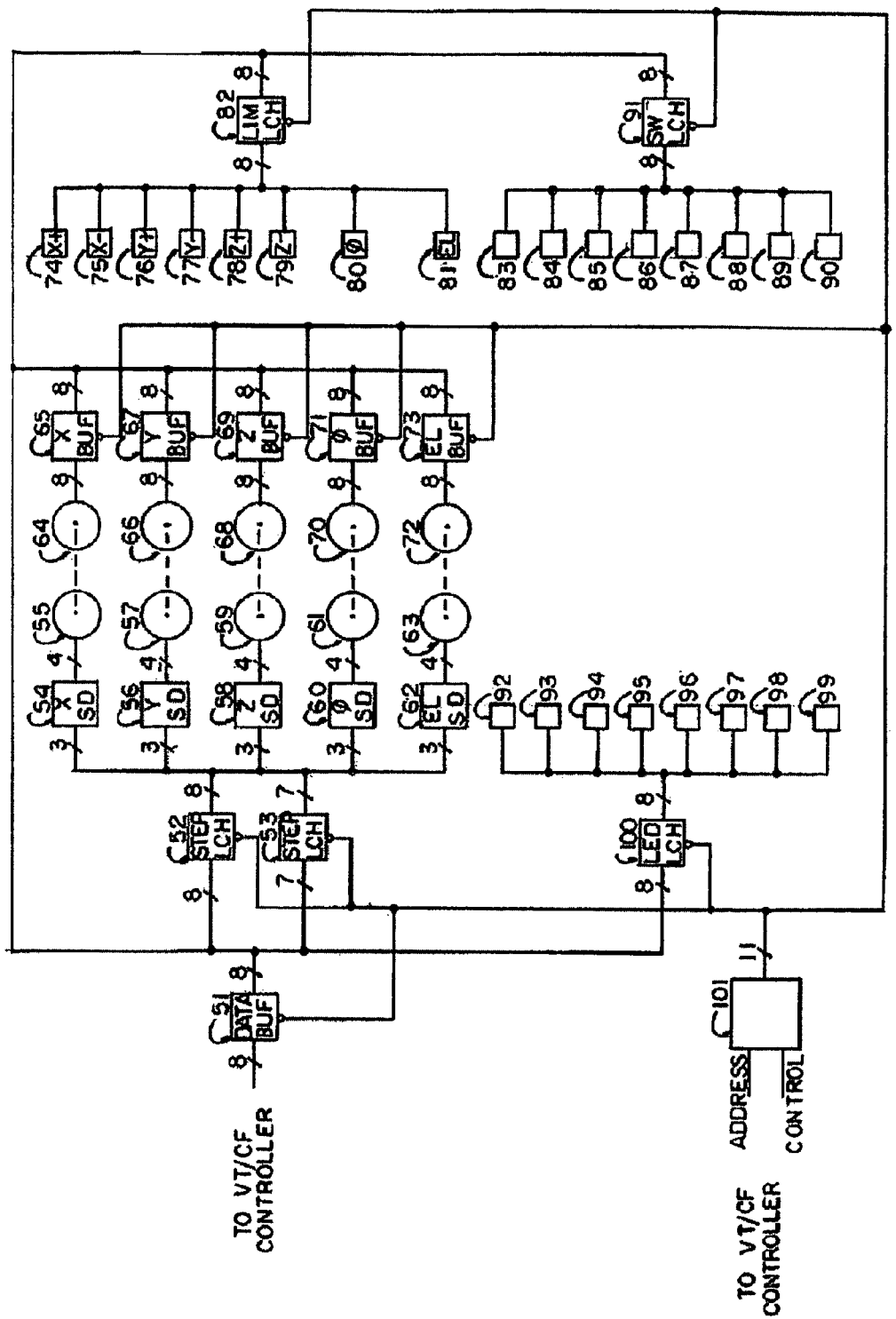
FIG. 5 is an electrical block diagram of a virtual tip for use in the apparatus of FIG. 1B.
Figure 6:
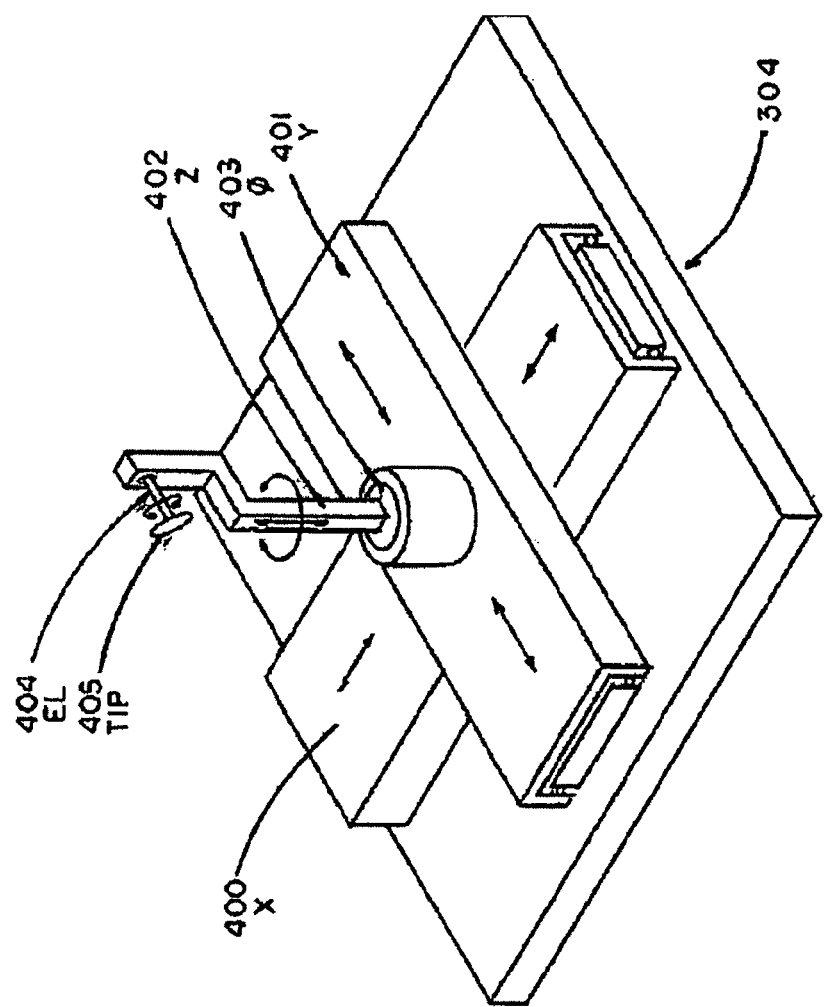
FIG. 6 is a perspective view of the Virtual Tip device in connection with the electrical block diagram of FIG. 5.
Figure 14:
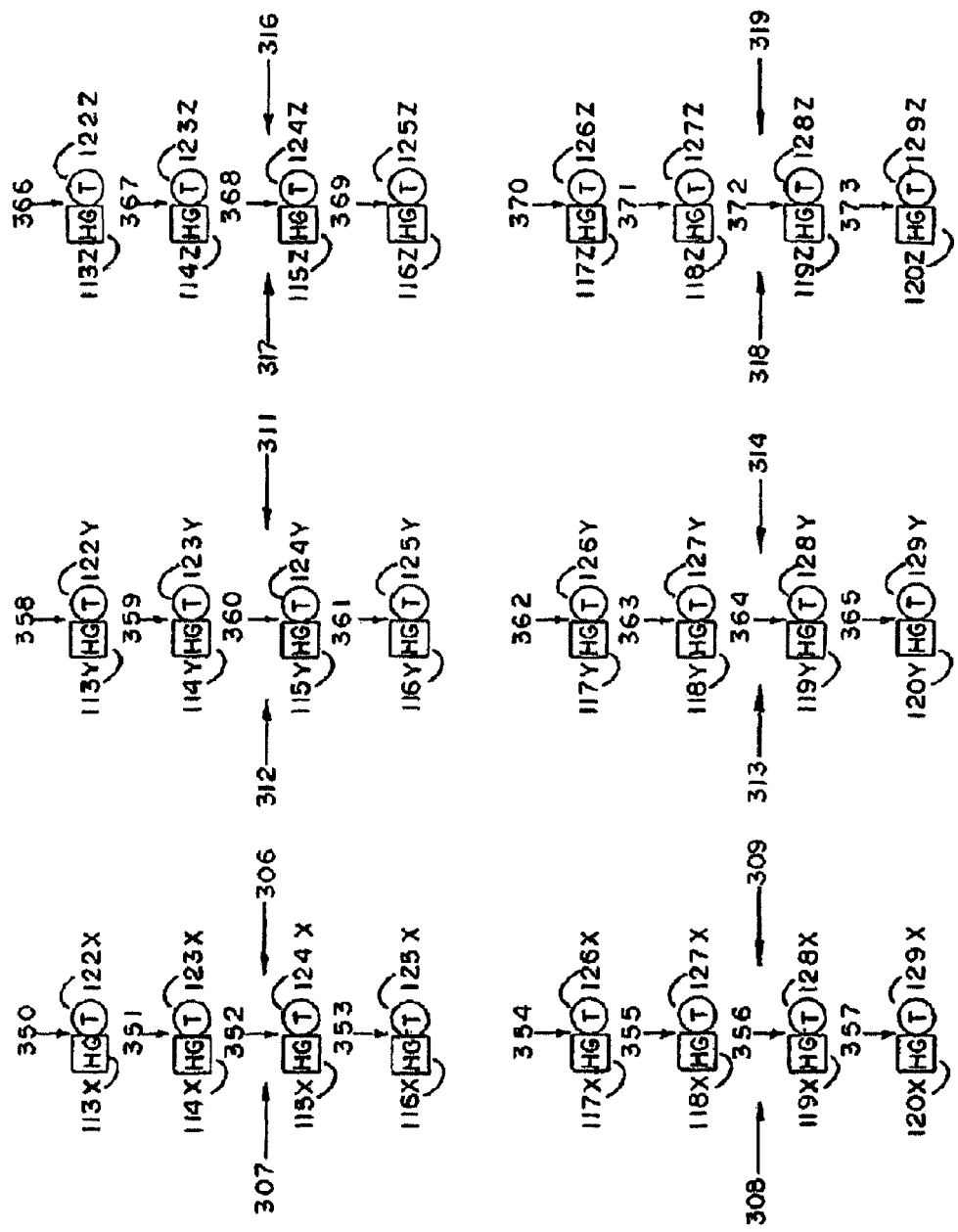
FIG. 14 illustrates various magnetic field sensors and temperature sensor pairs for use in the apparatus of FIG. 1B.

Another functional unit of the GCI apparatus 501 is a system controller (SC) 302 which is illustrated in FIG. 3. Yet another functional unit of the GCI apparatus 501 is a virtual tip and calibration fixture controller (VT/CFC) 303 which is illustrated in FIG. 4. Still another functional unit of the GCI apparatus 501 is a virtual tip assembly (VT) 304 which is illustrated in FIGS. 5 and 6. Additional functional units of the GCI apparatus 501 include an X-Axis controller and amplifier (XCA) 305, a Y-Axis controller and amplifier (YCA) 310, and a Z-Axis controller and amplifier (ZCA) 315. These functional units are each individually detailed by functional block diagrams in FIGS. 7, 8, and 9, respectively. Still other functional units of the GCI apparatus 501 include a communication controller (CC) 320 which is depicted in detail in FIG. 10; a calibration fixture (CF) 321 which is depicted in detail in FIGS. 11 and 12; and magnetic field sensor (MFS) and temperature sensor (TS) pairs 374 that are illustrated in FIG. 14. The various magnetic field sensors and temperature sensor pairs 374 are used in the system 700 of FIG. 1B. The magnetic field sensor or sensors can be Hall-effect sensors, superconducting sensors, or other sensors that sense a magnetic field such as, for example, the magnetic field produced by a magnet (or electromagnet) at the distal end of the catheter. In one embodiment, the magnetic field sensors are Hall-effect sensors. The temperature sensors can be thermistors or other temperature-sensing devices. The temperature sensors are described herein because many magnetic field sensing devices, such as, for example, Hall-effect sensors are temperature-dependent. However, the temperature sensors are optional and can be omitted when the additional accuracy afforded by the temperature sensors is not needed or when knowledge of the temperature of the magnetic sensors is not needed.

Referring to FIG. 1B, the power supply and control system 392 includes: a Ground Fault Interrupter (GFI) 1; an uninterruptable power supply (UPS) 300; a supervisory unit (SU) 301; individual DC power supplies XPS 16, YPS 17, and ZPS 18 that provide power to the X Axis Controller And Amplifier (XCA) 305, the Y-axis Controller And Amplifier (YCA) 310, and the Z-axis Controller And Amplifier (ZCA) 315, respectively; and a DC system power supply (SPS) 19 that provides the DC power needed to operate other digital and analog circuitry of the GCI apparatus 501. These components and their functional relationships are depicted in greater detail in FIG. 2.

Referring now to FIG. 2, the Ground Fault Interrupter (GFI) 1 acts as a safety device by monitoring the AC input current in the line and the neutral. If an imbalance is detected, it is assumed that a stray path to ground is present (posing a shock hazard to the user or the patient). This detection will cause a trip that disconnects the load from the line.

The uninterruptable power supply (UPS) 300 contains batteries 9, a charging system 5, an inverter 13, and power switching circuitry. The UPS 300 automatically supplies the entire AC power requirements of the system 700 for the duration of a power failure, or until battery depletion occurs. A graceful system shutdown is initiated by a Supervisory Unit (SU) 301 and a system controller (SC) 302 if the power failure extends beyond battery capacity.

Still referring to FIG. 2, an amplifier 3 and its current transformer monitor the AC line current. An isolation amplifier 4 monitors the AC voltage output of Ground Fault Interrupter (GFI) 1. Charger 5 produces the desired DC power to charge battery 9 of the uninterruptable power supply 300. An amplifier 8 monitors the voltage drop across shunt 7 to determine the charge current of the battery 9. An amplifier 10 monitors the output voltage of the battery 9. An amplifier 12 monitors the voltage drop across shunt 11 to determine load current of the battery 9. An inverter 13 generates the AC power used by components of the GCI apparatus 501. An isolation amplifier 14 monitors the AC output voltage of inverter 13. An amplifier 15 and its current transformer monitor the current output of inverter 13.

A Supervisory Unit (SU) 301 monitors the signals from the following components: the AC line; and the outputs of the Ground Fault Interrupter (GFI) 1, the uninterruptable power supply (UPS) 300; and the DC power supplies 16, 17, 18, and 19. The Supervisory Unit (SU) 301 informs the System Controller (SC) 302 of an AC power failure, a Ground Fault Interrupter (GFI) trip, an Uninterruptable Power Supply (UPS) failure or failure of the DC power supplies 16, 17, 18, and 19.

As detailed in FIG. 2, the SU 301 includes an analog multiplexer 20 that connects a given signal to be monitored to a programmable gain amplifier 21. A decode logic 26 in conjunction with an address latch 24 allow a microcontroller 30 to set the input channel of the analog multiplexer 20. A microcontroller 30 executes a code resident in read only memory 28. The decode logic 26 in conjunction with address latch 25 allow microcontroller 30 to set the gain of programmable gain amplifier 21. Microcontroller 30 then strobes sample and hold circuit 22 via decode logic 26. The output of sample and hold circuit 22 is thus a "snapshot" of the signal to be measured.

Analog to digital converter 23 is issued a convert command by microcontroller 30 via decode logic 26. When conversion is complete, analog to digital converter 23 interrupts microcontroller 30 via decode logic 26 and the digital representation of the measured signal is input by microcontroller 30. A random access memory 29 is used to store sampled data during operation of the SU 301. A non-volatile memory 27 stores data during power down. It is by this method that the various voltages and currents are monitored by supervisory unit 301. Microcontroller 30 communicates with system controller 302 via buffer 31. Control logic 32 allows system controller 302 to coordinate the power up-power down sequence in accordance with system conditions.

With reference to FIGS. 1B and 3, System Controller (SC) 302 controls the power up-power down sequence in an orderly fashion and alerts the operator to the system status and any required corrective action via Communications Controller (CC) 320, Computer 324, and monitor 325. In addition, System Controller (SC) 302 coordinates the operation of X Axis Controller and Amplifier (XCA) 305, Y-Axis Controller and Amplifier (YCA) 310, and Z Axis Controller and Amplifier (ZCA) 315. Additionally, System Controller (SC) 302 communicates with Virtual Tip/Calibration Fixture Controller (VT/CFC) 321 and Communication Controller (CC) 320 via system bus 328.

As illustrated in FIG. 1B, Servo Power Supply (XPS) 16 provides DC power to the X-Axis Controller and Amplifier (XCA) 305. The XCA 305 energizes the electromagnets 132X and 138X that are located outside the patient's body. X Axis Controller and Amplifier (XCA) 305 monitors temperature sensor (TS) arrays 306, 309, and magnetic field sensor arrays 307, 308, and further drives Electromagnet (EM) 132X and 138X. Magnetic field sensor arrays 307 and 308 measure the magnetic flux in the X axis. Temperature sensor (TS) arrays 306 and 309 measure the temperature of magnetic field sensor arrays 307 and 308 so that X Axis Controller and Amplifier (XCA) 305 can apply temperature compensation factors to the magnetic field sensor outputs.

The sensory outputs of these arrays 306, 307, 308, 309 provide feedback to XCA 305 concerning the position of the actual catheter tip 377 with reference to the X-axis. As it will become apparent from the present description, these electromagnets 132X and 138X affect the position of the actual catheter tip 377 inside the patient's body 390 in the X-axis.

Servo Power Supply (YPS) 17 provides DC power to the Y-Axis Controller and Amplifier (YCA) 310 for energizing the electromagnets (EM) 132Y and 138Y that are located outside the patient's body. YCA 310 monitors the sensor arrays of the Y-axis that include temperature sensor (TS) arrays 311, 314, and magnetic field sensor array 312, 313. Magnetic field sensor arrays 312 and 313 measure the magnetic flux in the Y-axis. Temperature sensor (TS) arrays 311 and 314 measure the temperature of magnetic field sensor arrays 312 and 313 so that Y Axis Controller and Amplifier (YCA) 310 can apply temperature compensation factors to the magnetic field sensor outputs. The sensory outputs of these arrays 311, 312, 313, 314 provide feedback to the servo system controlled by YCA 310 concerning the position of the actual catheter tip 377 with reference to the Y-axis. As it will become apparent from the present description, these electromagnets 132Y and 138Y affect the position of the actual catheter tip 377 inside the patient's body 390 in the Y-axis.

The Z-Axis Power Supply (ZPS) 18 provides DC power to the Z-Axis Controller and Amplifier (ZCA) 315 for energizing the electromagnets (EM) 132Z and 138Z that are located outside the patient's body. ZCA 315 monitors the sensor arrays of the Z-axis that include the following components: temperature sensor (TS) arrays 316, 318, and magnetic field sensor arrays 317, 319. Magnetic field sensor arrays 317 and 319 measure the magnetic flux in the Z axis. Temperature sensor (TS) arrays 316 and 318 measure the temperature of magnetic field sensor arrays 317 and 319, so that Z Axis Controller and Amplifier (ZCA) 315 can apply temperature compensation factors to the magnetic field sensor outputs. The sensory outputs of these arrays 316, 317, 318, 319 provide feedback to the servo system controlled by ZCA 315 concerning the position of the actual catheter tip 377 with reference to the Z-axis. As it will become apparent from the present description, these electromagnets 132Z and 138Z affect the position of the actual catheter tip 377 inside the patient's body 390 in the Z-axis.

Communication Controller (CC) 320 interfaces host system 323, auxiliary equipment 322, and the computer 324 to system bus 328. The surgical and medical equipment 502 can include, for example, the host system 323 and auxiliary equipment 322. The host system 323 contains data concerning the patient and the current procedure(s) and also archives data generated by the GCI apparatus 501. Auxiliary equipment 322 can include the x-ray imaging system and other patient monitoring apparatus.

The operator interface 500 includes, for example, Computer 324, monitor 325, keyboard 326, and mouse 327. The computer 324 allows the operator to adjust the system parameters and to perform calibration and diagnostic routines. Monitor 325 displays the actual catheter tip 377 position data with overlaid X-ray imagery and operator prompts. Keyboard 326 and mouse 327 are used for operator-entered data input.

Virtual Tip/Calibration Fixture Controller (VT/CFC) 303 inputs encoder position, limit switch, and operator switch data from Virtual Tip assembly 304 to be used by XCA 305, YCA 310, and ZCA 315 in controlling the electromagnets 132X, 138X, 132Y, 138Y, 132Z, and 138Z. Also, Virtual Tip/Calibration Fixture Controller (VT/CFC) 303 outputs Tactile Feedback (TF) response and light emitting diode (LED) data to Virtual Tip (VT) 304 to be perceived by the operator as obstructions or resistance met by the actual catheter tip 377.

FIG. 3 illustrates the components of one embodiment of the system controller (SC) 302. A detailed description of the functionality of these components will follow in the ensuing description of the drawings. SC 302 can be characterized as functioning in different modes: 1) a power-up/power-down mode, 2) a servo system controller mode, 3) a tactile feedback response mode, and 4) a calibration mode.

In the power-up/power down mode, SC 302 coordinates power-up/power-down sequencing of the components of the GCI apparatus 501, performs built-in system diagnostic functions, and reports any errors detected during diagnostic functions which are sent to the communications controller (CC) 320 and stored in memory 41. These tasks are accomplished by microcontroller 33. Error data is stored in Random Access Memory (RAM) 41 during system operation and in Non Volatile Memory (NVM) 39 during power down. Microcontroller 33 communicates with other system components via system bus 328 by setting the appropriate address and control bits to decode logic 38 that enables address buffer 34 and data buffer 35. Data latch 36 and data buffer 37 similarly connect microcontroller 33 to Uninterruptable Power Supply (UPS) 300 and to supervisory unit (SU) 301 via control logic 32.

Figure 23:
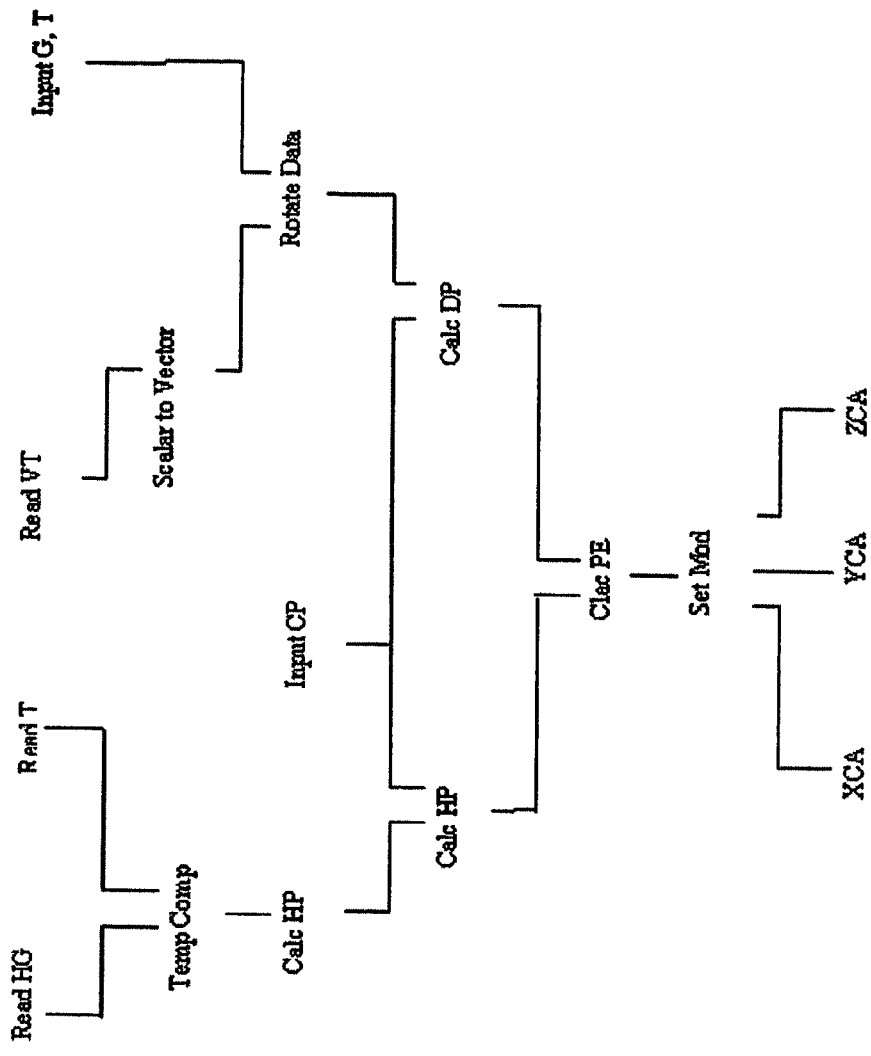
FIG. 23 is a logical flow diagram of a controller forming part of the apparatus of FIG. 1B, for determining the position of the actual tip of FIG. 18A in response to a new move command.

In the servo system controller mode, System Controller (SC) 302 calculates the actual tip (AT) position as further described in conjunction with FIG. 23. Then, using data from the virtual tip (VT) 405, determines the appropriate position error, that is the difference between the actual tip position and the operator-desired tip position as indicated by the virtual tip position, to be sent to X Axis Controller and amplifier (XCA) 305, Y-Axis Controller and amplifier (YCA) 310, and Z-Axis Controller and amplifier (ZCA) 315 via the system bus 328.

In the tactile feedback response mode, System Controller SC 302 initiates tactile feedback response by providing feedback data to the virtual tip (VT) 304 via the system bus 328, as described in detail in FIG. 23.

During the calibration mode, System Controller (SC) 302 exercises Calibration Fixture (CF) 312 via Virtual Tip/Calibration Fixture controller (VT/CFC) 303 and correlates the position data from X-axis Controller and Amplifier (XCA) 305, Y-axis Controller and Amplifier (YCA) 310, and Z-axis Controller and Amplifier (ZCA) 305 with Calibration Fixture (CF) 321 encoders 64C, 66C, 68C, 70C, and 72C.

FIG. 4 illustrates the Virtual Tip And Calibration Fixture Controller (VT/CF) 303. Data is stored in Random Access Memory (RAM) 50 during the system operation and in a Non Volatile Memory (NVM) 48 during power down. Microcontroller 42 communicates with System Controller (SC) 302 (FIG. 3) via system bus 328 by setting the appropriate address and control bits to decode logic 47, which enables address buffer 43 and data buffer 44. Address latch 45 and data buffer 46 similarly connect microcontroller 42 with virtual tip (VT) 405 or calibration fixture (CF) 321, as described below.

Virtual Tip/Calibration Fixture (VT/CF) controller 303 inputs data from VT 304 or CF 321 concerning the encoder positions, limit "switch" closures, and operator input switch positions. Additionally, Virtual Tip/Calibration Fixture (VT/CF) controller 303 outputs data to Virtual Tip (VT) 304 to produce tactile feedback and to illuminate the LED indicators to alert the operator of various system conditions.

Referring to FIG. 5, the electronic circuitry function of the VT assembly 304 is as follows. A decode logic 101 responds to address and control bits originating from Virtual Tip/Calibration Fixture controller (VT/CFC) 303 (FIG. 3), enabling data buffer 51 and setting its direction for transferring data. Step latches 52 and 53 store incoming data sent from the VT/CFC 303 to be presented to stepper drivers 54, 56, 58, 60 and 62 when strobed by decode logic 101. Stepper motors 55, 57, 59, 61, and 63 respond to the stepper driver outputs to provide tactile feedback to the operator. The stepper motors 55, 57, 59, 61, and 63 create tactile feedback by producing resistance in the appropriate axial or angular coordinates as follows: stepper motor 55 in the X-axis 400; stepper motor 57 in the Y-axis 401, stepper motor 59 in the Z-axis 402; stepper motor 61 in the angular direction of θ; and stepper motor 63 in the angular direction of EL.

Still referring to FIG. 5, the absolute encoders 64, 66, 68, 70, and 72 are mechanically coupled to the corresponding stepper motors 55, 57, 59, 61, and 63, and provide position feedback to the VT/CFC 303 during Tactile Feedback (TF) as well as inform the VT/CFC 303 of the Virtual Tip (VT) position during manual adjustments of the VT 405 by the operator. Encoder outputs are buffered by 65, 67, 69, 71, and 73, to temporarily store and transfer axial and angular position information to VT/CFC 303. Limit "switches" 74, 75, 76, 77, 78, and 79 flag the ends of the three linear axes, in order to limit the mechanical motion of the virtual tip 405, and to allow synchronization of the mechanics of the virtual tip assembly 304 and the electronics of FIG. 5. "Switches" 80 and 81 indicate when angular θ and EL are at zero position, for synchronizing of the mechanics of the virtual tip assembly 304 and the electronics shown in FIG. 5. Latch 82 strobes decode logic 101 in order to store these data defining positional limits. Operator switches 83, 84, 85, 86, 87, 88, 89, and 90 are read and latched by latch 91, in order to store their command, since these switches are momentary (i.e., momentary contact as opposed to a stable switch position). LEDs 92, 93, 94, 95, 96, 97, 98, and 99 are driven by LED latch 100.

Figure 7:
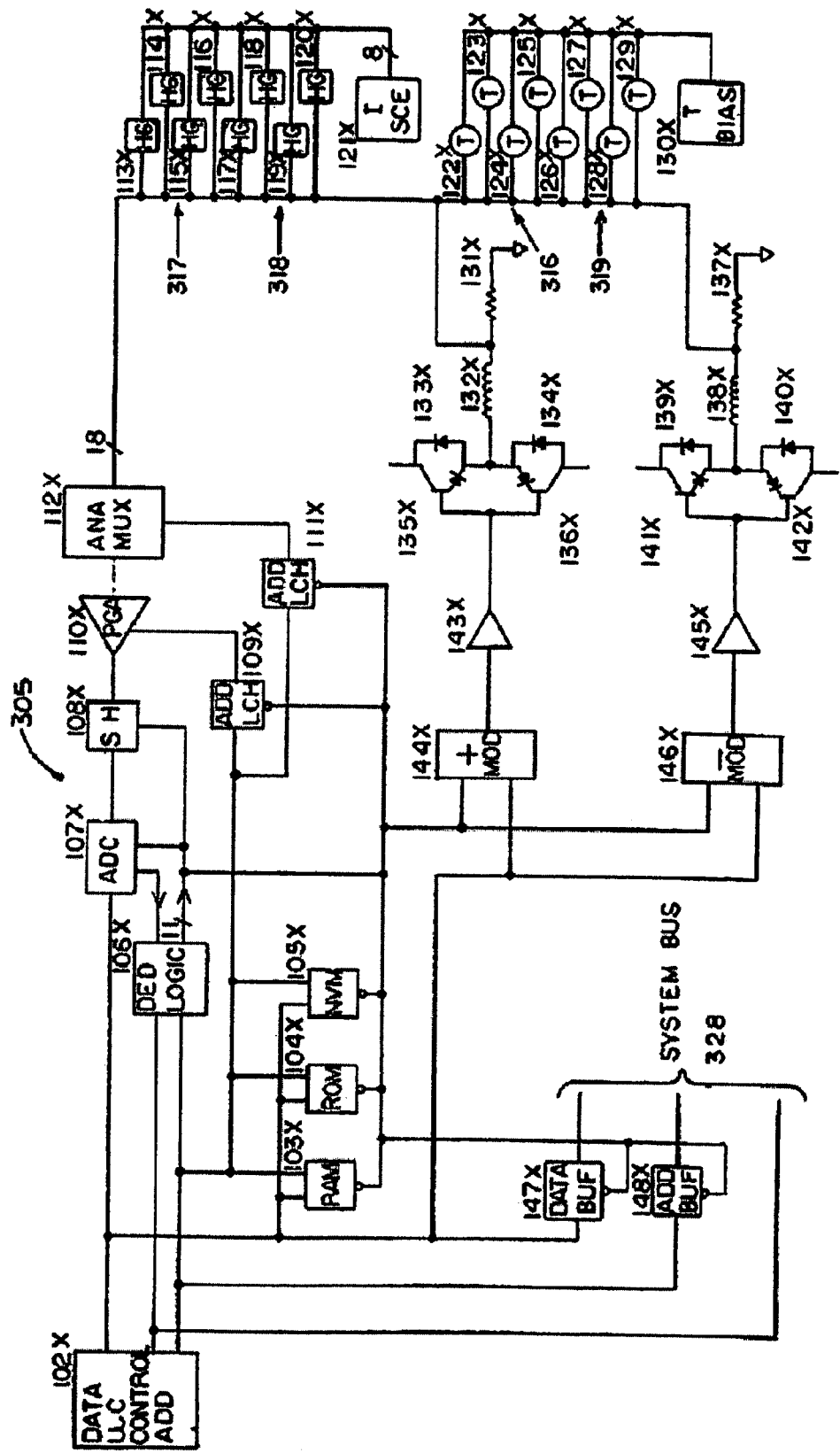
FIG. 7 is a schematic diagram of an X axis controller and amplifier for use in the apparatus of FIG. 1B.

FIG. 7 illustrates the X axis controller and amplifier (XCA) 305. XCA 305 receives and amplifies signals in the form of sensory data from the x-axis magnetic field sensors sensor arrays 307 and 308 and temperature sensor arrays 306 and 309. Using this sensory data, a code is executed in microcontroller 102X to create positional feedback to the VT/CFC 303 and other system components via system bus 328. Microcontroller 102X also receives data from VT/CFC 303 and other system components via system bus 328 to use in generating commands that will control the excitation of the external electromagnets 132X and 138X to affect the position of the actual catheter tip in the X-axis. XCA 305 also generates error and correcting signals to be used during the calibration and normal system operation. These functions will now be described.

First, the method by which XCA 305 monitors the sensory data from the MFS arrays 307 and 308 and temperature sensor arrays 306 and 309 will be explained. Magnetic field sensors sensor array 307 includes magnetic field sensors 113$x$, 114$x$, 115$x$ and 116$x$. Magnetic field sensors sensor array 308 includes magnetic field sensors 117$x$, 118$x$, 119$x$, and 120$x$. Temperature sensor array 306 includes temperature sensors 122$x$, 123$x$, 124$x$, and 125$x$. Temperature sensor array 309 includes temperature sensors 126$x$, 127$x$, 128$x$, and 129$x$. The physical positions of these sensors and relations to one another are described in conjunction with FIG. 13. Microcontroller 102$x$ executes a mathematical procedure that is described in conjunction with FIGS. 18, 18A, 18B and 18C, that calculates positional data based on input from the sensor arrays 307 and 308. Input and output data is stored in Random Access Memory (RAM) 103$x$ during system operation. Non Volatile Memory (NVM) 105$x$ stores data such as temperature compensation parameters which are used in combination with measured temperature sensor array 306 and 309 data to make necessary corrections to data from the magnetic field sensors 113X, 114X, 115X, 116X, 117X, 118X, 119X, and 120X.

The collecting of sensory data is initiated by decode logic 106$x$ in conjunction with address latch 111$x$ that allows microcontroller 102$x$ to set the input channel of analog multiplexer 112$x$. Similarly, decode logic 106$x$ in conjunction with address latch 109$x$ allows microcontroller 102$x$ to set the gain of programmable gain amplifier 110$x$ in order to compensate for variations in signal strength from the sensor arrays 307, 308, 306, and 309. Microcontroller 102$x$ strobes sample and hold circuit 108$x$ via decode logic 106$x$, so that microcontroller 102$x$ is able to perform other functions while periodically sampling the data temporarily stored in sample and hold circuit 108$x$. The output of sample and hold circuit 108$x$ is thus a "snapshot" of the signal to be measured.

Analog-to-Digital Converter (ADC) 107$x$ is issued a "convert" command by microcontroller 102$x$ via decode logic 106$x$ to convert the data from the position sensors 307 and 308 from analog to digital, so that the digital system can interpret the data. When the conversion is complete, analog to digital converter 107$x$ interrupts microcontroller 102$x$ via decode logic 106$x$ and the digital representation of the measured signal is input by microcontroller 102$x$. It is by this method that the magnetic field sensors 113$x$, 114$x$, 115$x$, 116$x$, 117$x$, 118$x$, 119$x$, and 120$x$ as well as the temperature sensors 122$x$, 123$x$, 124$x$, 125$x$, 126$x$, 127$x$, 128$x$, and 129$x$ are monitored. Similarly, the voltage drop across the shunts 131X and 137X is measured to determine the current flow through the electromagnets 132X and 138X.

Still referring to FIG. 7, current source 121$x$ provides the control current to bias the magnetic field sensors 113X, 114X, 115X, 116X, 117X, 118X, 119X, and 120X. since they operate best in a constant current mode and require stability for reliable sensing. Temperature sensor bias supply 130$x$ supplies the voltage for the temperature sensors 122X, 123X, 124X, 125X, 126X, 127X, 128X, 129X.

The method by which XCA 305 generates commands to control the movement of the actual catheter tip 377 in the X-axis will now be explained. Microcontroller 102X receives data from VT/CFC 303 and other system components via system bus 328 to use in generating commands that will control the movement. Microcontroller 102$x$ in conjunction with decode logic 106$x$ controls modulators 144$x$ and 146$x$ to provide the correct move signal and command. Preamplifiers 143$x$, and 145$x$ amplify the modulators outputs and drive final amplifiers 135$x$, 136$x$, 141$x$, and 142$x$. Diodes 133$x$, 134$x$, 139$x$, and 140$x$ protect the final amplifiers from a surge of back electromotive force due to the inductive nature of the electromagnet coils 132$x$ and 138$x$.

Electromagnet coils 132$x$ and 138$x$ produce a magnetic field that affects the position of the actual catheter tip in the X-Axis.

Microcontroller 102X communicates with VT/CFC 303 and other system components via system bus 328 by setting the appropriate address and control bits to decode logic 106$x$, which enables address buffer 148$x$ and data buffer 147$x$.

Non Volatile Memory (NVM) 105x also stores calibration data to be used during calibration operations in conjunction with the calibration fixture 321 and VT/CFC 303. These operations and the source of the calibration data will be described later in conjunction with FIG. 23. Further, Non Volatile Memory (NVM) 105x stores error codes to be used during power down operations controlled by the System Controls (SC) 302.

Figure 8:
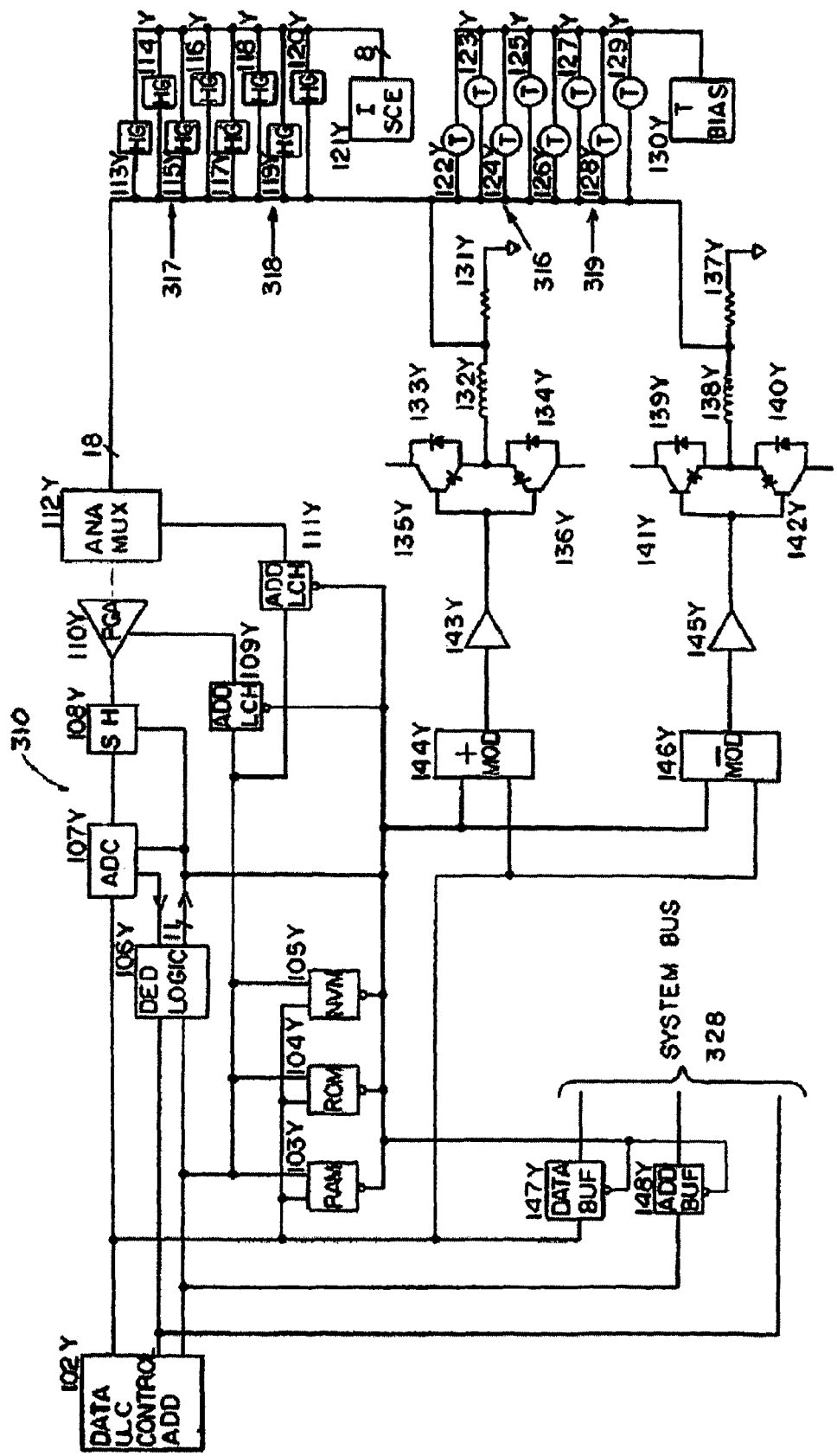
FIG. 8 is a schematic diagram of a Y axis controller and amplifier for use in the apparatus of FIG. 1B.

FIG. 8 illustrates The Y-axis controller and amplifier (YCA) 310 which operates in a similar manner to the XCA 305 of FIG. 7. YCA 310 receives and amplifies the signals from the Y-axis magnetic field sensor arrays 312 and 313 and temperature sensor arrays 311 and 314. Using this incoming sensory data, a code is executed in microcontroller 102Y to create positional feedback to the VT/CFC 303 and other system components via system bus 328. Microcontroller 102Y also receives data from VT/CFC 303 and other system components via system bus 328 to use in generating commands that will control excitation of the external electromagnets 132Y and 138Y to affect the position of the actual catheter tip 377 in the Y-axis. YCA 310 also generates error and correcting signals to be used during the calibration and normal system operation. These functions will now be described.

First, the method by which YCA 310 monitors the sensory data from MFS arrays 312 and 313 and temperature sensor arrays 311 and 314 will first be explained. Magnetic field sensor array 312 includes magnetic field sensors 113y, 114y, 115y and 116y. Magnetic field sensor array 313 includes magnetic field sensors 117y, 118y, 119y, and 120y. Temperature sensor array 311 includes temperature sensors 122y, 123y, 124y, and 125y. Temperature sensor array 314 includes temperature sensors 126y, 127y, 128y, and 129y. The physical positions of these sensors and relations to one another are described in conjunction with FIG. 13.

Microcontroller 102y executes a mathematical procedure, that described in conjunction with FIGS. 18, 18A, 18B and 18C, that calculates positional data based on input from the sensor arrays 312 and 313. Input and output data is stored in Random Access Memory (RAM) 103y during system operation. Non Volatile Memory (NVM) 105y stores data such as temperature compensation parameters which are used in combination with measured temperature sensor array 311 and 314 data to make necessary corrections to data from the magnetic field sensors 113Y, 114Y, 115Y, 116Y, 117Y, 118Y, 119Y, and 120Y. The collecting of sensory data is initiated by decode logic 106y in conjunction with address latch 111y, which allows microcontroller 102y to set the input channel of analog multiplexer 112y. Similarly, decode logic 106y in conjunction with address latch 109y allows microcontroller 102y to set the gain of programmable gain amplifier 110y, in order to compensate for variations in signal strength from the sensor arrays 311, 312, 313, and 314. Microcontroller 102y strobes sample and hold circuit 108y via decode logic 106y, to allow microcontroller 102y to perform other functions while periodically sampling the data temporarily stored in sample and hold circuit 108Y. The output of sample and hold circuit 108y is thus a "snapshot" of the signal to be measured.

Analog to Digital Converter (ADC) 107y is issued a convert command by microcontroller 102y via decode logic 106y to convert the data from the position sensors 312 and 313 from analog to digital, so that the digital system can interpret the data. When the conversion is complete, analog to digital converter 107y interrupts microcontroller 102y via decode logic 106y and the digital representation of the measured signal is input by microcontroller 102y. It is by this method that the magnetic field sensors 113y, 114y, 115y, 116y, 117y, 118y, 119y, and 120y as well as the temperature sensors 122y, 123y, 124y, 125y, 126y, 127y, 128y, and 129y are monitored. Similarly, the voltage drop across the shunts 131Y and 137Y is measured to determine the current flow through the electromagnets 132Y and 138Y.

Still referring to FIG. 8, current source 121y provides the control current to bias the magnetic field sensors 113Y, 114Y 115Y, 116Y, 117Y, 118Y, 119Y, and 120Y, since they operate best in a constant current mode and require stability for reliable sensing. Temperature sensor bias supply 130y supplies the voltage for the temperature sensors 122Y, 123Y, 124Y, 125Y, 126Y. 127Y, 128Y, and 129Y.

The method by which YCA 310 generates commands that will control the movement of the actual catheter tip in the Y-Axis will now be explained. Microcontroller 102Y receives data from VT/CFC 303 and other system components via system bus 328 to use in generating commands that will control the movement of the actual catheter tip in the Y-axis will now be explained. Microcontroller 102y in conjunction with decode logic 106y controls modulators 144y and 146y to provide the correct move signal and command. Preamplifiers 143y, and 145y amplify the modulators outputs and drive final amplifiers 135y, 136y, 141y, and 142y. Diodes 133y, 134y, 139y, and 140y protect the final amplifiers from a surge of back electromotive force due to the inductive nature of the electromagnet coils 132Y and 138Y. Electromagnet coils 132y and 138y produce the magnetic field which will affect the position of the actual catheter tip 377 in the Y-Axis.

Microcontroller 102Y communicates with VT/CFC 303 and other system components via system bus 328 by setting the appropriate address and control bits to decode logic 106y, which enables address buffer 148y and data buffer 147y.

Non Volatile Memory (NVM) 105y also stores calibration data to be used during calibration operations in conjunction with the calibration fixture 321 and VT/CFC 303. These operations and the source of the calibration data will be described later in conjunction with FIG. 23. Further, Non Volatile Memory (NVM) 105y stores error codes to be used during power down operations controlled by the System Controls (SC) 302.

Figure 9:
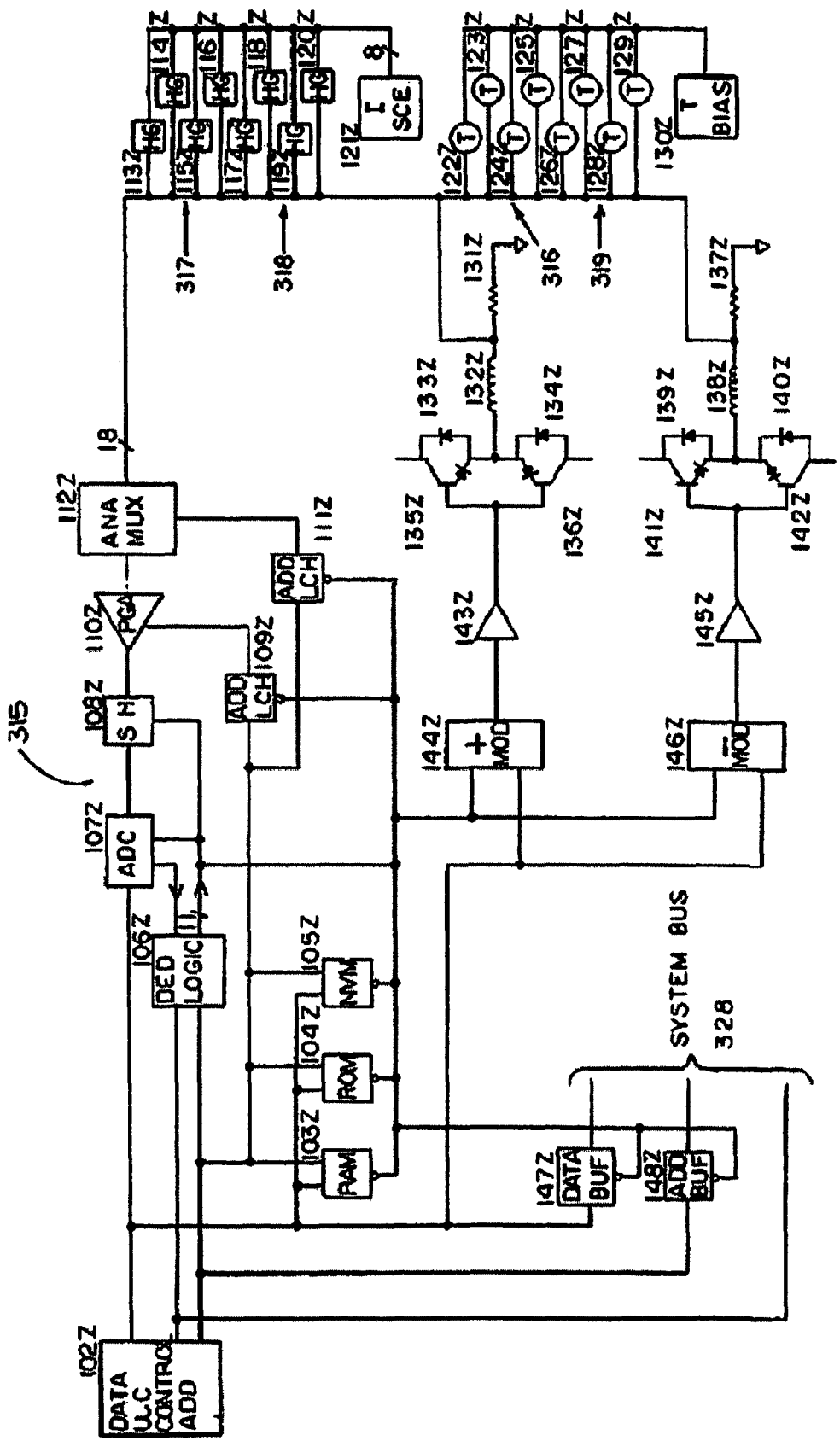
FIG. 9 is a schematic diagram of a Z axis controller and amplifier for use in the apparatus of FIG. 1B.

FIG. 9 illustrates the Z-axis controller and amplifier (ZCA) 315 which operates in a similar manner to that of FIGS. 7 and 8. ZCA 315 receives and amplifies the signals from the z-axis magnetic field sensor arrays 312 and 313 and temperature sensor arrays 311 and 314. Using the incoming sensory data, a code is executed in microcontroller 102Z to create positional feedback to the VT/CFC 303 and other system components via system bus 328. Microcontroller 102Z also receives data from VT/CFC 303 and other system components via system bus 328, to use in generating commands that will control the excitation of the external electromagnets 132Z and 138Z to affect the position of the actual catheter tip 337 in the Z-axis. ZCA 315 also generates error and correcting signals to be used during the calibration and normal system operation. These functions will now be described.

First, the method by which ZCA 315 monitors the sensory data from MFS arrays 317 and 318 and temperature sensor arrays 316 and 319 will first be explained. Magnetic field sensor array 317 includes magnetic field sensors 113z, 114z, 115z and 116z. Magnetic field sensor array 318 includes magnetic field sensors 117z, 118z, 119z, and 120z. Temperature sensor array 316 includes temperature sensors 122z, 123z, 124z, and 125z. Temperature sensor array 319 includes temperature sensors 126z, 127z, 128z, and 129z. The physical positions of these sensors and relation to one another are described in conjunction with FIG. 13.

Microcontroller 102z executes a mathematical procedure that is described in conjunction with FIGS. 18, 18A, 18B and 18C, and that calculates positional data based on input from the sensor arrays 317 and 318. Input and output data is stored in Random Access Memory (RAM) 103z during system operation. Non Volatile Memory (NVM) 105z stores data such as temperature compensation parameters that are used in combination with measured data from the temperature sensor arrays 316 and 319, to make necessary corrections to the data from the magnetic field sensors 113Z, 114Z, 115Z, 116Z, 117Z, 118Z, 119Z, and 120Z.

The collecting of sensory data is initiated by decode logic 106z in conjunction with address latch 111z that allows microcontroller 102z to set the input channel of analog multiplexer 112z. Similarly, decode logic 106z in conjunction with address latch 109z allows microcontroller 102z to set the gain of programmable gain amplifier 110z, in order to compensate for variations in signal strength from the sensor arrays 316, 317, 318, and 319.

Microcontroller 102z strobes sample and hold circuit 108z via decode logic 106z, to allow microcontroller 102z to perform other functions while periodically sampling the data temporarily stored in sample and hold circuit 108Z. The output of sample and hold circuit 108z is thus a "snapshot" of the signal to be measured. Analog to Digital Converter (ADC) 107z is issued a convert command by microcontroller 102z via decode logic 106z, to convert the data from the position sensors 317 and 318 from analog to digital, so that the digital system can interpret the data. When the conversion is complete, analog to digital converter 107z interrupts microcontroller 102z via decode logic 106z and the digital representation of the measured signal is input by microcontroller 102z. It is by this method that the magnetic field sensors 113z, 114z, 115z, 116z, 117z, 118z, 119z, and 120z as well as the temperature sensors 122z, 123z, 124z, 125z, 126z, 127z, 128z, and 129z are monitored. Similarly, the voltage drop across the shunts 131Z and 137Z is measured to determine the current flow through the electromagnets 132Z and 138Z.

Still referring to FIG. 9, current source 121z provides the control current to bias the magnetic field sensors 113Z, 114Z, 115Z, 116Z, 117Z, 118Z, 119Z, and 120Z since they operate best in a constant current mode, and require stability for reliable sensing. Temperature sensor bias supply 130z supplies the voltage for the temperature sensors 112Z, 123Z, 124Z 125Z, 126Z, 127Z, 128Z, and 129Z.

The method by which ZCA 315 generates commands that will control the movement of the actual catheter tip in the Z-axis will now be explained. Microcontroller 102Z receives data from VT/CFC 303 and other system components via system bus 328, to use in generating commands that will control the movement of the actual catheter tip in the Z-axis will now be explained. Microcontroller 102z in conjunction with decode logic 106z controls modulators 144z and 146z to provide the correct move signal and command. Preamplifiers 143z, and 145z amplify the modulators outputs and drive final amplifiers 135z, 136z, 141z, and 142z. Diodes 133z, 134z, 139z, and 140z protect the final amplifiers from a surge of back electromotive force due to the inductive nature of the electromagnet coils 132Z and 138Z. Electromagnet coils 132z and 138z produce the magnetic field which will affect the position of the actual catheter tip in the Z-axis.

Microcontroller 102Z communicates with VT/CFC 303 and other system components via system bus 328 by setting the appropriate address and control bits to decode logic 106z, which enables address buffer 148z and data buffer 147z.

Non Volatile Memory (NVM) 105z also stores calibration data to be used during calibration operations in conjunction with the calibration fixture 321 and VT/CFC 303. These operations and the source of the calibration data will be described later in conjunction with FIG. 23. Further, Non Volatile Memory (NVM) 105z stores error codes to be used during power down operations controlled by the System Controls (SC) 302.

Figure 10:
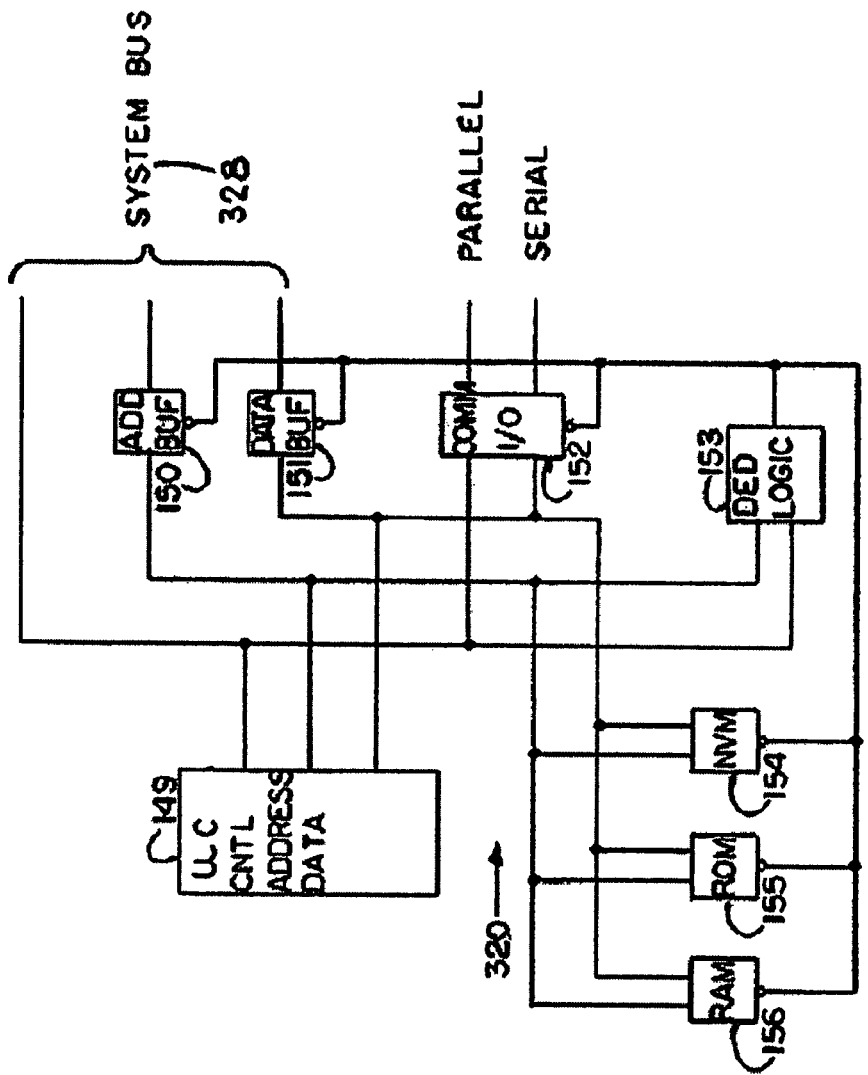
FIG. 10 is a schematic diagram of a communication controller for use in the apparatus of FIG. 1B.

FIG. 10 illustrates the communication controller (CC) 320 whose main function is to communicate with other system components via system bus 328. The position data received from the XCA 305, YCA 310, and ZCA 315 is stored in Random Access Memory (RAM) 156 during system operation and in Non Volatile Memory (NVM) 154 during power down, in order to retain the position of the actual tip inside the patient's body. Microcontroller 149 communicates with other system components via system bus 328, by setting the appropriate address and control bits to decode logic 153, which enables address buffer 150 and data buffer 151. Similarly, microcontroller 149 communicates with PC 324, auxiliary equipment 322, and host system 323 via communication I/O port 152, by setting address and control bits to decode logic 153 or responding to an interrupt from port 152. This is done for a number of reasons, such as the need to display the actual process and procedure of the operation on a CRT display.

Figure 11:
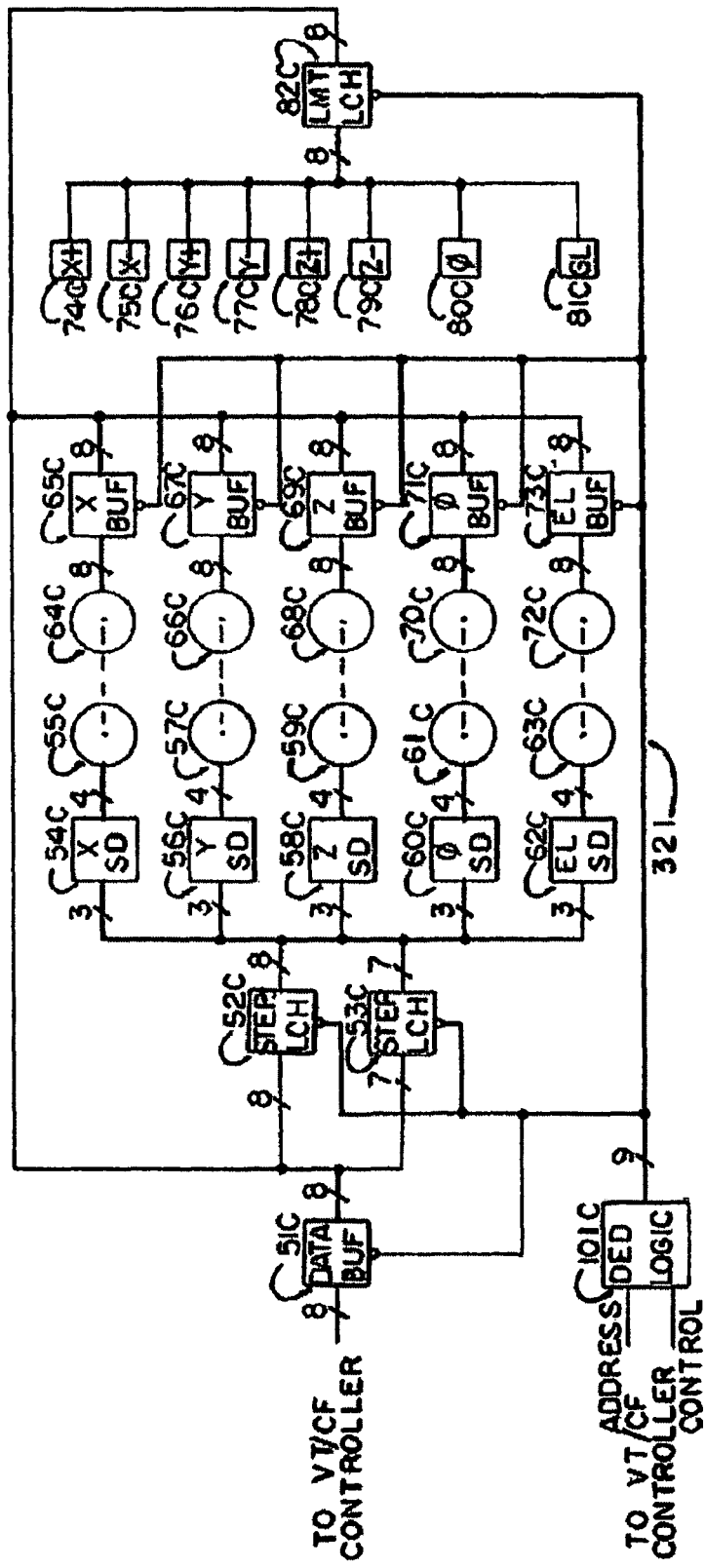
FIG. 11 is a schematic diagram of a calibration fixture for use in the apparatus of FIG. 1B.
Figure 12:
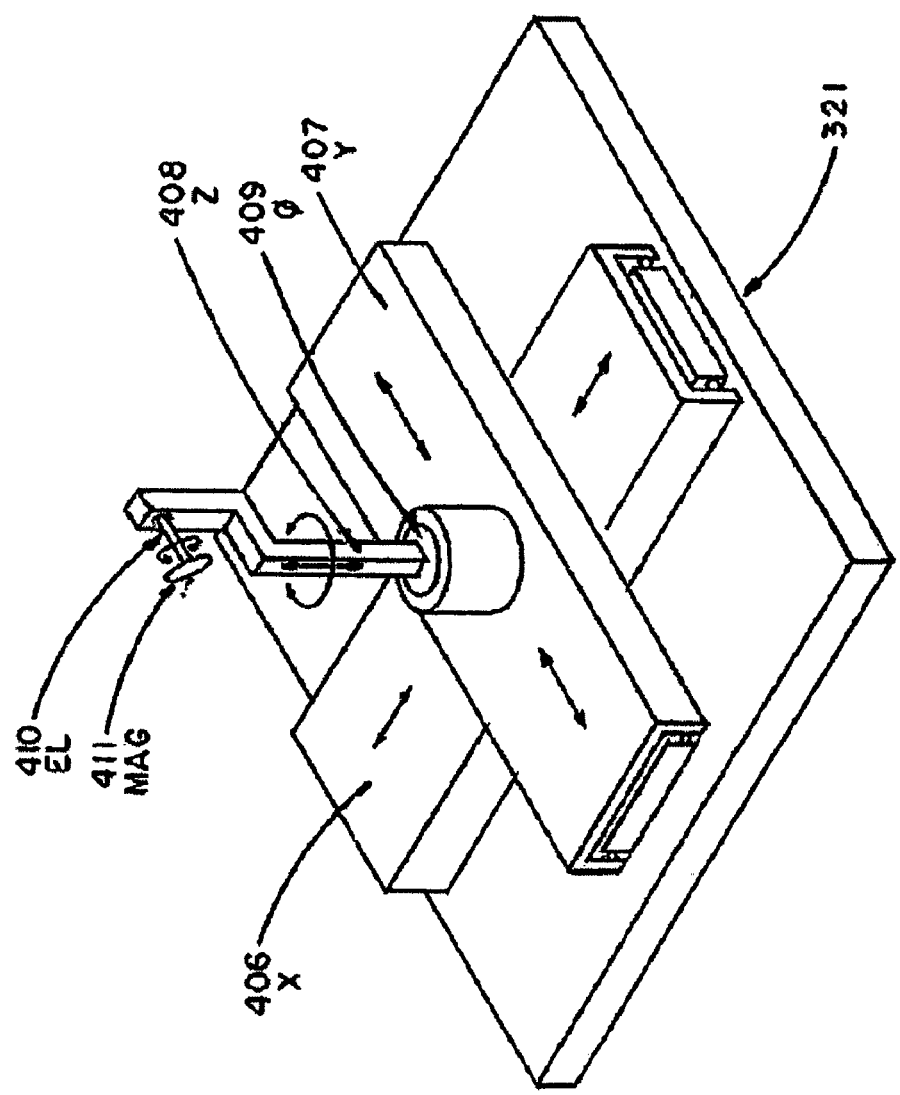
FIG. 12 is a perspective view of the calibration fixture (mechanical) of FIG. 11.

FIG. 11 illustrates the electrical circuitry of the calibration fixture (CF) 321 and FIG. 12 illustrates the mechanical implementation of the calibration fixture (CF) 321. The purpose of the CF, 321, is to define the steps and limits of motion in each possible direction of the virtual tip 405. This information is communicated to the VT/CFC 303 and used to synchronize the electronic circuitry and physical operations during normal operation of the GCI apparatus 501.

The calibration magnet 411 is manipulated in relation to the five possible axes defined by the X-axis 406, the Y-axis 407, the Z-axis 408, the θ axis 409, and the EL axis 410. These axes correspond exactly to the five directions of movement possible for the virtual tip 405, which is the maximum number of degrees of freedom possible for the actual tip 377. The manipulation of calibration magnet 411 is accomplished by the electronic circuitry of the calibration fixture 321 as implemented in FIG. 11.

The circuitry of FIG. 11 operates as follows: A decode logic 101c responds to address and control bits originating from VT/CFC 303 and enables data buffer 51c and sets its direction. Step latches 52c and 53c store data to be presented to stepper drivers 54c, 56c, 58c, 60c, and 62c when strobed by decode logic 101c. Stepper motors 55c, 57c, 59c, 61c, and 63c respond to the stepper drive outputs to manipulate the magnetic calibration tip in the 5 axes. Absolute encoders 64c, 66c, 68c, 70c, and 72c are mechanically coupled to the corresponding stepper motors and provide position feedback to the VT/CFC 303. The outputs of the encoders 64C, 66C, 68C, 70C and 72C are buffered by data buffers 65c, 67c, 69c, 71c and 73c to temporarily store and transfer the data. Limit "switches" 74c, 75c, 76c, 77c, 78c, and 79c flag the ends of the three linear axes X, Y and Z. "Switches" 80c and 81c indicate when θ and EL are at zero position. Limit latch 82c stores this data when strobed by decode logic 101c.

Figure 13:
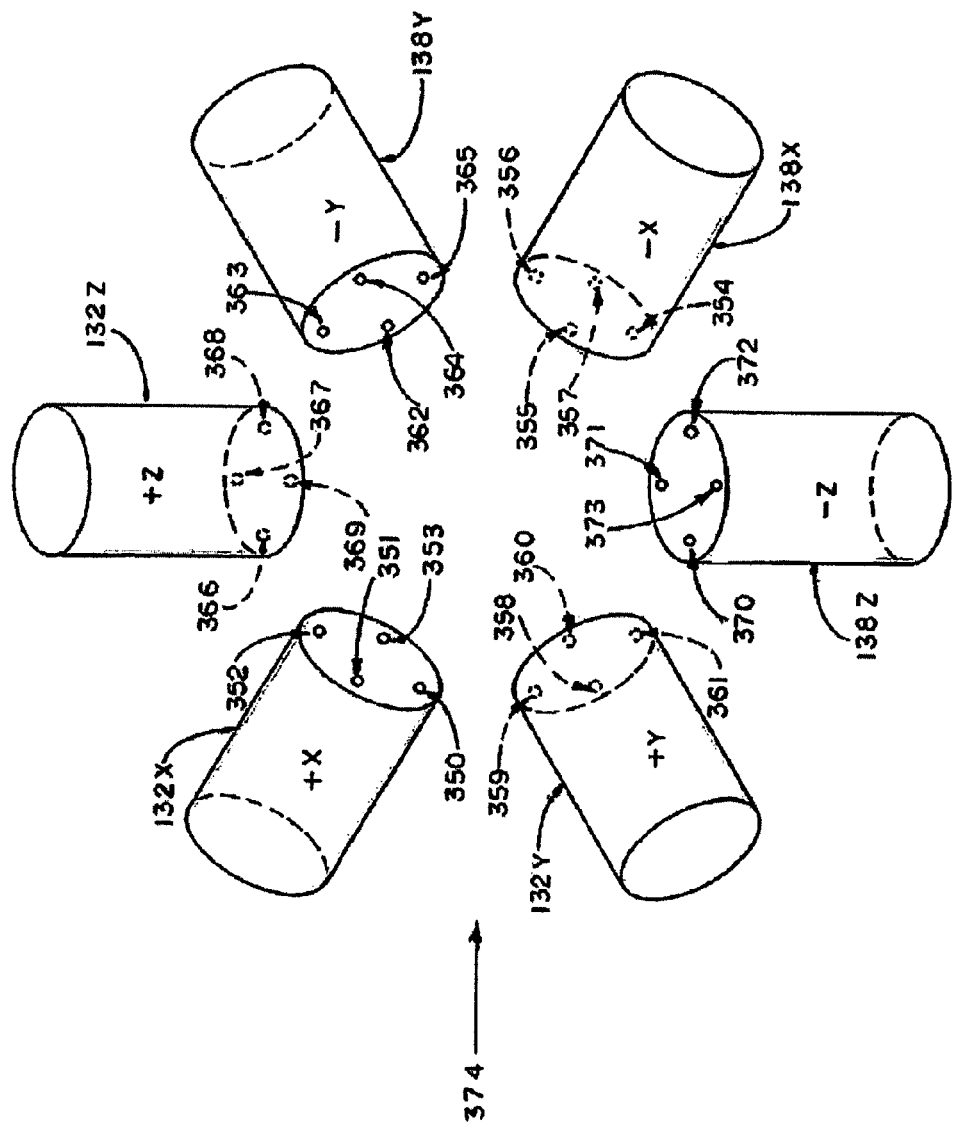
FIG. 13 is an orthographic representation view illustrating a polar configuration of the electromagnets with their corresponding magnetic field sensors.

FIG. 13 Illustrates the polar configuration 374 of the electromagnets 132X, 132Y, 132Z, 138Z, 138Y, and 138Z, the magnetic field sensors and temperature sensor pairs 350, 351, 352, 353, 354,355, 356, 357, 358, 359, 360, 361, 362, 363, 364, 365, 366, 367, 368, 369, 370, 371, 372, and 373. The electromagnets 132x, 132y, 132z are arranged in three orthogonal axes X, Y, Z, or as shown in FIGS. 13A and 13B.

Figure 13A:
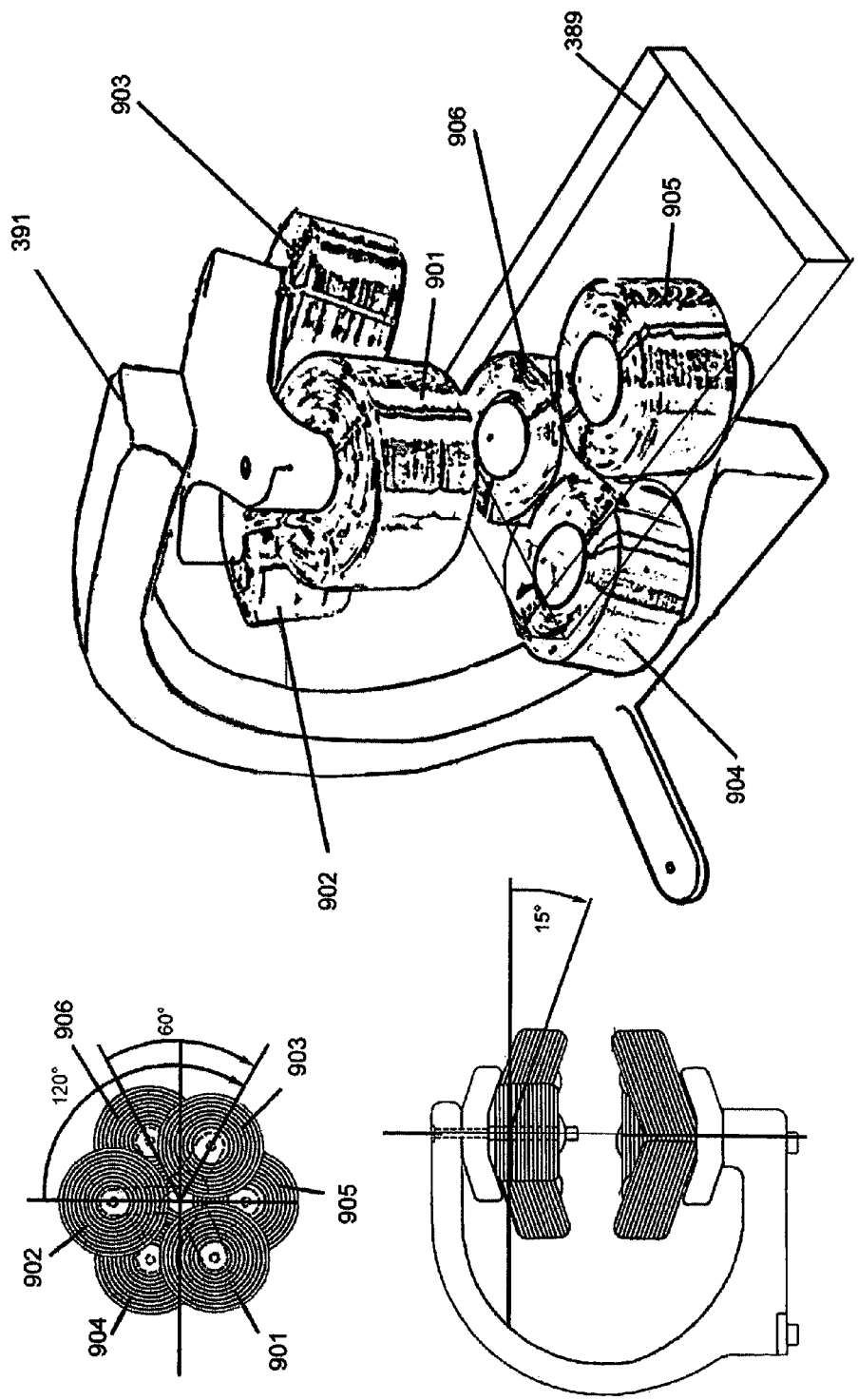
FIG. 13A is a possible polar configuration as a cluster of electromagnets forming the magnetic circuit with a C-Arm.
Figure 13B:
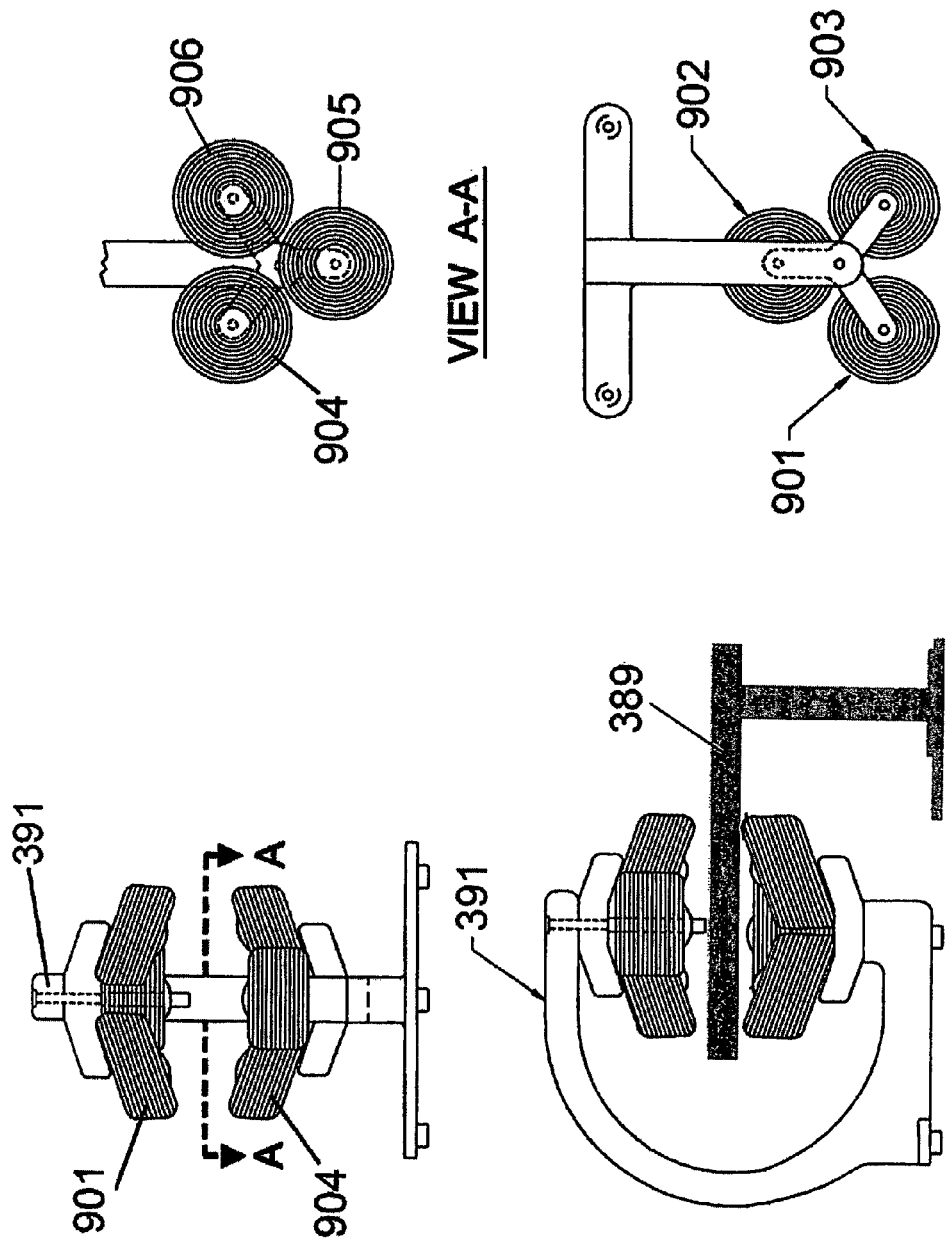
FIG. 13B is a representation of the geometrical layout of the coils, the arm and the table.
Figure 16:
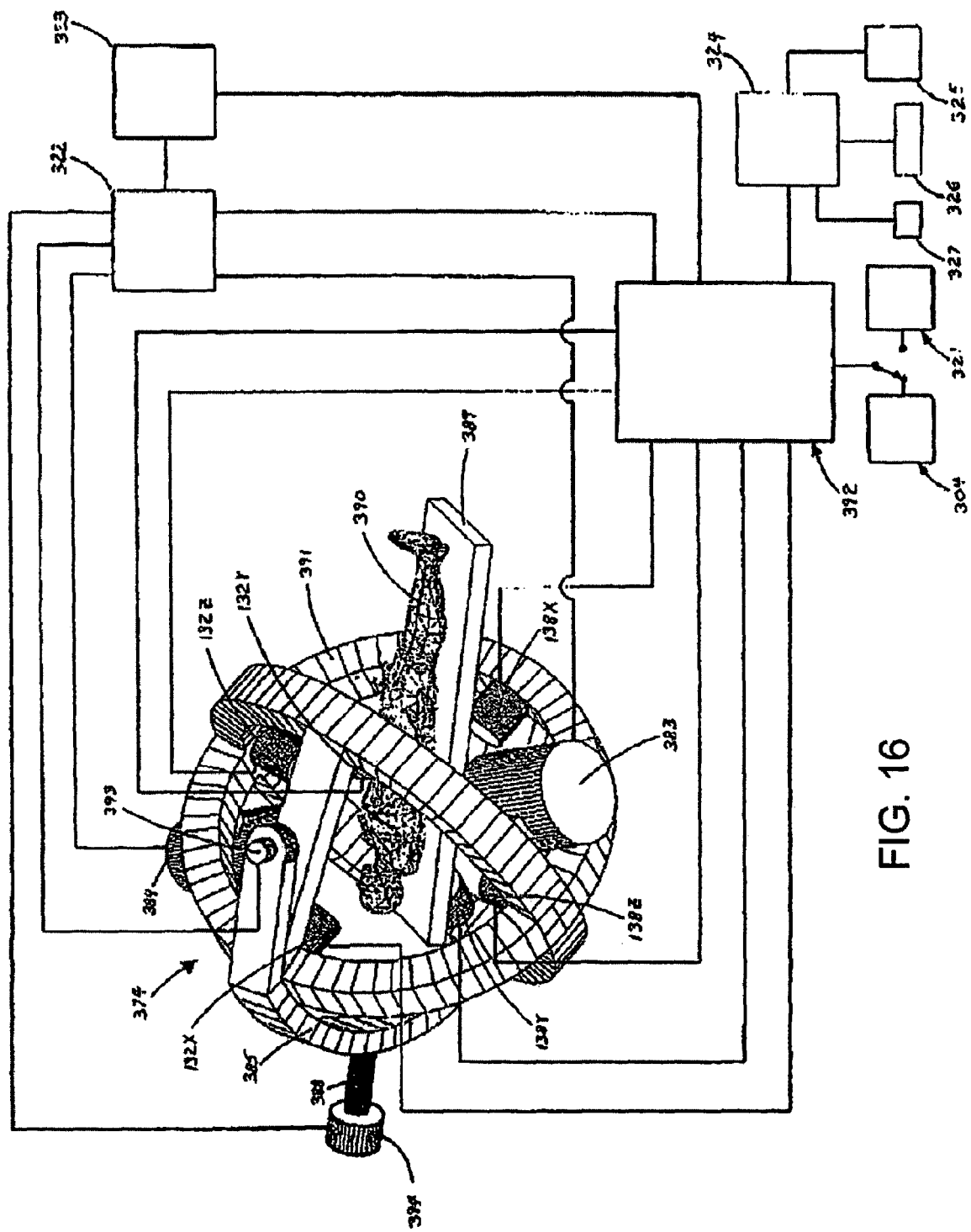
FIG. 16 illustrates a bi-plane X-ray ring incorporating the apparatus of FIG. 1B.

FIG. 13A and FIG. 13B illustrate a polar clustered configuration poles where the operating table 389 and electromagnets 901, 902, and 903 are configured relative to 904, 905, and 906, as approximately shown and mounted by the use of support assembly 391 configured as a C-Arm to compliment and close the magnetic field circuit. The polar configuration 374 is further expressed as a non-symmetrical distribution of the polar arrangement where electromagnet 901 and its counterpart 903 are rotated to provide a lobed electromagnetic field. This arrangement further optimizes the magnetic circuit and provides for free access for the physician and the patient while the Z axis electromagnets 905 and 906 do not obstruct the available access space as approximately shown by FIG. 13 and FIG. 16. Furthermore FIG. 13 and FIG. 13A and FIG. 13B compliment each other and are an alternative to the bi-plane ring shown in FIG. 16, FIG. 16A, FIG. 16B and FIG. 16C. Both arrangements represent a possible approach provided in accommodating the imaging technology modalities such as x-ray, Cat-Scan, Pet-Scan and Ultrasound, while FIG. 16 provides for the GCI apparatus 501 as a natural access for a fluoroscopic imaging on a bi-plane arrangement. FIGS. 13, 13A and 13B enable geometry with a bore of approximately 25 inches which is capable of incorporating a computer tomography apparatus and/or the modality noted above. Further embodiment of using the geometrical arrangement noted in FIGS. 13A and 13B is expressed in the ensuing descriptions of FIGS. 13C, 13D, 13E, 13F, 13G and 13H. The two competing architectures shown in FIG. 16, 16A, 16B 16C and FIG. 13A, 13B, provide for advantages and disadvantages in mounting the operating interface equipment 500, surgical medical equipment 502, and the GCI apparatus 501. Further FIGS. 13A and 13B illustrate an alternative arrangement of the coils attached to the C-arm, 391, and table 389. In this arrangement coils 901 through 906 are shown in a cluster configuration. This geometry diverts from the intuitive orthogonal structure of coils commonly used when generating vectors or vector gradients with the aide of electromagnetic coils. FIG. 13B further illustrates the six coils, 901 through 906, configured in a flower-like structure, or a cluster. Three of the coils are mounted at the top of the C-arm 391, and three at the bottom. The three coils forming the upper cluster are further shifted by 120 degrees relative to each other, as are the bottom three coils. In addition, the coils of the cluster at the top of the C-arm are also tilted downward somewhat, at an angle of 15 to 20 degrees, as are the coils of the cluster at the bottom of the C-arm tilted upward, as shown in FIG. 13B. The entire cluster at the top of the C-arm is rotated with respect to the bottom cluster by an angle of 60 degrees.

In FIG. 13B, the coils at the top of the C-arm 391 are marked as 901, 902, and 903, counting clockwise, and the bottom coils are marked 904, 905 and 906, counting in a counter clockwise direction. Coils 901 and 903 work as a pair and are designated as the X-axis pair of coils, coils 902 and 904 work as another pair and are designated as the Y-axis pair of coils, and coils 905 and 906 are the third pair and are designated as the Z-axis pair of coils.

Figure 1:
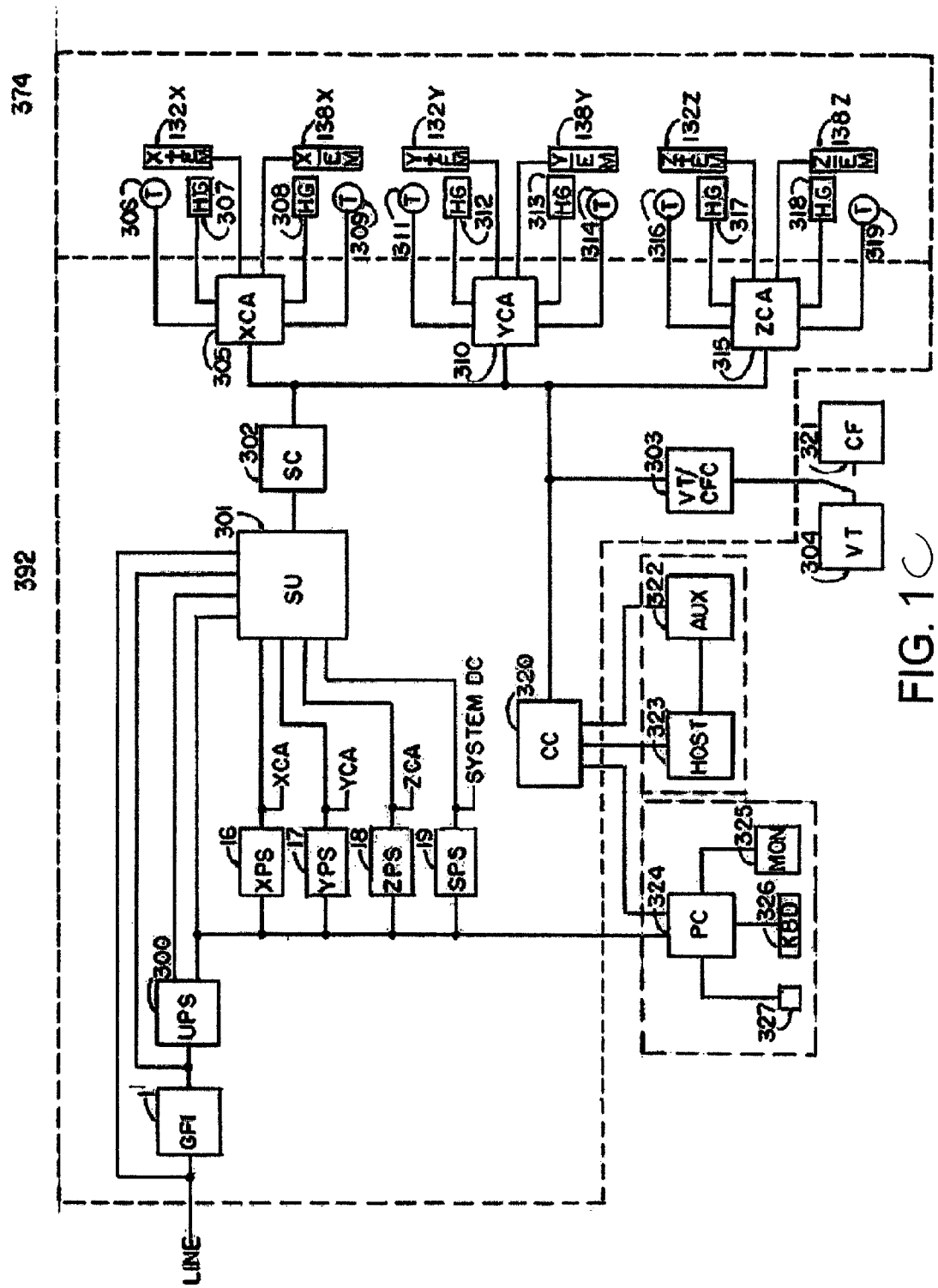
FIG. 1C is a block diagram of the catheter guidance system of FIG. 1B showing additional details not shown in FIG. 1B.
Figure 13C:
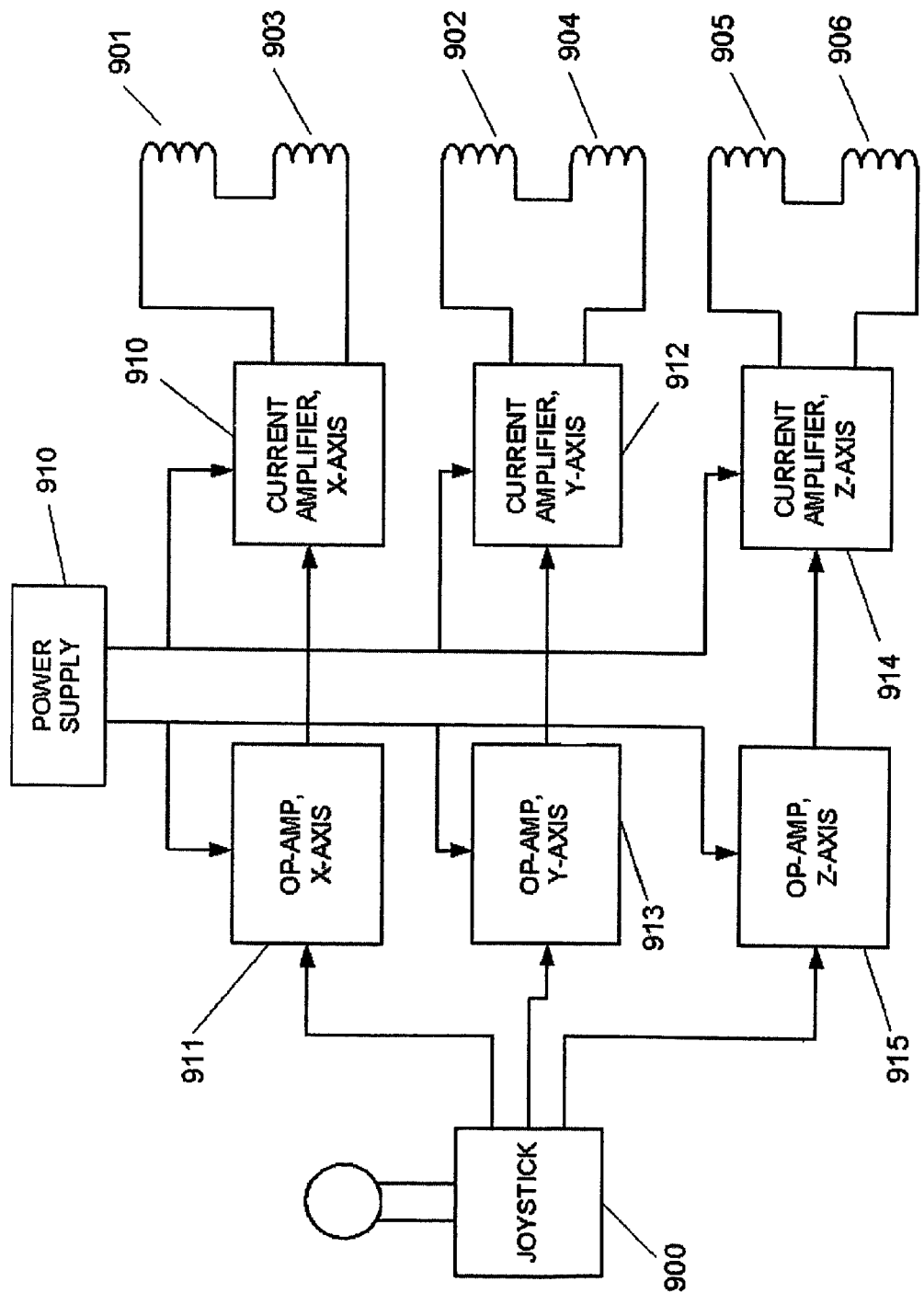
FIG. 13C is a block diagram representing the electronics scheme of clustered electromagnetic coils

FIGS. 13C, 13D, 13E, 13F, 13G and 13H, show an alternative architecture of the GCI apparatus 501 whereby the polar configuration noted in FIGS. 16. 16A, 16B, and 16C, is altered to accommodate the cluster configuration of the electro-magnet circuit as shown in FIGS. 13A and 13B. FIG. 13B is a simplified block diagram of the electrical scheme of the various components of the system. The system comprises a power supply, 910, a joystick, 900, feeding three channels, X, Y, and Z, where the three signals taken together form a matrix V, 923, shown in FIG. 13D, comprising elements $Vj_x$, $Vj_y$, and $Vj_z$. This arrangement is further explained in FIGS. 13D, 13E, 13F, 13G and 13H. FIG. 13C, the X-axis channel, comprises an Op-Amp 911, a current amplifier 910, and coil pair 901, 903. The Y-axis channel comprises an Op-Amp 913, a current amplifier 912, and coil pair 902, 904. The Z-axis channel comprises an Op-Amp 915, a current amplifier 914, and coil pair 905, 906. As shown, each pair of coils is connected in series and further connected to the output of power amplifiers, 910, 912, and 914, for the X, Y and Z axes, respectively. The alternative architecture to FIG. 1 shown in FIG. 13C receives its input signal command from the joystick, 900. Upon command from the operator using the joystick 900 to move in one or more axes, the joystick 900 sends its signal to an array of operational amplifiers, 911, 913, and 915, corresponding to the X, Y, and the Z axes respectively. Op-Amps 911, 913, and 915 translate the signal received from joystick 900 and perform an Inverse operation on the matrix of the three signals for the three axes. The Op-Amp array 932 multiplies the signal from joystick 900 represented as vector V, 923, by another matrix M-inverse, shown in FIGS. 13F and 13G as 927, such that the output of the Op-Amp array 932 is M-inverse times V, where M is the characteristic matrix 925 of the cluster arrangement comprising the six coils 901 through 906. The output from the Op-Amp array 932, comprising Op-Amps 911, 913, and 915, is obtained, and is fed to power amplifiers 910, 912, and 914, driving the six coils 901 through 906 to obtain the result of generating a motion in the desired direction, hence providing the apparatus 501 with the ability to translate the desired motion of the operator or the clinician as to move the catheter tip 377 in a body lumen of a patient, 390. This scheme as shown in FIGS. 13D, 13E, 13F, and 13G, is reduced further in FIG. 13H where the input signal V, 931, from Joystick 900, is fed to an Mchar-Inverse Op-Amp array, 932. The resultant output from the array 932 is the matrix product Mchar-Inverse by the vector V. This signal is fed to current amplifiers 928, their signal output represented by the vector B, 933, is then fed as the respective current to the coils 901 through 906, thereby producing the result of translating the hand-movement of the clinician into the appropriate signal, thus moving the catheter tip to the desired location.

Figure 13H:
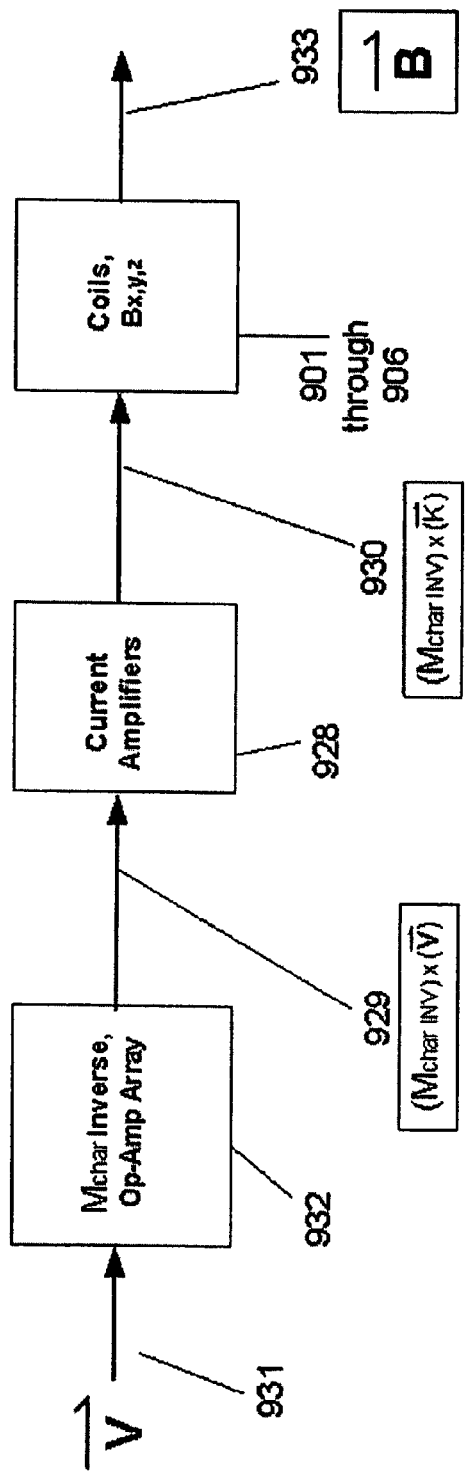
FIG. 13H is a logical flow diagram of FIG. 13G

In summary, the alternative arrangement shown above provides GCI 501 a method in which a competing architecture to FIG. 1 is employed where a non-symmetrical arrangement of the coils is linearized through the use of the scheme shown in FIG. 13H, thereby producing the desired results. This is shown in FIG. 13E.

FIG. 14 shows an arrangement of the magnetic field sensors and temperature sensor pairs into sensor arrays 306, 307, 308, 309, 311, 312, 313, 314, 316, 317, 318, and 319. Each orthogonal axis is divided into two poles by positioning a second electromagnet coaxially with the first. For example, electromagnet 132x is coaxial with electromagnet 138x, electromagnet 132y is coaxial with electromagnet 138y, and electromagnet 132z is coaxial with electromagnet 138z. Since the rotational movements of the virtual tip 405 defined by θ 403 and EL 404, as shown in FIG. 6 occur within the X-Y plane and the X-Z plane respectively, electromagnet poles along the X-, Y- and Z-axes are sufficient to affect movement of the actual catheter tip 377 in exactly the same five axes as defined for the virtual tip 405 as previously described in connection with FIG. 6.

In one embodiment, each magnetic field sensor contained in the MFS arrays 307, 308, 312, 313, 317, and 319, is paired with a temperature sensor (TS) contained in temperature sensor arrays 306, 309, 311, 314, 316, and 318. These paired combinations are detailed in FIG. 14 and in the table below. The magnetic field sensors-temperature sensor (MFS/T) pairs are arranged in quadrants on the pole face of the electromagnets 132x, 132y, 132z, 138x, 138y, and 138z.

As shown in FIG. 13, the MFS/TS pairs 350, 351, 352, and 353 are arranged in quadrants on electromagnet 132x pole face. Magnetic field sensor and temperature sensor (TS) pairs 354, 355, 356, and 357 are arranged in quadrants on electromagnet 138x pole face. Magnetic field sensor and temperature sensor (TS) pairs 358, 359, 360, and 361 are arranged in quadrants on electromagnet 132y pole face. Magnetic field sensor and temperature sensor (TS) pairs 362, 363, 364, and 365 are arranged in quadrants on electromagnet 138y pole face. Magnetic field sensor and temperature sensor (TS) pairs 366, 367, 368, and 369 are arranged in quadrants on electromagnet 132z pole face. Magnetic field sensor and temperature sensor (TS) pairs 370, 371, 372, and 373 are arranged in quadrants on electromagnet 138z pole face.

FIG. 14 illustrates the pairing of the magnetic field sensors and temperature sensors as mounted in FIG. 13. The magnetic field sensors and temperature sensors are mounted as isothermal pairs, and each pair functions in conjunction with each other. The magnetic field sensors measure the position of the actual tip 377 during the measurement phase, as controlled by microcontrollers 102x, 102y and 102z of XCA 305, YCA 310 and ZCA 315, respectively, during which time the electromagnets 132X, 132Y, 132Z, 138X, 138Y, and 138Z are de-energized. This is done in order to be able to take accurate and sensitive measurements with the magnetic field sensor arrays 307, 308, 312, 313, 317, and 318, as they would otherwise be saturated with the flux from the electromagnets. The temperature sensor arrays 306, 309, 311, 314, 316, and 319 monitor the ambient temperature to detect an increase that may be uncomfortable for the patient or potentially damaging to surrounding tissues, and provide correctional data for calculating position based on the magnetic field sensors. The isothermal pairs are as follows:

magnetic field sensor 113X and temperature sensor (TS) 122x form pair 350. Magnetic field sensor 114x and temperature sensor (TS) 123x form pair 351. Magnetic field sensor 115X and temperature sensor (TS) 124x form pair 352. Magnetic field sensor 116x and temperature sensor (TS) 125x form pair 353. Magnetic field sensor 117x and temperature sensor (TS) 126x form pair 354. Magnetic field sensor 118x and temperature sensor (TS) 127x form pair 355. Magnetic field sensor 119x and temperature sensor (TS) 128x form pair 356. Magnetic field sensor 120X and temperature sensor (TS) 129x form pair 357. Magnetic field sensor 113y and temperature sensor (TS) 122y form pair 358. Magnetic field sensor 114y and temperature sensor (TS) 123y form pair 359. Magnetic field sensor 115y and temperature sensor (TS) 124y form pair 360. Magnetic field sensor 116y and temperature sensor (TS) 125y form pair 361. Magnetic field sensor 117y and temperature sensor (TS) 126y form pair 362. Magnetic field sensor 118y and temperature sensor (TS) 127y form pair 363. Magnetic field sensor 119y and temperature sensor (TS) 128y form pair 364. Magnetic field sensor 120y and temperature sensor (TS) 129y form pair 365. Magnetic field sensor 113z and temperature sensor (TS) 122z form pair 366. Magnetic field sensor 114z and temperature sensor (TS) 123z form pair 367. Magnetic field sensor 115z and temperature sensor (TS) 124z form pair 368. Magnetic field sensor 116z and temperature sensor (TS) 125z form pair 369. Magnetic field sensor 117z and temperature sensor (TS) 126z form pair 370. Magnetic field sensor 118z and temperature sensor (TS) 127z form pair 371. Magnetic field sensor 119z and temperature sensor (TS) 128z form pair 372. Magnetic field sensor 120z and temperature sensor (TS) 128z form pair 373.

Figure 15:
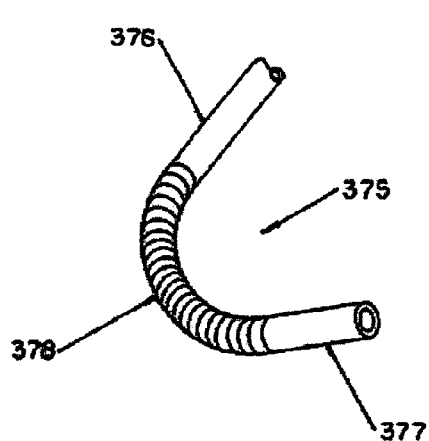
FIGS. 15 and 15A are fragmentary, perspective views of a catheter assembly and a guidewire assembly for use in the apparatus of FIG. 1B.
Figure 15A:
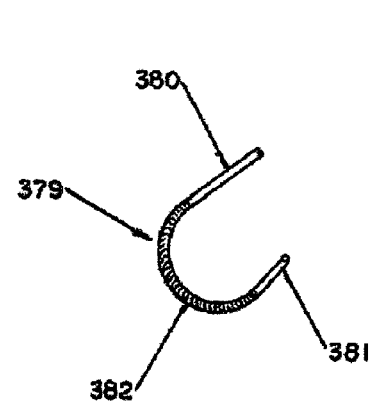

FIGS. 15 and 15A show an improved catheter assembly 375 and guidewire assembly 379 to be used with the GCI apparatus 501. The catheter assembly 375 is a tubular tool that includes a catheter body 376 which extends into a flexible section 378 that possesses increased flexibility for allowing a more rigid responsive tip 377 to be accurately steered through a torturous path.

The magnetic catheter assembly 375 in combination with the GCI apparatus 501 reduces or eliminates the need for the plethora of shapes normally needed to perform diagnostic and therapeutic procedures. This is due to the fact that during a conventional catheterization procedure, the surgeon often encounters difficulty in guiding the conventional catheter to the desired position, since the process is manual and relies on manual dexterity to maneuver the catheter through a tortuous path of, for example, the cardiovascular system. Thus, a plethora of catheters in varying sizes and shapes are be made available to the surgeon in order to assist him/her in the task, since such tasks require different bends in different situations due to natural anatomical variations within and between patients.

By using the GCI apparatus 501, only a single catheter would be needed for most, if not all patients, because the catheterization procedure is now achieved with the help of an electromechanical system that guides the magnetic catheter and guidewire assembly 375 and 379 to the desired position within the patient's body 390 as dictated by the surgeon's manipulation of the virtual tip 405, without relying on the surgeon pushing the catheter, quasi-blindly, into the patient's body. The magnetic catheter and guidewire assembly 375, 379 (i.e., the magnetic tip can be attracted or repelled by the electromagnets 132X, 132Y, 132Z) provides the flexibility needed to overcome tortuous paths, since the GCI apparatus 501 overcomes most, if not all of the physical limitations faced by the surgeon while attempting to manually advance the catheter tip 377 through the patient's body.

The guidewire assembly 379 is a tool with a guidewire body 380 and a flexible section 382, which possesses increased flexibility for allowing a more rigid responsive tip 381 to be accurately steered around sharp bends so as to navigate a torturous path. The responsive tips 377 and 381 of both the catheter assembly 375 and the guidewire assembly 379, respectively, include magnetic elements such as permanent magnets. The tips 377 and 381 include permanent magnets that respond to the external flux generated by the electromagnets 132X, 132Y, 132Z and 138X, 138Y, 138Z.

The responsive tip 377 of the catheter assembly 375 is tubular, and the responsive tip 381 of the guidewire assembly 379 is a solid cylinder. The responsive tip 377 of catheter assembly 375 is a dipole with longitudinal polar orientation created by the two ends of the magnetic element positioned longitudinally within it. The responsive tip 381 of guidewire assembly 379 is a dipole with longitudinal polar orientation created by the two ends of the magnetic element 377 positioned longitudinally within it. These longitudinal dipoles allow the manipulation of both responsive tips 377 and 381 with the GCI apparatus 501, as the electromagnets 132X, 132Y, 132Z, 138X, 138Y, and 138Z will act on the tips 377 and 381 and "drag" them in unison to a desired position as dictated by the operator.

Figure 15B:
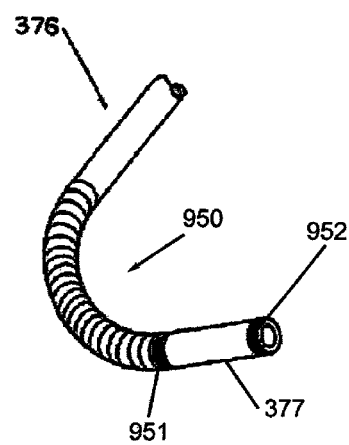
FIG. 15B a representation of a catheter fitted with a magnetic tip and two piezoelectric rings.

FIG. 15B illustrates a further improvement of catheter assembly 375 and guide-wire assembly 379 to be used with the GCI apparatus 501, where the catheter assembly 950 is fitted with an additional two piezoelectric rings, 951 and 952, located as shown. An ultrasonic detector in combination with apparatus 501 provides an additional detection modality of the catheter tip whereby an ultrasonic signal is emitted as to excite the two piezoelectric rings and provide a measure of rotation of the catheter tip relative to the north pole axis of the magnet 377. With the aide of the computer 324, the GCI apparatus 501 is capable of defining the angle of rotation of the tip 377 and in a more elaborate scheme known to those familiar with the art the piezoelectric rings 951, 952, can provide additional position information to define the position, orientation, and rotation of the catheter tip 377 relative to the stereotactic framing as described further in FIGS. 17 and 17A.

Figure 16A:
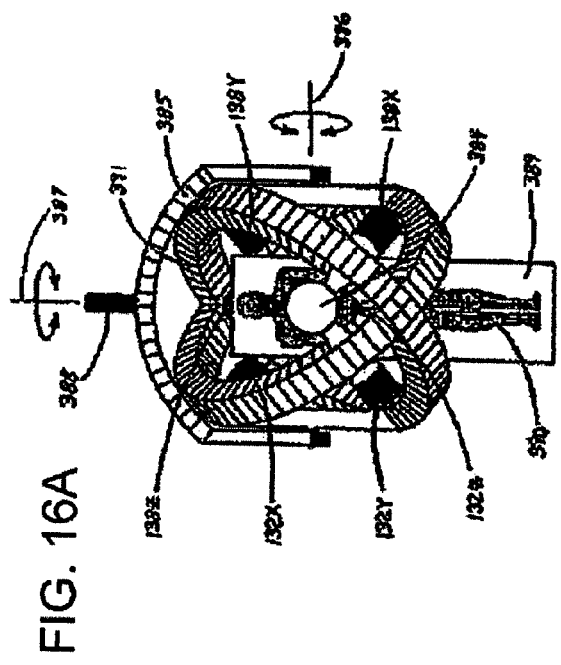
FIG. 16A illustrates a top view of the apparatus of FIG. 1B.
Figure 16C:
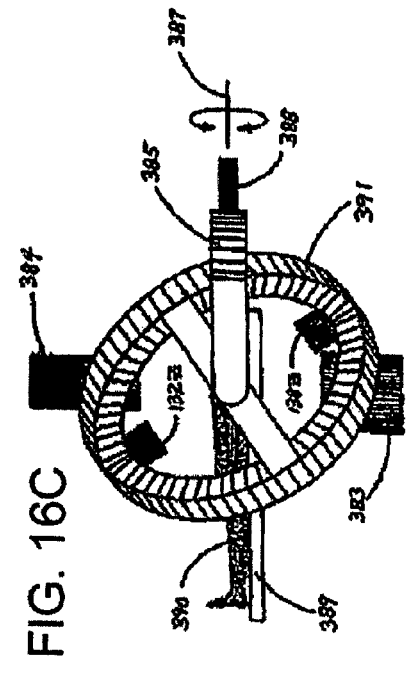
FIG. 16C illustrates a side view of the apparatus of FIG. 1B.
Figure 16B:
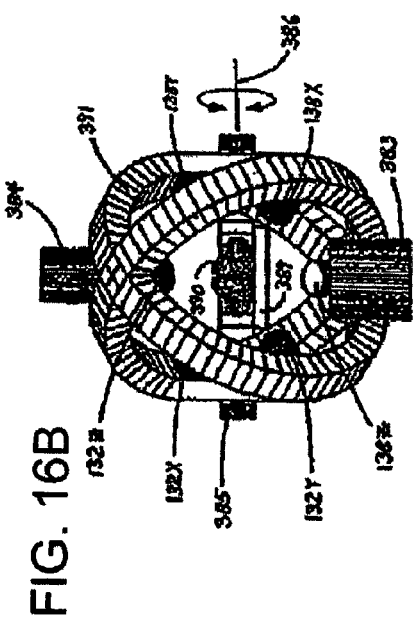
FIG. 16B illustrates an end view of the apparatus of FIG. 1B.

FIG. 16 illustrates a bi-plane x-ray ring incorporating the apparatus of FIG. 1B. FIGS. 16A, 16B and 16C are further elaboration of FIG. 16, and show in further detail, elements that could not be depicted by the isometric view of FIG. 16, or were omitted from FIG. 16 for clarity. Additionally, FIGS. 16A, 16B, and 16C are top, end, and side views respectively of the electromagnet and imaging assembly 391 and support assembly 385.

FIG. 16 further illustrates the overall relationship between the operating table 389, the patient 390, a T-axis encoder 394, a trunnion 388, a support assembly 385, a polar support 391, a G-axis encoder 393, the x-ray source 383, an image intensifier 384, the electromagnets 132X, 132Y, 132Z, an overall arrangement referred to as polar configuration 374, electromagnets 138X 138Y, 138Z, the power supply and control system 392, the auxiliary equipment 322, the host system 323, the PC 324, the virtual tip assembly 304, the calibration fixture 321, the mouse 327, the keyboard 326, the monitor 325, as they are approximately oriented for visual aid. The function of the components that has not yet been described will be explained in the ensuing paragraphs, with reference to FIGS. 16, 16A, 16B, and 16C.

The T-axis encoder 394 and the G-axis encoder 393 provide the system with gantry position information for use in calculating the desired coordinate rotation prior to energizing the electromagnet. The trunnion 388 acts as a truss for the support assembly 385. Polar support 391 pivots on the G-axis of support assembly 385. The polar assembly 391 supports the x-ray source 383 and x-ray image intensifier 384 that produce x-ray images to be overlaid with the actual catheter position image on the monitor 325 of the operator interface 500. Polar support 391 provides a mounting surface for electromagnets 132X, 132Y, 132Z, 138X, 138Y, and 138Z in their appropriate coaxial arrangements as was already described in FIG. 13.

The trunnion 388 is centered on an axis, namely the T-axis 387 depicted in FIG. 16A. The T-axis encoder 394 is mechanically coupled to the trunnion 388 to encode positional data of the support assembly 385 in the T-axis. A gimbal-axis (G-axis) 386, depicted in FIG. 16A, intersects with the T-axis 378 at the center point of the polar support 391. This center point coincides exactly with the center point of the X-ray field of view. A G-axis encoder 393 is mechanically coupled to the support assembly 385 along the G-axis 386. A detailed description of the functionality of the above components will follow in the ensuing description.

FIG. 16 Illustrates the x-ray support assembly 385 and 391 as configured on an anteroposterior projection with 20 degrees of caudal angulation (AP caudal). FIG. 17 illustrates a general connection of the GCI apparatus 501 to cineangiographic equipment 502. The cineoangiographic equipment 502 is interfaced with the GCI apparatus 501 through operator interface equipment 500. The cineoangiography image of an arterial tree is shown on video monitor 325, with the x-ray image of catheter tip 377 position superimposed. The display of these images is synchronized by the GCI apparatus 501 via the communications controller 320, and is realized on the monitor 325 of the operator interface 500.

FIG. 17A illustrates forming a stereotactic frame in support of position definition of the catheter tip relative to the frame. This method utilizes fiducial markers formed as an approximate cube.

The solution presented herein is a method of capturing the Fluoroscopic Image generated by the x-ray Apparatus and/or ultrasonic imaging technique to create Referential Markers for synchronizing the image of the catheter tip or guide wire, which is generated by the GCI apparatus and superimpose that image onto the fiducial markers which are represented digitally and are linked dynamically as to create one image which moves in unison with the area of interest. For example, the beating heart and its cardio-output, the pulmonary expansion and contraction, or a spasm of the patient, can be dynamically captured and linked together as to achieve unison motion between the catheter's tip and the body's organ in question.

FIG. 17A further illustrates the image capture technique of superimposing the fiducial markers 700A1, 700A2, 700A3, 700A4, 700B1, 700B2, 700B3, and 700B4 onto the fluoroscopic/ultrasonic image, generated as shown in image 17. The scheme provided identifies the dynamic location of the catheter tip 377 with reference to the fluoroscopic/ultrasonic image. The referential frame formed by the fiducial markers 700Ax defines the catheter's tip position relative to the stereotactic frame. Furthermore, by employing a technique of geometric projection this method provides for a synchronized image-capture relative to catheter tip, 377 thereby affording the superimposition of the fluoroscopic/ultrasonic image relative to both the fiducial markers and the catheter tip on a dynamic basis, hence, providing position definition with a frame of reference.

Figure 17B:
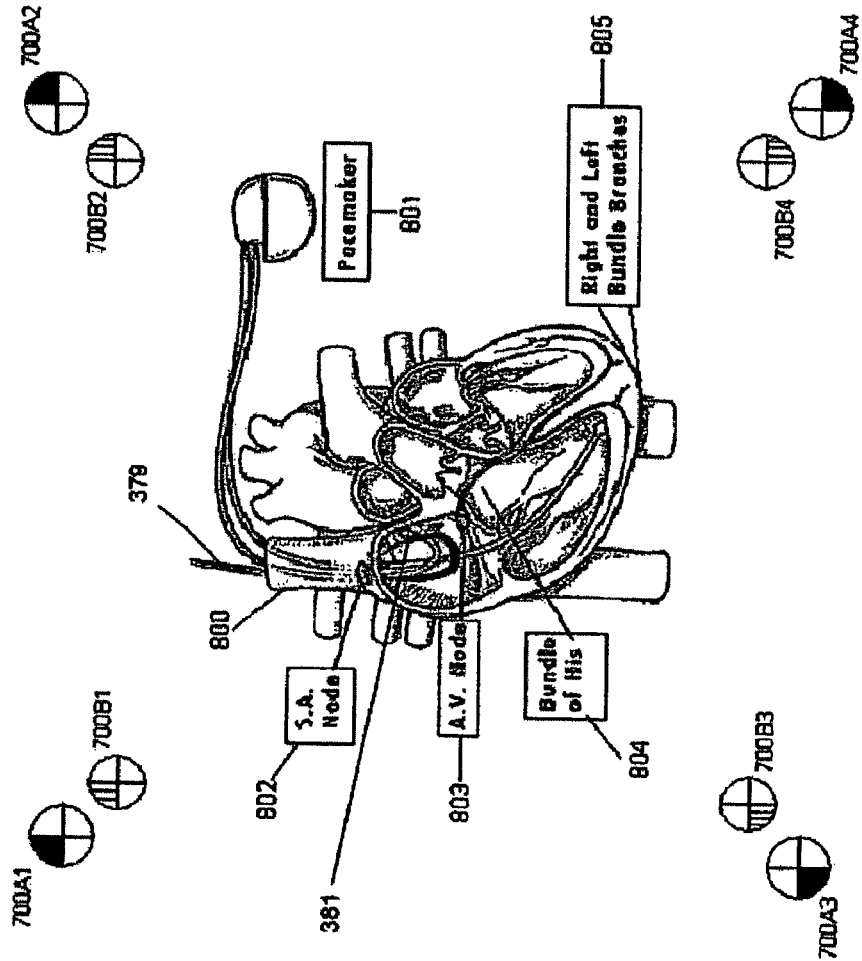
FIG. 17B illustrates the use of fiduciary markers in performing a pacemaker electrode implementation.

FIG. 17B illustrates the implantation of cardiac pacemaker 801 with electrodes as shown, placed in area relative to the S.A. Node 802, A.V. Node 803, and a bundle of His 804. Further illustrated are the right and left bundle branches 805. Pacemaker implantation is essential for the survival of patients with heart rhythm or electrical conduction disturbances. This procedure is performed by the implantation of a small electrode in the heart cavity wall (ventricle or atrium). The other end of the electrode is attached to an electronic device 801 which is implanted under the chest skin and which generates stimulation pulses to simulate the heart rhythm. Similar devices apply electrical shock when life threatening heart electrical disturbances are detected by the electrodes (Automatic Implantable Cardiac Defibrillator (AICD). These electrodes are placed through a vein by pushing and manipulating under fluoroscopy. Through the use of the apparatus proposed GCI 501 and guidewire 379 fitted with magnetic tip 381 is used to carry and place the electrodes of pacemaker 801 in its proper position by using the method and apparatus described in this patent. By employing the fiducial markers 700A1, 700A2, 700A3, 700A4, 700B1, 700B2, 700B3, and 700B4 the physician navigates the guidewire 379 through the heart lumen while having a continuous dynamic referential frame identifying the guidewire tip 381 and as shown in 17 and further illustrated by FIG. 17A. Many times, the manipulation to place the electrodes in a proper position is difficult and the results are sub-optimal due to anatomical variations. The use of the proposed apparatus 501 provides simplicity in performing such a complex operation while the physician is capable of moving, pushing, and placing the electrodes of pacemaker 801 in its precise anatomical position without compromise due to the inability of navigating, guiding, controlling, and imaging the movement of the guidewire and the pacemaker electrodes accurately.

Having described the constituent components of the GCI apparatus 501, its general and mathematical operations for controlling the position of the actual catheter tip 377 in relation to adjustments made to the virtual tip 405 and calculations to determine the new location of the actual catheter tip 377 will now be explained with reference to FIGS. 18 through 23.

Upon application of power, the built-in test routines residing in Supervisory Unit (SU) 301, System Controller (SC) 302, X-axis controller and amplifier (XCA) 305, Y-axis controller and amplifier (YCA) 310, Z-axis controller and amplifier (ZCA) 315, Communication Controller (CC) 320, Computer 324, and Virtual Tip/Calibration Fixture Controller (VT/CFC) 303, perform a series of self diagnostic tests. In addition, certain tests are performed on a continuous basis in the background. Exemplary background tests include DC power supply voltage and current monitoring, AC voltage and current monitoring and communication tests. These background tests are interleaved between normal functions in a manner that is transparent to the user.

The results of the test routines are reported to System Controller (SC) 302. System Controller (SC) 302 compares these results to expected values stored in Non Volatile Memory (NVM) 39 (FIG. 3). Following a test failure or the detection of any anomalous behavior, System Controller (SC) 302 determines the severity of the situation. If an uncorrectable condition exists, System Controller (SC) 302 initiates a graceful power down. If, on the other hand, corrective action can be taken to alleviate or eliminate the problem, System Controller (SC) 302 instructs Computer 324 to sound an alarm, and instructs the monitor 325 to display an error prompt. Any detected failures are also stored as error codes in Non Volatile Memory (NVM) 39 for later review and troubleshooting.

In one embodiment, the Virtual Tip 405 and the Calibration Fixture (CF) 321 (FIGS. 5, 6, 11, and 12) have 8 inches of travel in the X, Y, and Z axes. This corresponds to the 8"×8"×8" control area of the polar configuration 374 (FIG. 13). The Virtual Tip 405 and the Calibration Fixture 321 also have 360° of rotation in the θ and elevation axes.

Stepper motors 55C, 57C 59C, 61C, and 63C with the coupled encoders 64C, 66C, 68C, 70C and 72C revolve once during an 8-inch excursion in the X, Y, or Z axes. Stepper motors 55C, 57C 59C, 61C, and 63C have, for example, a resolution of 400 half steps per revolution, which equates to a positioning resolution of 0.022". Additionally, the encoders may have a resolution of 512 bits per revolution, which equates to a measurement resolution of 0.015625". In the θ and EL axes, the stepper motor resolution may be 0.9° and the encoder resolution may be 0.703125°.

During calibration, Calibration Fixture (CF) 321 is placed within the polar configuration 374 and connected to Virtual Tip/Calibration Fixture Controller (VT/CFC) 303. Virtual Tip/Calibration Fixture Controller (VT/CFC) 303 then moves Calibration Fixture (CF) 321 by sending codes to drive stepper motors 55c, 57c, 59c, 61c, and 63c. Encoders 64c, 66c, 68c, 70c, and 72c are then read by Calibration Fixture (CF) 321 to determine the present position and orientation of magnet 411. The position data from the encoders is compared to the position data derived from magnetic field sensor arrays 307, 308, 312, 313, 317, and 318 (FIGS. 1, 7, 8, and 9). The magnetic field sensor arrays 307, 308, 312, 313, 317 and 318 responses are thus characterized for the full range of the magnet 411 positions and orientations, and hence for the magnetic catheter tip 377 as well.

During normal operation, Virtual Tip 405 is connected to Virtual Tip/Calibration Fixture Controller (VT/CFC) 303. As tip 405 is manipulated, Virtual Tip/Calibration Fixture Controller (VT/CFC) 303 reads encoders 64, 66, 68, 70, and 72. The position data obtained from the Virtual Tip 405 is used by the System Controller 302 to determine the desired position (DP) of the actual tip (AT) and to control its motion as defined in the description of FIG. 23.

Figure 18:
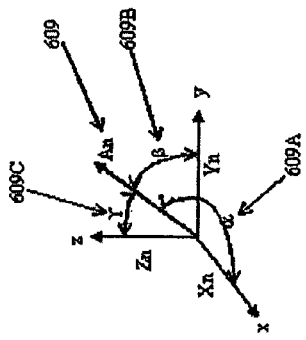
FIG. 18 is a vectorial representation of the magnitude and direction of the resultant force vector applied by the electromagnets of FIG. 13.

The electromagnetic field generated by electromagnets 132x, 132y, 132z, 138x, 138y, and 138z of FIG. 13 will produce a resultant force on the actual catheter assembly tip 377 and guidewire assembly tip 381 (FIGS. 15 and 15A). This resultant force can be represented by force vector B 600 with a given magnitude and direction. This resultant force vector B together with its constituent vectors are illustrated in FIG. 18. Vector B is the resultant vector of the force vectors emanating from the six electromagnets 132x, 132y, 132z, 138x, 138y, and 138z together, upon a move command from the XCA 305, YCA 310 and ZCA 315. Vector Bx 601 is the projection of Vector B 600 on the X-axis, Vector By 602 is the projection of Vector B 600 on the Y-axis, and Vector Bz 603 is the projection of vector B 600 on the Z-axis. The angles α604, β605, and δ606 are the corresponding angles between the vectors B 600 and Bx 601, vectors B 600 and By 602, and vectors B 600 and Bz 603, respectively.

As stated earlier, and still referring to FIG. 18, the magnitude of the force vector B 600 resulting from the electromagnetic field is $$B=\sqrt{Bx^2+By^2+Bz^2}$$

and its direction is given by the three angles below:

$$\alpha=\cos^{-1} Bx,\ \beta=\cos^{-1} By,\ \delta=\cos^{-1} Bz$$

The force vector B is produced through commands sent from system controller 102 based on: 1) inputs from sensor arrays 307, 308, 312, 313, 317, and 318 processed by XCA 301, YCA 310 and ZCA 315 on the location of the actual catheter tip 377 within the patient's body 390, and 2) inputs from VT/CFC 303 on the desired position of the actual catheter tip 377 as indicated by virtual tip 405 position. A code stored in ROM 40 of system controller 302 (FIG. 3) is processed by microcontroller 33 to generate the constituent vector components Bx 601, By 602, and Bz 603 of B 600. The magnitude of each of these constituent vectors will be translated to the appropriate XCA 305, YCA 310, and ZCA 315 to cause changes in modulator outputs, which, in turn, change the electromagnetic field produced by electromagnets 132x and 138x, 132y and 138y, and 132z and 138z. The constituent vectors Bx, By and Bz will then be physically realized as electromagnetic fluxes along the X-, Y- and Z-axes and thereby produce a resultant force B 600 on the actual catheter tip 377 to effectively drag it to the desired position.

The new position of the actual catheter tip 377 is then determined in order to verify that is indeed in the desired position or if further adjustments are necessary or if an obstacle has been encountered. The methods by which system controller 302 determines the new actual catheter tip 377 position will be explained mathematically with reference to FIGS. 18A through 22.

Figure 18B:
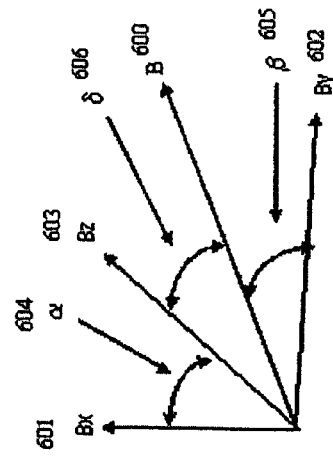
FIG. 18B illustrates the resultant vector as detected by the magnetic field sensors of FIGS. 20 and 20A.
Figure 18A:
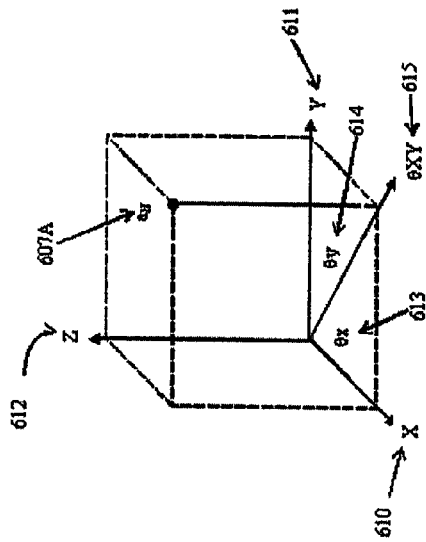
FIG. 18A illustrates the polarity of the magnetic tip of the catheter in relation to the virtual origin of the coordinate system.
Figure 19:
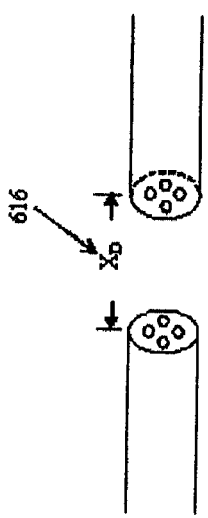
FIG. 19 illustrates the distance between two opposing electromagnets for use in the apparatus of FIG. 1B.
Figure 19A:
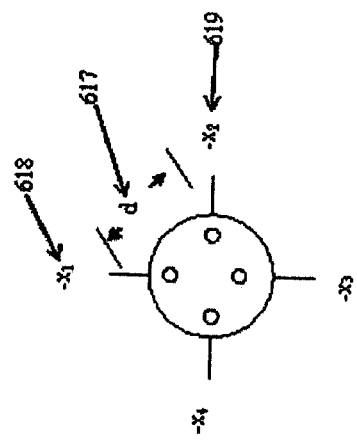
FIG. 19A illustrates the distance between adjacent magnetic field sensors of FIG. 19.

The following notations were assigned to the variables associated with FIGS. 18A, 19, and 19A and will be used in the ensuing discussion:

$a_N$: The most distal end of the magnetic element of the actual catheter tip assembly as indicated by its North dipole (see e.g., FIG. 18A).

$a_S$: The proximal end of the magnetic element of the actual catheter tip assembly 377 as indicated by its south dipole (see e.g., FIG. 18A).

$a_D$: Length of the actual catheter tip magnet 377 equal to the distance between the points $a_N$ and $a_S$ (refer to FIG. 18A).

$X_D$: Distance between opposite coaxial poles along the x-axis, that is the distance between the polar faces of electromagnets 132x and 138x (refer to numeral reference 616 in FIG. 19).

$-x_1, -x_2, -x_3, -x_4$: MFS and TS pairs 354, 355, 356, 357, respectively. (see FIGS. 13 and 19A).

d: The Distance between each consecutive MFS/TS pair, that is the distance between MFS/TS pair 354 and MFS/TS 355, MFS/TS 355 and MFS/TS pair 356, and so forth (refer to FIG. 19A).

$x_1, x_2, x_3, x_4$: MFS and TS Pairs 350, 351, 352, 353, respectively (refer to FIGS. 13 and 19A).

ROT: The angle of rotation θ in the X-Y plane (refer to numeral reference 625 in FIG. 21).

ELEV: The angle of EL in the X-Z plane (refer to numeral reference 626 in FIG. 22).

The electromagnetic field induced by electromagnets 132x, 132y, 132z, 138x, 138y, and 138z of FIG. 13 produces a resultant force on the actual catheter assembly tip 377 and guidewire assembly tip 381 (FIGS. 15 and 15A). This resultant force can be characterized as a force vector with a given magnitude and direction, and is illustrated in FIG. 18 along with its constituent vectors. Vector B 600 is the resultant vector of the force vectors emanating from the six electromagnets 132x, 132y, 132z, 138x, 138y, and 138z together, upon a move command from the XCA 305, YCA 310 and ZCA 315. Vector Bx 601 is the projection of Vector B on the X-axis, Vector By 602 is the projection of Vector B on the Y-axis, and Vector Bz 603 is the projection of vector B on the Z-axis. The angles α 604, β 605, and δ 606, are the corresponding angles between the vectors B and Bx, vectors B and By, and vectors B and Bz, respectively.

FIG. 18A illustrates one embodiment of a magnetic catheter tip 607. This magnetic tip 607 corresponds to the combination of the responsive tip 377 of the catheter assembly 375 and the responsive tip 381 of the guidewire assembly 379 (FIGS. 15 and 15A). The magnetic tip 607 is represented by its two poles $a_N$, 607A and $a_S$ 607B in connection with a Virtual Origin 608. The Virtual Origin 608 is defined by the center of travel of the Virtual Tip (VT) 405 in the X-, Y-, and Z-axes 400, 401 and 402 (FIG. 6). The Virtual Origin 608 also coincides with the center of the travel of the calibration magnet 411 in the X-, Y-, and Z-axes 406, 407 and 408, during calibration (FIG. 12). The assumption is that the Virtual Origin 608 is in the center of the x-ray field of view, as well as the center of the sagnetic field sensors (MFS) sensing volume and the center of the electromagnet (EM) control volume. The Virtual Origin 608 also coincides with the center of travel of the Calibration Fixture (CF) in the X, Y, and Z axes, during calibration.

FIG. 18B illustrates the resultant position vector An 609 that defines the position of the catheter tip 607 as detected by the magnetic field sensor arrays 307, 308, 312, 313, 317, and 318 and computed by microcontrollers 102x, 102y and 102z of XCA 305, YCA 310 and ZCA 315. The constituent vectors Xn, Yn, and Zn are the projections of the position vector An on the X-axis, Y-axis and Z-axis, respectively. The angles α 609A, β 609B, and γ 609C, are the projected angles of the vector $A_N$ on the X, Y, and Z axes, respectively. This orthogonal representation corresponds to the polar configuration 374 of FIG. 16.

Figure 18C:
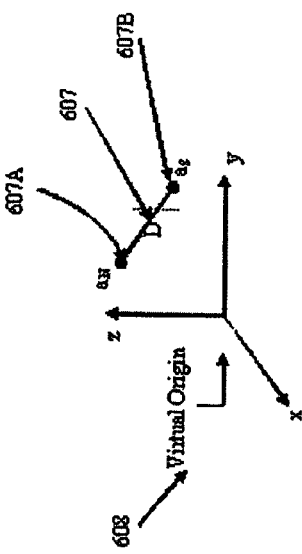
FIG. 18C illustrates the angle of the resultant vector of FIG. 18B in three dimensions.

FIG. 18C illustrates the angular representation of the resultant position vector of catheter tip 607 in 3 dimensions. The position vector An 609 shown in FIG. 18B define the location of $a_N$ 607A which is one of the two poles of the magnetic tip 607, is projected on the X-Y plane. This projected vector $\theta_{XY}$ 615 can be defined by an angle $\theta_X$ 613 with relation to the X-axis, and an angle $\theta_Y$ 614 with relation to the Y-axis. The projection on the X-Z plane and Y-Z planes are not shown thus the angular relationship of location $a_N$ with the Z-axis 612 is not shown for purposes of simplicity. These angular relationships of the position vector An defining the location $a_N$, as exemplified by $\theta_X$ 613 and $\theta_Y$ 614 are used in the calculations defining the positions of the actual catheter tip 377 as sensed by the magnetic field sensors sensor arrays 307, 308, 312, 313, 317, and 318. An explanation of these calculations will be provided later.

FIG. 19 illustrates the distance XD 616 between two opposite faces or poles of the electromagnets. The distance XD is used in calculations made during the operation of the system which will be explained in the following discussion.

FIG. 19A illustrates a distance d 617 between two adjacent X-axis magnetic field sensors. Magnetic field sensors −X1 and −X2 618 and 619 respectively. Also shown in FIG. 19A are two additional magnetic field sensors, −X3 and −X4. The magnetic field sensors $-X_1, -X_2, -X_3, -X_4$ are the MFS and the temperature sensor (TS) pairs, corresponding to 354, 355, 356, and 357, respectively, and $X_1, X_2, X_3$, and $X_4$ are the MFS and TS pairs corresponding to 350, 351, 352, and 353, respectively.

Figure 20:
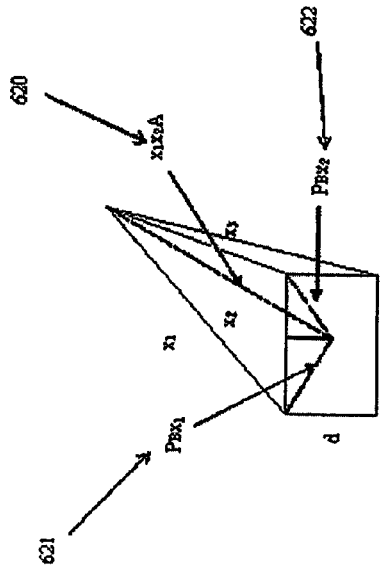
FIG. 20 is a representation of the process of deducing the location of the tip of FIG. 18A by the magnetic field sensors of FIG. 19A.

FIG. 20 illustrates the geometrical process by which the system deduces the true location of the magnetic tip 607 from the data it receives from the magnetic field sensors X1, X2, X3, and X4. The resultant vector A 620 is further manipulated by the system to generate position co-ordinates 621 and 622 of the tip 607, thereby identifying the location of the actual tip 377. This geometrical process will become apparent in the following discussion.

Figure 20A:
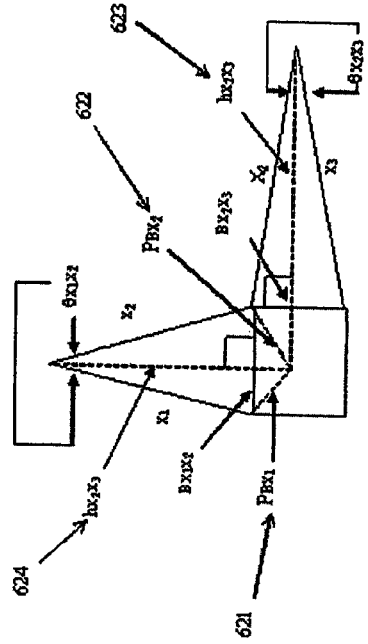
FIG. 20A illustrates the result of further calculations of the signals from the magnetic field sensors of FIG. 19A.

FIG. 20A further illustrates components of the position vectors 622 and 621 obtained by additional mathematical manipulation and calculations done on the signals that are received from the magnetic field sensors X1, X2, X3, and X4. The location of the actual tip 377 is defined by the position co-ordinates shown as 621 and 622. Position 623 is the measured position of the actual catheter tip 377 as determined by the magnetic field sensors X1, X2, X3, and X4, and position 624 is its calculated position as determined by the system control 302. Under ideal conditions, the positions 623 and 624 are equal to each other.

Figure 21:
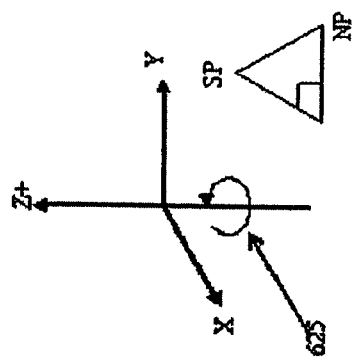
FIG. 21 is a representation of the rotation of the magnetic tip of FIG. 18A in the Z axis ($\theta$) direction.
Figure 22:
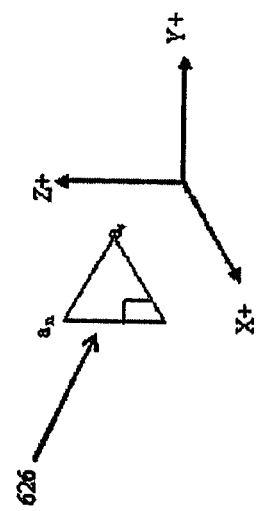
FIG. 22 is a representation of the translation of the magnetic tip of FIG. 18A in the Z axis ($\Delta Z$) direction.

FIG. 21 illustrates the rotation 625 of the tip 607 around the Z-axis (θ). The rotation is actually an arc motion occurring or oscillating in the X-Y plane. FIG. 22 illustrates the translation 626 of the tip 607 in the Z-axis.

The system controller (SC) 302 deduces the location of the actual catheter tip 377 from the signals generated by the magnetic field sensor arrays 307, 308, 312, 313, 317, and 318. This is done as described in the following paragraphs.

The following notations are assigned to the variables associated with FIGS. 18A, 19, and 19A:

$a_N$: North direction.

$a_S$: South direction.

$a_D$: Length of Tip Magnet.

$X_D$: Distance between opposite Poles 132x to 138x.

$-x_1, -x_2, -x_3, -x_4$: MFS and TS pairs 354, 355, 356, 357, respectively.

d: The Distance between magnetic field sensors and temperature sensor pairs 354 and 355, etc.

$x_1, x_2, x_3, x_4$: MFS and TS Pairs 350, 351, 352, 353, respectively.

ROT: θ AXIS

ELEV: EL AXIS

With reference to FIGS. 18a, 18b, and 18c, the positions of the actual tips 377 are defined by the orthogonal vectors $a_N$, $A_N$ and $a_S$, $A_S$. These orthogonal vectors are the resultant vectors of their constituent x, y and z components:

$$A_N = (Xn, Yn, Zn),$$

where Xn, Yn, and Zn are the projections of orthogonal vector $A_N$ on the X, Y, and Z axes (refer to FIG. 18B), and, $$A_S = (Xs, Ys, Zs)$$

where Xs, Ys and Zs are the projections of orthogonal vector $A_S$ on the X-, Y-, and Z-axes, respectively.

The directions of orthogonal vectors $A_N$ and $A_S$ from the origin are defined by the following angles (refer to FIG. 18B):
α is the angle to the X axis;
β is the angle to the Y axis; and
γ is the angle to the Z axis.

Similarly, the directions of the vector B are shown in FIG. 18 and defined by the three angles: α, β, and γ.

The distance of the vector $A_N$ from the virtual origin to the point $a_N$ 607A (FIG. 18C) is calculated by the following equation:

$$a_N = \sqrt{Xn^2 + Yn^2 + Zn^2},$$

and the angles defining the direction of vector $A_N$ are calculated by the following equations:

$$\alpha = \cos^{-1}\left[\frac{Xn}{An}\right] = \cos^{-1}\left[\frac{Xn}{\sqrt{Xn^2 + Yn^2 + Zn^2}}\right]$$

$$\beta = \cos^{-1}\left[\frac{Yn}{An}\right] = \cos^{-1}\left[\frac{Yn}{\sqrt{Xn^2 + Yn^2 + Zn^2}}\right]$$

$$\Upsilon = \cos^{-1}\left[\frac{Zn}{An}\right] = \cos^{-1}\left[\frac{Zn}{\sqrt{Xn^2 + Yn^2 + Zn^2}}\right]$$

With three orthogonal planes shown in FIG. 18C on which the positional vector $A_N$ is projected, producing the constituent vectors in each plane and their respective angles. The vectors in these three planes, X-Y, X-Z, and Y-Z are as follows:

In the X-Y plane the angles of the projected vector θxy with respect to the X-axes and the Y-axis (refer to FIG. 18C) are expressed as follows:

$$\theta x = \arctan\left(\frac{Xn}{Yn}\right), \text{ and}$$

$$\theta y = \arctan\left(\frac{Yn}{Xn}\right),$$

where the magnitude of the projected vector θxy in the X-Y plane is:

$$Axy = \sqrt{Xn^2 + Yn^2}.$$

Similarly, the angles of the projected vector θxy with respect to the X-axis and the Z-axis are expressed as follows:

$$\theta x = \arctan\left(\frac{Xn}{Yn}\right), \text{ and}$$

$$\theta z = \arctan\left(\frac{Zn}{Xn}\right),$$

and the magnitude of the projected vector θxz in the X-Z plane is:

$$Axz = \sqrt{Xn^2 + Zn^2}.$$

Similarly, the angles of the projected vector θxy with respect to the Y-axis and the Z-axis are expressed as follows:

$$\theta y = \arctan\left(\frac{Yn}{Zn}\right), \text{ and}$$

$$\theta z = \arctan\left(\frac{Zn}{Yn}\right),$$

and the magnitude of the projected vector θyz in the Y-Z plane is:

$$Ayz = \sqrt{Yn^2 + Zn^2}.$$

It should be noted that the mathematical solution of the vector $A_S = (X_S, Y_S, Z_S)$ follows the mathematical solution of the vector $A_N = (X_N, Y_N, Z_N)$.

As shown in FIG. 18A, if the distance D 607 between $a_N$ and $a_S$ is known, then:

$$D = \sqrt{(Xn - Xs)^2 + (Yn - Ys)^2 + (Yn - Ys)^2}$$

To illustrate how system controller 302 determines the position of the actual catheter tip, the calculations used by microprocessor 102x of XCA 305 with respect to the X-axis and the virtual origin 608 will now be described, with the understanding that microprocessors 102y of YCA 310 and 102z of ZCA 315 will perform similar calculations, with each generating positional data concerning the Y- and Z-axes, respectively.

The transfer functions of the co-planar magnetic field sensors ($x_1$, $x_2$, $x_3$, $x_4$) are known from the calibration routine ($fx_1$, $fx_2$, $fx_3$, $fx_4$) as shown in FIG. 20, and they are as follows:

$$-X_1 = -(V_{-x_1}(f_{-x_1})) \quad +X_1 = (V_{-x_1}(f_{-x_1}))$$

$$-X_2 = -(V_{-x_2}(f_{-x_2})) \quad +X_2 = (V_{-x_2}(f_{-x_2}))$$

$$-X_3 = -(V_{-x_3}(f_{-x_3})) \quad +X_3 = (V_{-x_3}(f_{-x_3}))$$

$$-X_4 = -(V_{-x_4}(f_{-x_4})) \quad +X_4 = (V_{-x_4}(f_{-x_4}))$$

Each MFS/TS pair 354, 355, 356, 357 mounted on the polar face of electromagnet 138x will provide location data to microprocessor 102x of XCA 305. The measured distance to $a_N$ 607A, for example, from MFS/TS pair 354 will be referred to as $(-x_1)$; the distance measured by MFS/TS pair 355 will be referred to as $(-x_2)$; the distance measured by MFS/TS pair 356 will be referred to as $(-x_3)$; the distance measured by MFS/TS pair 357 will be referred to as $(-x_4)$.

Likewise, each MFS/TS pair 350, 351, 352, 353 mounted on the polar face of electromagnet 132x will provide location data to microprocessor 102x of XCA 305. The measured distance of $a_N$ 607A from MFS/TS pair 350 will be referred to as $(+x_1)$; the distance measured by MFS/TS pair 351 will be referred to as $(+x_2)$; the distance measured by MFS/TS pair 352 will be referred to as (+$x_3$); the distance measured by MFS/TS pair 353 will be referred to as (+$x_4$).

Since the MFS/TS pairs are arranged in a quadrant around the central X-axis, the individually measured distances of each MFS/TS temperature sensor are combined mathematically to determine the distance along the x-axis itself. This is done by determining a positional vectors $Ax_1x_2$, $Ax_2x_3$, $Ax_3x_4$, and $Ax_1x_4$. With reference to FIG. 20, the magnitude of positional vector $Ax_2x_3$, for example, is given by the following equation:

$$Ax_2x_3 = \frac{x_2x_3\operatorname{Sin}(\theta x_2 x_3)}{d}.$$

The magnitude of the positional vectors $Ax_1x_2$, $Ax_3x_4$, and $Ax_1x_4$ are calculated in a similar way.

In addition, as shown in FIG. 20A, the angle $\theta x_1x_2$, which, for example, is the sum of the angles between $Ax_1x_2$ and $x_1$ and $Ax_1x_2$ and $x_2$, gives the direction of $Ax_1x_2$ as follows:

$$\theta x_1 x_2 = \cos^{-1}\left(\frac{d^2 - x_1^2 - x_2^2}{2x_1 x_2}\right)$$

The numerical solution, is graphically shown in FIG. 20A is achieved by using the canonical formalism described below. It should be noted that this numerical solution is performed in for example in a background mode by microprocessor 102x of XCA 305 and similarly for y axis and z axis.

$$hx_1x_2 = \frac{x_1x_2\sin(\theta x_1 x_2)}{d}$$

$$Bx_1x_2 = \sqrt{x_1^2 - hx_1x_2^2}$$

$$\theta x_2 x_3 = \cos^{-1}\left(\frac{d^2 - x_2^2 - x_3^2}{2x_2 x_3}\right)$$

$$Ax_2x_3 = \frac{x_2x_3\operatorname{Sin}(\theta x_2 x_3)}{d}$$

$$Bx_2x_3 = \sqrt{x_2^2 - hx_2x_3}$$

$$P_Bx_1 = \sqrt{{}_Bx_1x_2^2 + {}_Bx_2x_3^2}$$

$$Ax_1x_2 = \sqrt{x_1^2 - P_Bx_1^2}$$

The angles of $\theta x_2x_3$, $\theta x_3x_4$, and $\theta x_1x_4$ are calculated in a similar way.

Based on the distances $Ax_1x_2$, $Ax_2x_3$, $Ax_3x_4$, and $Ax_1x_4$ from the polar face 138x to the point $a_N$, an average distance ($-x_n$) is determined as follows:

$$-x = \left(\frac{(-x_1 - x_2A) + (-x_2 - x_3A) + (-x_3 - x_4A) + (-x_4 - x_1A)}{4}\right).$$

Likewise, the distance from the polar face 132x to the point $a_N$ is determined as follows:

$$+x = \left(\frac{x_1x_2A + x_2x_3A + x_3x_4A + x_4x_1A}{4}\right).$$

In one embodiment, when weighting the averages by using more accurate sensors yields better results (as determined during calibration), then a weighted average is used.

The distance of $a_N$ from the virtual origin 608 is determined since the virtual origin is the common point of reference between the VT assembly 304 and the calibration fixture (CF) 321. These distances are given for the three axes by the following sets of equations, where $X_D$ 616 is the distance between two coaxial electromagnets 132x and 138x (refer to FIG. 19), $Y_D$ is the distance between two coaxial electromagnets 132y and 138y, and $Z_D$ is the distance between two coaxial electromagnets 132z and 138z:

$$\frac{X_D}{2} + (-X)\frac{X_D}{2} + (+X) \text{ where:} \left(\frac{X_D}{2} + (-X)\right) + \left(\frac{X_D}{2} + (-X)\right) = X_D$$

The same calculations apply to the y and z axes positions and with the three axes positions known will yield an absolute position. Therefore, relative to the virtual origin:

$$Xn = \begin{cases} \frac{X_D}{2} - (-Xn) \\ (+Xn) - \frac{X_D}{2} \end{cases} \quad Xs = \begin{cases} \frac{X_D}{2} - (-Xs) \\ (+Xs) - \frac{X_D}{2} \end{cases}$$

$$Yn = \begin{cases} \frac{Y_D}{2} - (-Yn) \\ (+Yn) - \frac{Y_D}{2} \end{cases} \quad Ys = \begin{cases} \frac{Y_D}{2} - (-Ys) \\ (+Ys) - \frac{Y_D}{2} \end{cases}$$

$$Zn = \begin{cases} \frac{Z_D}{2} - (-Zn) \\ (+Zn) - \frac{Z_D}{2} \end{cases} \quad Xs = \begin{cases} \frac{Z_D}{2} - (-Zs) \\ (+Zs) - \frac{Z_D}{2} \end{cases}$$

The system controller 302 deduces the following from the calculations to determine the center point of the magnetic element of the actual catheter tip:

$$X_C = \frac{Xn - Xs}{2}$$

$$Y_C = \frac{Yn - Ys}{2}$$

$$Z_C = \frac{Zn - Zs}{2}$$

Thus the GCI apparatus 501 derives the rotation in the X-Y plane as follows:

$$RotC = \tan^{-1}\left(\frac{Yn - Ys}{Xn - Xs}\right)$$

and the elevation in the X-Z plane as follows:

$$elevC = \tan^{-1}\left(\frac{Zn - Zs}{Xn - Xs}\right)$$

Using these results, system controller 302 can compare the actual catheter tip 377 location to the desired tip location. FIG. 23 illustrates a logical computational flow taken by the system controller (SC) 302 in determining the position of the actual tip 377, using the following mathematical relations:

1. System Controller (SC) 302 inhibits X-axis controller and amplifier (XCA) 305, Y-axis controller and amplifier (YCA) 310, and Z-axis controller and amplifier (ZCA) 315 modulator outputs.
2. X-axis controller and amplifier (XCA) 305, Y-axis controller and amplifier (YCA) 310, and Z-axis controller and amplifier (ZCA) 315 read the magnetic field sensor array 307, 308, 312, 313, 317, and 318 outputs.
3. X-axis controller and amplifier (XCA) 305, Y-axis controller and amplifier (YCA) 310, and Z-axis controller and amplifier (ZCA) 315 read temperature sensor (TS) array 306, 309, 311, 314, 316, and 319 outputs.
4. X-axis controller and amplifier (XCA) 305, Y-axis controller and amplifier (YCA) 310, and Z-axis controller and amplifier (ZCA) 315 apply digital temperature compensation to the outputs of the magnetic field sensor arrays 307, 308, 312, 313, 317, and 318 by referring to correction data (typically stored in Non Volatile Memory 105*x*, 105*y*, and 105*z*).
5. System Controller (SC) 302 inputs the corrected magnetic field sensor data from X-axis controller and amplifier (XCA) 305, Y-axis controller and amplifier (YCA) 310, and Z-axis controller and amplifier (ZCA) 315, and interpolates a 5-axis data set from the three orthogonal components (Bx, By, Bz) of the magnetic field produced by the actual tip. The tip position is calculated using the following two relations:
   a) The magnitude of the force vector B 600 is given by the equation:
   $$B = \sqrt{Bx^2 + By^2 + Bz^2};$$ and
   b) the direction of the force vector B is given by the three resultant angles, as:
   $$\alpha = \frac{\cos^{-1} Bx}{B}, \beta = \frac{\cos^{-1} By}{B}, \delta = \frac{\cos^{-1} Bz}{B}$$
6. System Controller (SC) 302 inputs the cardio position (CP) from the auxiliary equipment (x-ray, ultrasound, etc) 322 via Communication Controller (CC) 320. The cardio position (CP) data set is dynamic due to the beating of the heart.
7. System Controller (SC) 302 calculates the actual position (AP) by combining the cardio position (CP) and the HP data sets.
8. System Controller (SC) 302 inputs Virtual Tip 405 position data from Virtual Tip/Calibration Fixture Controller (VT/CFC) 303.
9. System Controller (SC) 302 calculates the DP by combining the cardio position (CP) data set with that of the Virtual Tip (VT).
10. System Controller (SC) 302 then determines the position error (PE) by comparing the DP with the AP.
11. If the position error PE is less than an error threshold value, then the System Controller (SC) 302 enables X-axis controller and amplifier (XCA) 305, Y-axis controller and amplifier (YCA) 310 and Z-axis controller and amplifier (ZCA) 315 with the continues to use the same modulation and polarity.
12. If the position error PE is greater than the error threshold value, then the System Controller SC 302 alters the duty cycle and/or polarity of the modulation inputs to XCA 305, YCA 310, and ZCA 315 accordingly.

The System Controller (SC) 302 controls the stepper motors 55, 57, 59, 61, and 63 via the Virtual Tip/Calibration Fixture Controller (VT/CFC) 303 to produce tactile feedback if the position error (PE) exceeds a predetermined amount in a predetermined time in any axis or axes, thereby notifying the operator of an obstruction encountered by the catheter tip. That is, it is assumed that if the PE is not eliminated by the normal operation of the GCI apparatus 501 within an expected amount of time or cycles of steps 1 through 12 above, then an obstacle is likely to have been encountered by the actual catheter tip. This is perceived by the operator through tactile feedback generated by resistance produced the stepper motors 55, 57, 59, 61, and 63 acting on the virtual tip 405.

The operation of the virtual tip 405 is relatively simple and intuitive to the user or surgeon. The surgeon simply pushes, pulls, or rotates the virtual tip 405 in the desired direction to cause a similar movement of the catheter tip 377 within the patient's body. If an obstruction is encountered by the catheter tip 377, the virtual tip 405 responds with tactile feedback in the form of resistance to movement in the appropriate axis or axes. Thus, the surgeon can "feel" the actual tip as it is advanced. When tip 405 is released, the catheter tip 377 is forcefully held in its current position. System Controller (SC) 302 correlates the AT position with CP data obtained from auxiliary equipment 322 and via CC 320 it communicates with PC 324 in order to present monitor 325 with the combined tip and x-ray/ultrasonic imagery. The display of the three-dimensional AT position is continuously updated on a real-time basis with HP data. Relatively fewer frames of x-ray imagery are used to overlay the display with CP data. This correlation of AT and CP data is possible because the x-ray and the MFS arrays have a common reference point (i.e., both are stationary relative to the beating heart). The present technique significantly reduces x-ray exposure to the patient and staff while providing a superior method of observing the heart and catheter tip 377.

Accordingly, it can be seen that the new catheter guidance and control apparatus and method provide an arrangement which is: relatively easy to use effectively; requires minimal training to master; rapidly advances and accurately positions the catheter tip; requires fewer types of catheters; forcefully fixates the catheter tip in the desired position; steers a guidewire through a torturous path; forcefully advances a guidewire or balloon through plaque; displays the catheter tip position in three dimensions; significantly reduces the amount of contrast material the patient is exposed to; significantly reduces the amount of X-radiation the patient and medical staff are exposed to; is intuitive to use; and produces tactile feedback to indicate when the catheter tip encounters an obstruction.

Although the preceding description contains much specificity, this should not be construed as limiting the scope of the invention, but as merely providing illustrations of embodiments thereof. Many other variations are possible within the scope of the present invention. For example, the modulation of the electromagnets can be controlled in such a way as to cause a vibratory or pulsating motion of the tip to aid in crossing plaque; the responsive tip(s) can be electromagnetic rather than permanent magnets; the magnetic field external to the body can be generated by a permanent magnet or magnets; the control of the external magnetic field can be accomplished by manually administering the field generating devices; AC induction with its associated magnetic effects can be utilized by causing a coil or coils wound around the tip to respond to an impressed time variant field; materials with Curie temperatures within a few degrees of body temperature can be used as magnetic flux switches for selective tip control by irrigating them with fluids having appropriate temperatures; electrostatic phenomena can enhance magnetic effects; artificial intelligence can replace the operator control for producing command inputs; an expert system can replace or augment operator inputs; the apparatus can be used to incubate various body cavities and organs other than the heart; the apparatus can be used for human and animal procedures such as egg harvesting and embryo implantation; the responsive tip can be attached to a coherent fiber optic bundle to provide viewing of internal structures with unprecedented maneuverability; internal radioisotope therapy can be precisely performed by delivering a palletized source directly to a tumor using a guided catheter; internal tissue samples can be obtained without major surgery; a fiber optic light guide equipped with a responsive tip can be accurately positioned to deliver laser light to a specific internal location without major surgery; previously difficult liposuction and other subcutaneous surgical procedures can be performed accurately, and so forth. Thus, the scope of the invention is limited only by the claims.

What is claimed is:

1. A catheter tip assembly, comprising;
a flexible portion proximate to a distal end of a catheter;
a rigid portion disposed at said distal end of said catheter and adjacent to said a distal end of said flexible portion;
a permanent magnet responsive to an applied magnetic field to move said catheter tip assembly, said permanent magnet disposed in said rigid portion; and
a plurality of piezoelectric rings disposed in said relatively rigid portion, said piezoelectric rings responsive to an applied ultrasonic signal, said piezoelectric rings producing data to measure a rotation of a north pole of said permanent magnet, a first piezoelectric ring of said plurality of piezoelectric rings disposed proximate to a distal end of said permanent magnet and a second piezoelectric ring of said plurality of piezoelectric rings disposed proximate to a proximal end of said permanent magnet.

2. The assembly of claim 1 further comprising a computer that determines an angle of said rotation.

3. The assembly of claim 2 wherein said computer further determines said rotation relative to a stereotactic framing.

4. The assembly of claim 1 wherein said distal end comprises one or more magnetic field sensors and one or more temperature sensors.

5. The assembly of claim 4 wherein said temperature sensors measure a temperature of said one or more magnetic field sensors.

6. The assembly of claim 1 further comprising a control system configured to calculate respective torque and associated current for a magnetic source to configure a magnetic field to move said distal end to a desired location.

7. The assembly of claim 1 further comprising a display of a visual representation of said distal end in substantially real time as said distal end moves through a body.

8. The assembly of claim 1 further comprising controlling one or more electromagnets to produce an external magnetic field.

9. The assembly of claim 2, wherein said computer determines a current position of said distal end in comparison to a desired location.

10. The assembly of claim 9, wherein said computer computes a position error of said distal end.

11. The assembly of claim 10 further comprising a tactile feedback system that is configured to produce a tactile feedback if said position error exceeds a predetermined amount along at least one axis.

* * * * *